(12) United States Patent
Kawata et al.

(10) Patent No.: US 8,546,584 B2
(45) Date of Patent: Oct. 1, 2013

(54) BENZOXAZOLE DERIVATIVE, LIGHT-EMITTING ELEMENT, LIGHT-EMITTING DEVICE, ELECTRONIC DEVICE, AND LIGHTING DEVICE

(75) Inventors: Yuko Kawata, Kanagawa (JP); Hiroshi Kadoma, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/304,866

(22) Filed: Nov. 28, 2011

(65) Prior Publication Data
US 2012/0132896 A1    May 31, 2012

(30) Foreign Application Priority Data
Nov. 30, 2010  (JP) .................... 2010-267158

(51) Int. Cl.
*C07D 413/10* (2006.01)
*B32B 9/00* (2006.01)
*H01J 1/62* (2006.01)

(52) U.S. Cl.
USPC ........ 548/224; 548/217; 313/506; 315/169.3; 428/690; 428/917

(58) Field of Classification Search
USPC ........ 549/90, 200; 313/504, 506; 315/169.3; 428/690, 917; 548/217, 224
See application file for complete search history.

(56) References Cited

U.S. PATENT DOCUMENTS

| | | | | |
|---|---|---|---|---|
| 3,796,707 | A * | 3/1974 | Siegrist et al. ............... | 548/224 |
| 5,587,112 | A * | 12/1996 | Kauffman et al. ............ | 252/589 |
| 2010/0060155 | A1 | 3/2010 | Seo et al. | |
| 2011/0114928 | A1 | 5/2011 | Suzuki et al. | |
| 2011/0147792 | A1 | 6/2011 | Kawata et al. | |
| 2011/0210316 | A1 | 9/2011 | Kadoma et al. | |
| 2011/0248246 | A1 | 10/2011 | Ogita et al. | |
| 2011/0285276 | A1 | 11/2011 | Kadoma et al. | |
| 2012/0061651 | A1 | 3/2012 | Osaka et al. | |
| 2012/0061714 | A1 | 3/2012 | Osaka et al. | |
| 2012/0071668 | A1 | 3/2012 | Suzuki et al. | |
| 2012/0074390 | A1 | 3/2012 | Seo et al. | |
| 2012/0080667 | A1 | 4/2012 | Nowatari et al. | |
| 2012/0091887 | A1 | 4/2012 | Osaka et al. | |
| 2012/0104369 | A1 | 5/2012 | Kawata et al. | |
| 2012/0104373 | A1 | 5/2012 | Inoue et al. | |
| 2012/0130081 | A1 | 5/2012 | Kawata et al. | |
| 2012/0133274 | A1 | 5/2012 | Kawakami et al. | |
| 2012/0157694 | A1 | 6/2012 | Osaka et al. | |
| 2012/0184755 | A1 | 7/2012 | Osaka et al. | |
| 2012/0193613 | A1 | 8/2012 | Kadoma et al. | |
| 2012/0289708 | A1 | 11/2012 | Kawakami et al. | |
| 2013/0009543 | A1 | 1/2013 | Kadoma et al. | |
| 2013/0048964 | A1 | 2/2013 | Takeda et al. | |
| 2013/0048971 | A1 | 2/2013 | Kitano et al. | |
| 2013/0060033 | A1 | 3/2013 | Seo et al. | |

FOREIGN PATENT DOCUMENTS

JP      2010-83876      4/2010

OTHER PUBLICATIONS

Specification U.S. Appl. No. 13/598,253, filed Aug. 29, 2012.

* cited by examiner

*Primary Examiner* — Golam M M Shameem
(74) *Attorney, Agent, or Firm* — Husch Blackwell LLP

(57) ABSTRACT

A novel benzoxazole derivative having high excitation energy, particularly high triplet excitation energy is provided. A light-emitting element having high current efficiency is provided by application of the novel benzoxazole derivative for the light-emitting element. A light-emitting device, an electronic device, and a lighting device each having reduced power consumption are provided. The benzoxazole derivative is represented by General Formula (G1). In the formula, $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, and Z represents either a sulfur atom or an oxygen atom.

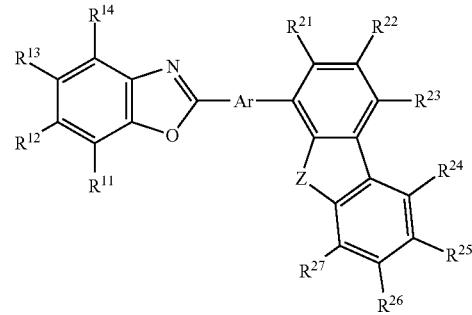

(G1)

20 Claims, 22 Drawing Sheets

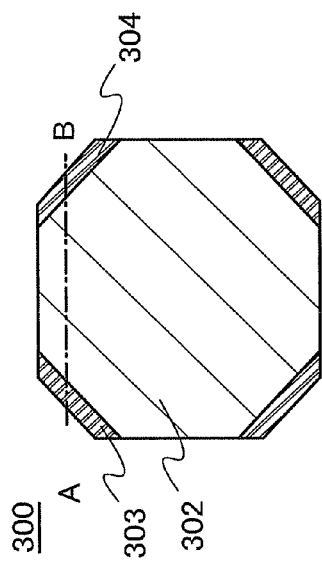
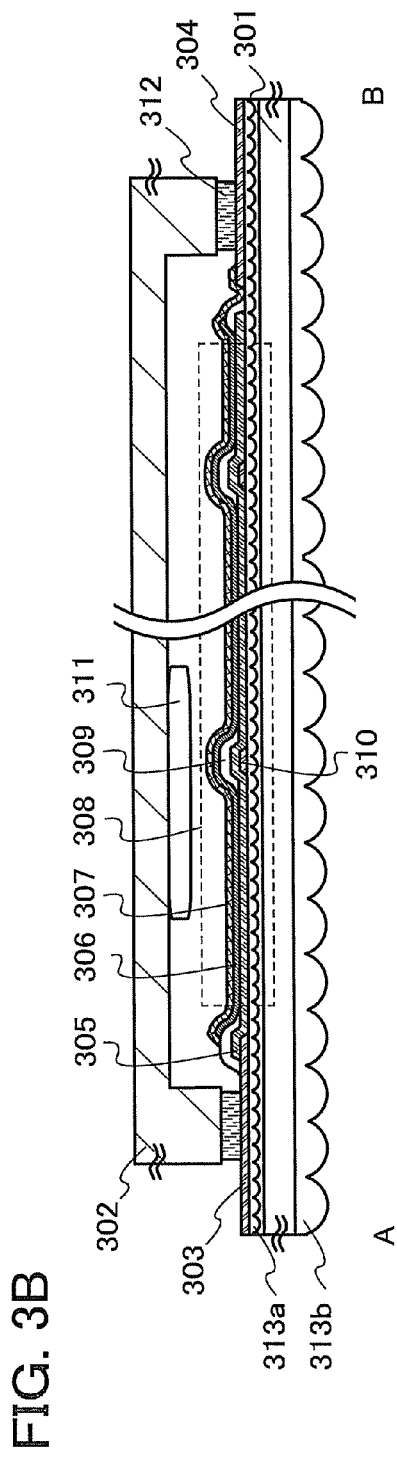
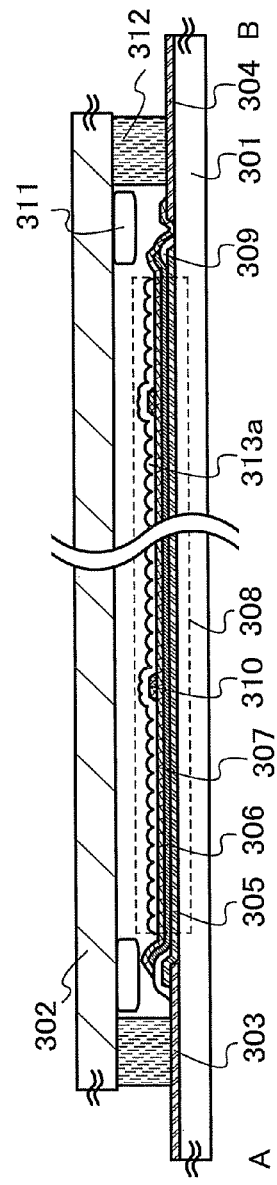
FIG. 3A
FIG. 3B
FIG. 3C

BENZOXAZOLE DERIVATIVE, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a benzoxazole derivative and a light-emitting element including the benzoxazole derivative. The present invention also relates to a light-emitting device, an electronic device, and a lighting device each including the light-emitting element.

2. Description of the Related Art

In recent years, research and development of light-emitting elements using electroluminescence (EL) have been actively conducted. In a basic structure of such a light-emitting element, a layer containing a light-emitting substance is interposed between a pair of electrodes. By voltage application to this element, light emission can be obtained from the light-emitting substance.

Such a light-emitting element is of self-luminous type, and thus has advantages over a liquid crystal display in that visibility of pixels is high, backlight is not needed, and so on. Therefore, such a light-emitting element is regarded as being suitable as a flat panel display element. Besides, such a light-emitting element has advantages in that it can be manufactured to be thin and lightweight, and has very fast response speed.

Further, since such a light-emitting element can be formed to have a film shape, plane light emission can be easily obtained. Therefore, a large-area element capable of the plane light emission can be formed easily. This is a feature that is difficult to obtain with point light sources typified by an incandescent lamp and an LED or linear light sources typified by a fluorescent lamp. Therefore, the light-emitting element is very effective for use as a surface light source applicable to a lighting device and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, these carriers (i.e., electrons and holes) are recombined, whereby the light-emitting organic compound is excited. The light-emitting organic compound returns to the ground state from the excited state, thereby emitting light. Note that the excited state of an organic compound can be a singlet excited state (S*) and a triplet excited state (T*), and luminescence from the singlet excited state is referred to as fluorescence, and luminescence from the triplet excited state is referred to as phosphorescence.

At room temperature, a compound that is capable of converting a singlet excited state to luminescence (hereinafter, referred to as a fluorescent compound) generally exhibits only luminescence from the singlet excited state (fluorescence), and does not luminesce from the triplet excited state (phosphorescence). Therefore, the internal quantum efficiency (the ratio of generated photons to injected carriers) in a light-emitting element using a fluorescent compound is assumed to have a theoretical limit of 25% on the basis of S*:T*=1:3.

On the other hand, when a compound in which a triplet excited state is converted into luminescence (hereinafter, such a compound is referred to as a "phosphorescent compound") is used, internal quantum efficiency can be theoretically 75% to 100%. In other words, emission efficiency which is 3 times to 4 times as much as that of a fluorescent compound can be obtained. For these reasons, a light-emitting element using a phosphorescent compound has been actively developed in recent years in order to achieve a highly efficient light-emitting element.

Further, since there is a need for energy saving, development of a light-emitting element consuming less energy is needed.

REFERENCE

Patent Document

[Patent Document 1] Japanese Published Patent Application No. 2010-83876

SUMMARY OF THE INVENTION

In view of the foregoing, an object of one embodiment of the present invention is to provide a novel benzoxazole derivative as a substance having high excitation energy, particularly as a substance having high triplet excitation energy. Another object of one embodiment of the present invention is to provide a light-emitting element having high current efficiency by application of the novel benzoxazole derivative for the light-emitting element. Another object of one embodiment of the present invention is to provide a light-emitting device, an electronic device, and a lighting device each having reduced power consumption.

One embodiment of the present invention is a benzoxazole derivative represented by General Formula (G1).

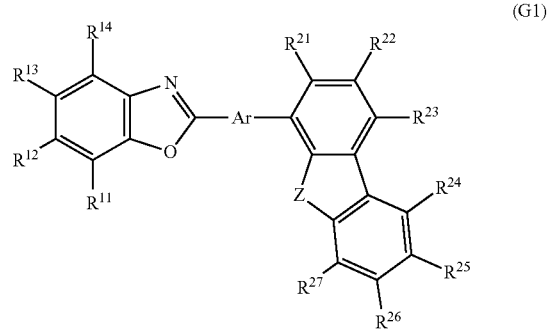

(G1)

Note that in General Formula (G1), $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, and Z represents either a sulfur atom or an oxygen atom.

One embodiment of the present invention is a benzoxazole derivative represented by the above general formula (G1) in which Ar represents either a substituted or unsubstituted phenylene group or a substituted or unsubstituted biphenyldiyl group.

One embodiment of the present invention is a benzoxazole derivative represented by General Formula (G2).

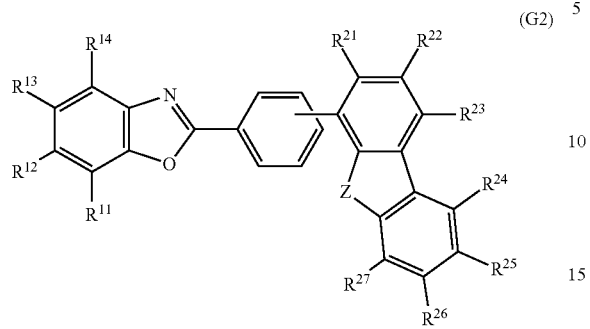

Note that in General Formula (G2), $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, and Z represents either a sulfur atom or an oxygen atom.

Further, the above $R^{11}$ to $R^{14}$ and $R^{21}$ to $R^{27}$ may be separately any one of structures represented by Structural Formulae (11-1) to (11-23).

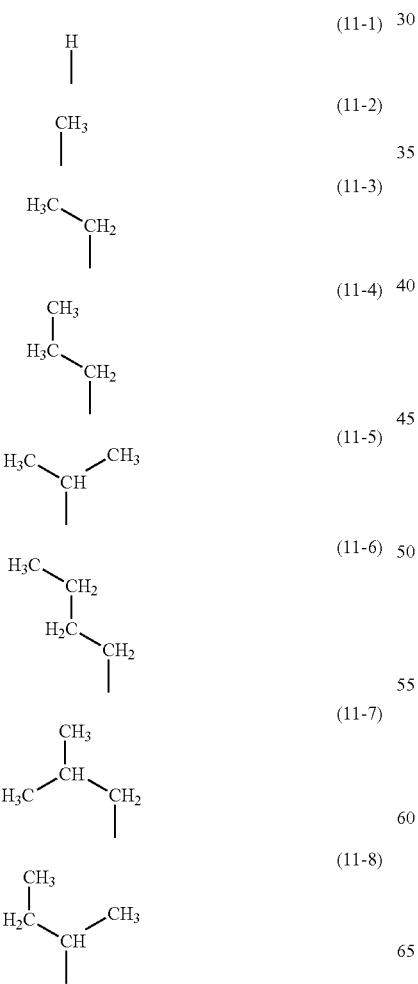

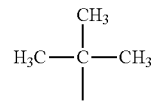

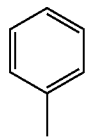

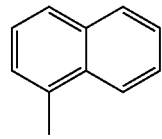

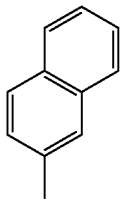

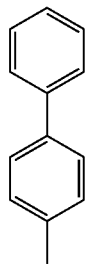

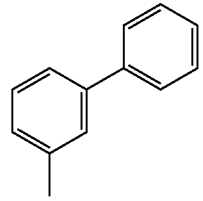

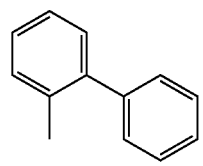

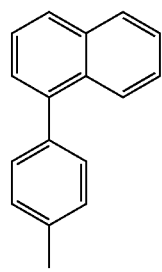

(11-17)
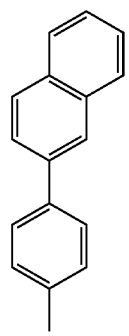
(11-18)
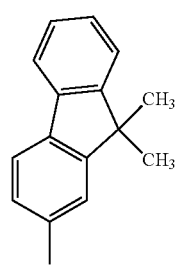
(11-19)
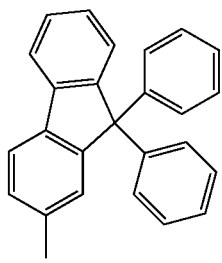
(11-20)
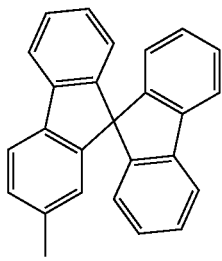
(11-21)
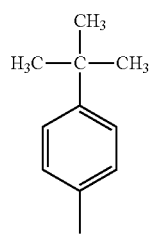
(11-22)
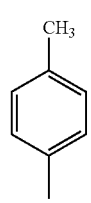
(11-23)
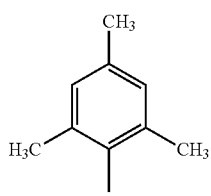
Further, Ar in General Formula (G1) may be any one of structures represented by Structural Formulae (12-1) to (12-15).
(12-1)
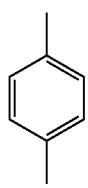
(12-2)
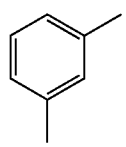
(12-3)
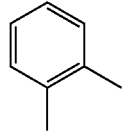
(12-4)
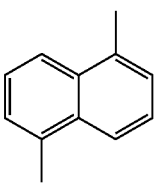
(12-5)
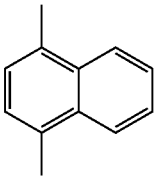
(12-6)
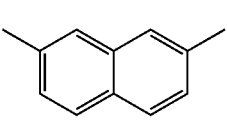

-continued (12-7) 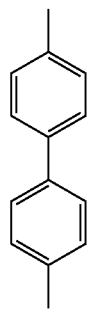

(12-8) 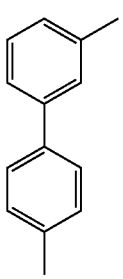

(12-9) 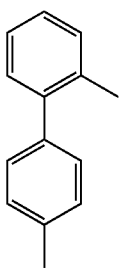

(12-10) 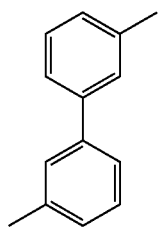

(12-11) 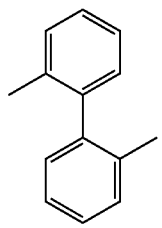

(12-12) 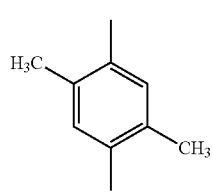

-continued (12-13) 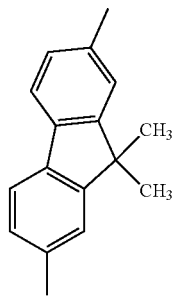

(12-14) 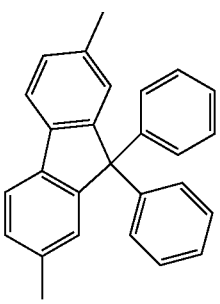

(12-15) 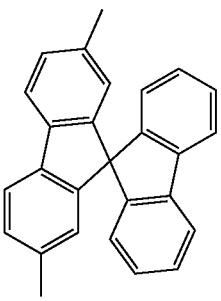

Further, one embodiment of the present invention is a light-emitting element including an electroluminescent (EL) layer between a pair of electrodes, in which the above-described benzoxazole derivative is included in the EL layer.

Note that since the benzoxazole derivative which is one embodiment of the present invention has high excitation energy, the benzoxazole derivative can be favorably used as a host material in the case where an EL layer includes a light-emitting layer containing a material (a guest material) having a high light-emitting property and a material (a host material) in which the guest material is dispersed. Accordingly, another embodiment of the present invention is a light-emitting element including, between a pair of electrodes, an EL layer in which a light-emitting layer contains the benzoxazole derivative which is one embodiment of the present invention and a guest material.

One embodiment of the present invention is a light-emitting device including the light-emitting element.

One embodiment of the present invention is a lighting device including the light-emitting device.

One embodiment of the present invention is an electronic device including the light-emitting device.

Note that the light-emitting device in this specification includes, in its category, an image display device, a light-emitting device, and a light source. In addition, the light-emitting device includes, in its category, all of a module in which a connector such as a flexible printed circuit (FPC), a tape automated bonding (TAB) tape, or a tape carrier package (TCP) is connected to a panel, a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel benzoxazole derivative as a substance having high excitation energy, particularly as a substance having high triplet excitation energy can be provided. According to one embodiment of the present invention, a light-emitting element having high current efficiency can be provided by application of the novel benzoxazole derivative for the light-emitting element. According to one embodiment of the present invention, a light-emitting device, an electronic device, and a lighting device each having reduced power consumption can be provided.

BRIEF DESCRIPTION OF THE DRAWINGS

FIGS. 3A to 3C illustrate light-emitting devices of one embodiment of the present invention.

DETAILED DESCRIPTION OF THE INVENTION

Figure 1A:
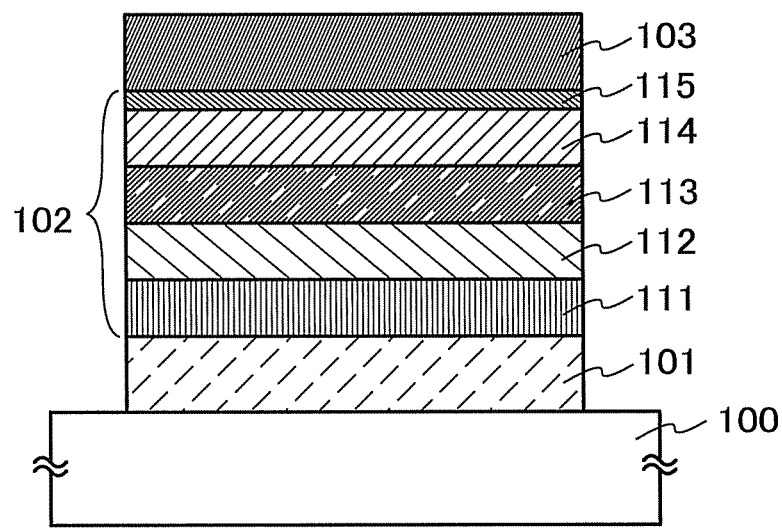
FIGS. 1A and 1B each illustrate a light-emitting element of one embodiment of the present invention.

Hereinafter, embodiments will be described in detail with reference to the accompanying drawings. Note that the present invention is not limited to the following description and it will be easily understood by those skilled in the art that various changes and modifications can be made without departing from the spirit and scope of the present invention. Therefore, the present invention should not be construed as being limited to the following description of the embodiments.

Embodiment 1

In this embodiment, a benzoxazole derivative of one embodiment of the present invention will be described.

The benzoxazole derivative of one embodiment of the present invention is a benzoxazole derivative represented by General Formula (G1).

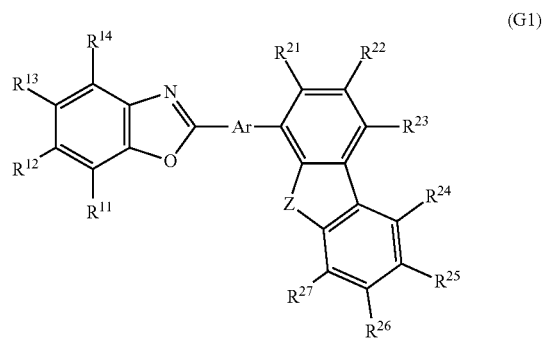

(G1)

Note that in General Formula (G1), $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, and Z represents either a sulfur atom or an oxygen atom.

Further, a benzoxazole derivative of another embodiment of the present invention is a benzoxazole derivative represented by the above general formula (G1) in which Ar represents either a substituted or unsubstituted phenylene group or a substituted or unsubstituted biphenyldiyl group.

A benzoxazole derivative of another embodiment of the present invention is a benzoxazole derivative represented by General Formula (G2).

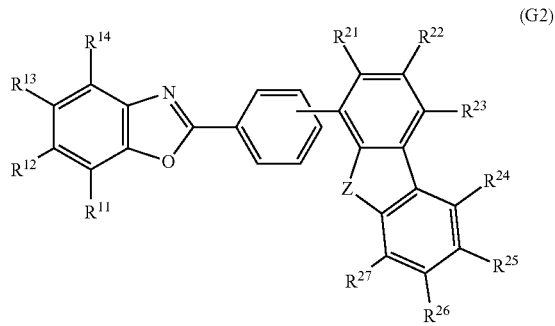

(G2)

Note that in General Formula (G2), $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, and Z represents either a sulfur atom or an oxygen atom.

Further, the above $R^{11}$ to $R^{14}$ and $R^{21}$ to $R^{27}$ may be separately any one of structures represented by Structural Formulae (11-1) to (11-23).
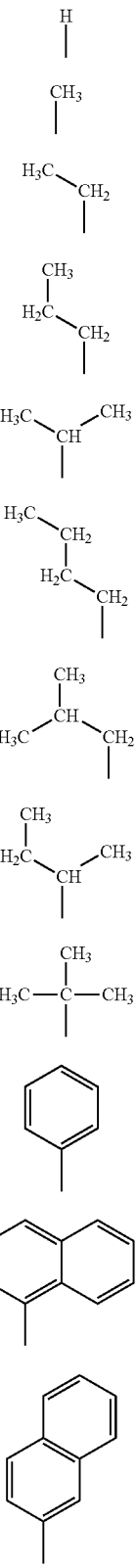
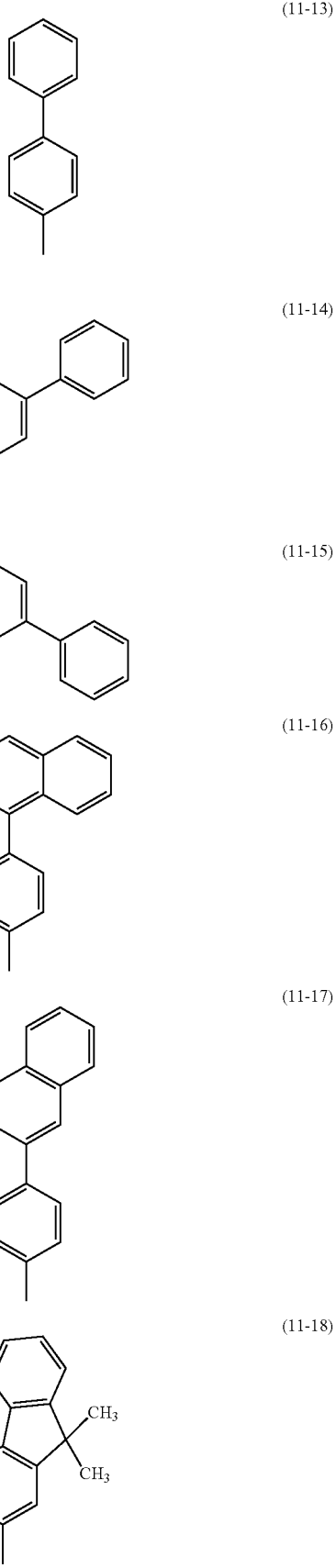

(11-19)
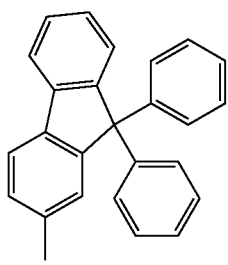
(11-20)
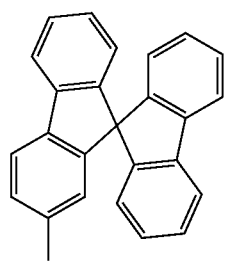
(11-21)
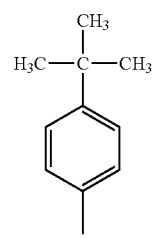
(11-22)
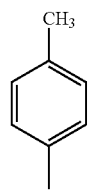
(11-23)
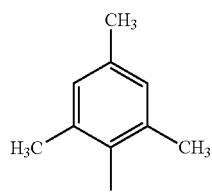
Further, Ar in General Formula (G1) may be any one of structures represented by Structural Formulae (12-1) to (12-15).
(12-1)
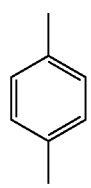
(12-2)
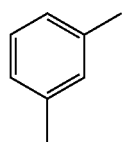
(12-3)
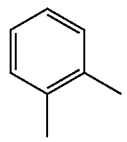
(12-4)
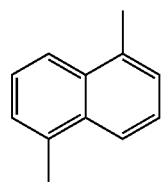
(12-5)
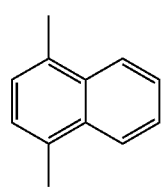
(12-6)
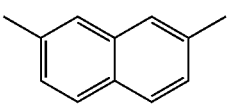
(12-7)
(12-8)
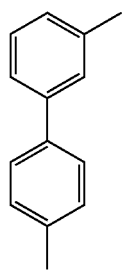

(12-9)
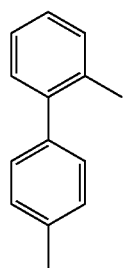
(12-10)
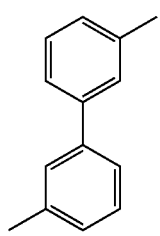
(12-11)
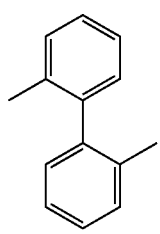
(12-12)
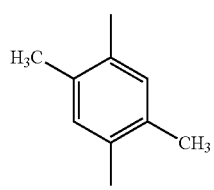
(12-13)
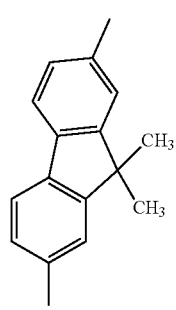
(12-14)
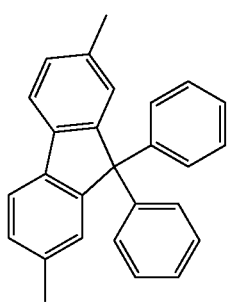
(12-15)
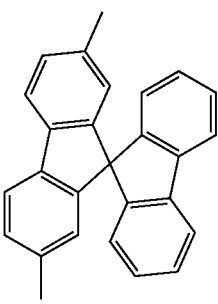
As specific examples of the benzoxazole derivative represented by General Formula (G1), benzoxazole derivatives represented by Structural Formulae (100) to (179) and Structural Formulae (200) to (279) can be given. However, the present invention is not limited to these structures.

(103)
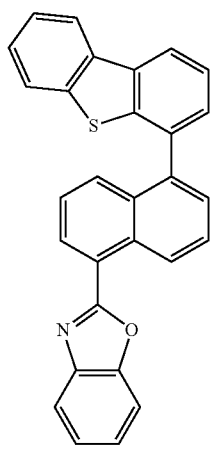
(104)
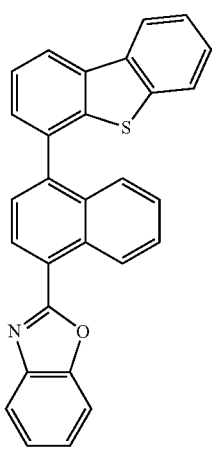
(105)
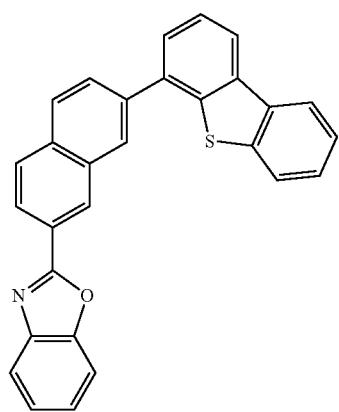
(106)
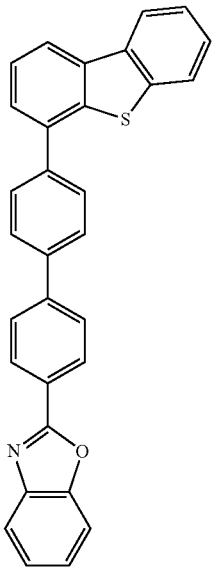
(107)
(108)
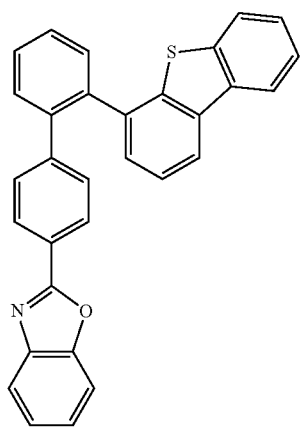

(109)
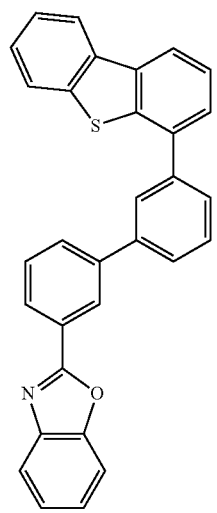
(110)
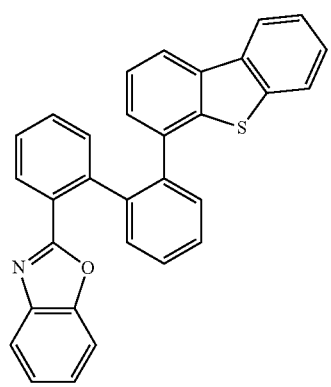
(111)
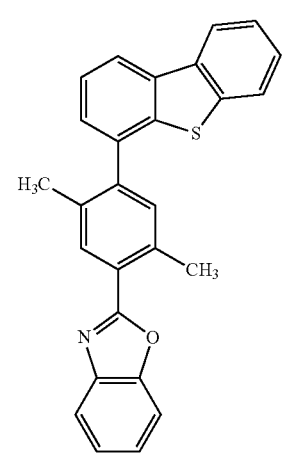
(112)
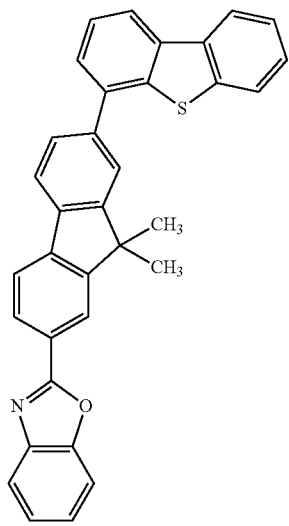
(113)
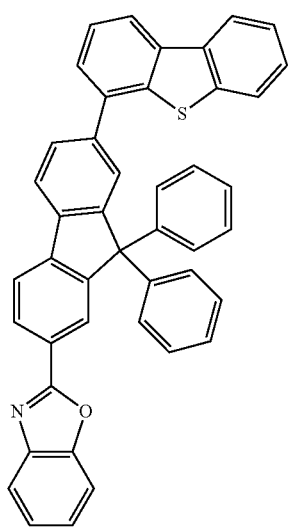
(114)
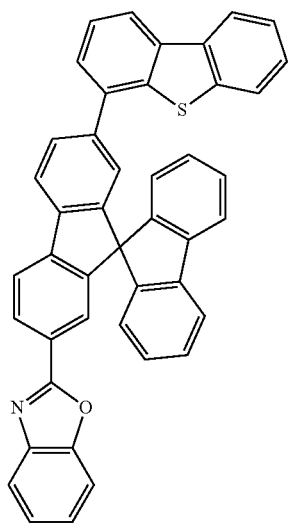

-continued
(115)
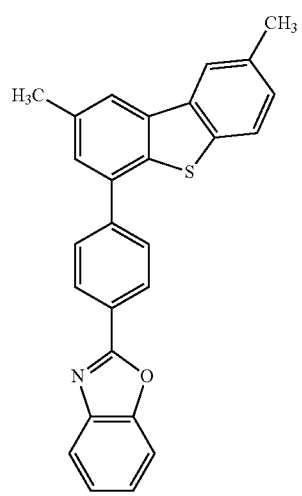
(116)
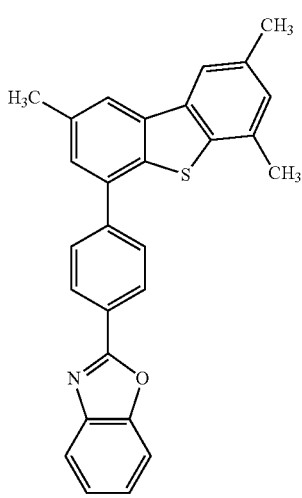
(117)
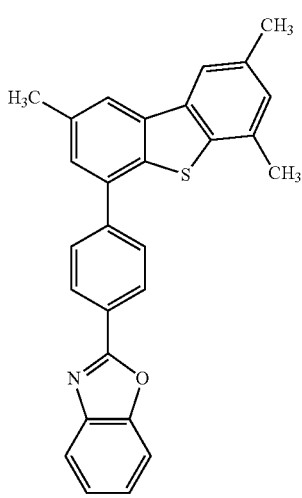
-continued
(118)
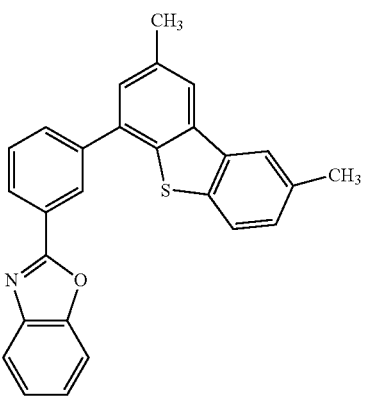
(119)
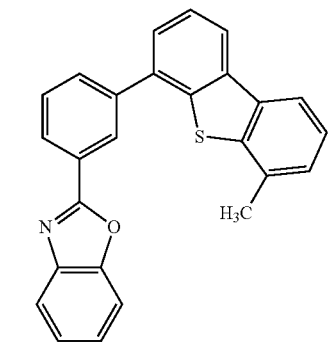
(120)
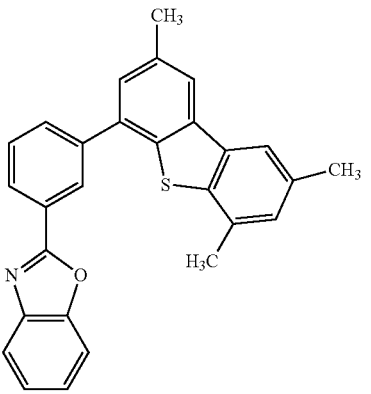
(121)
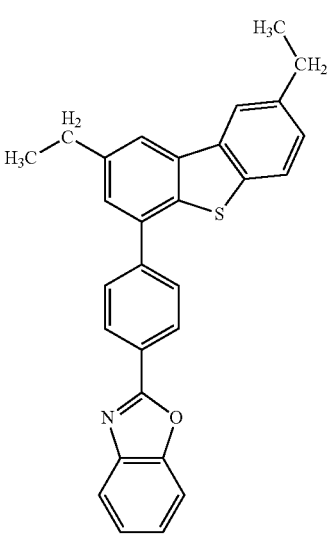

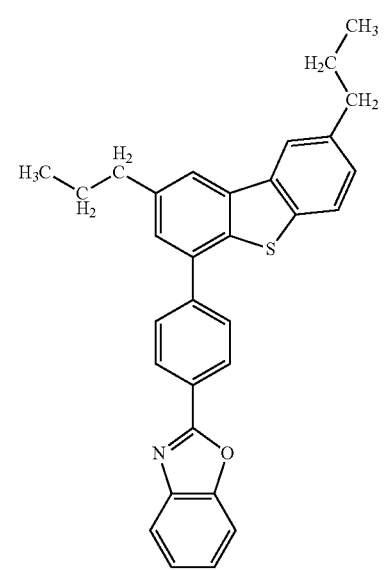
(122)
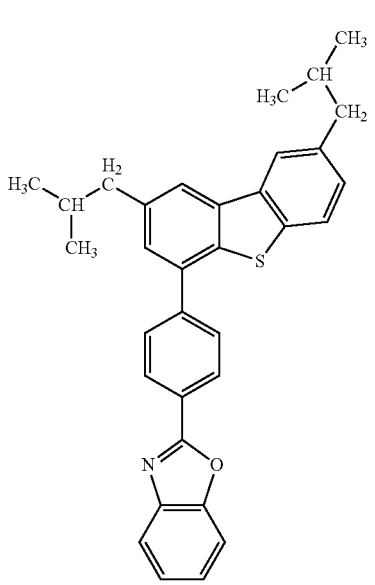
(125)
(123)
(126)
(124)
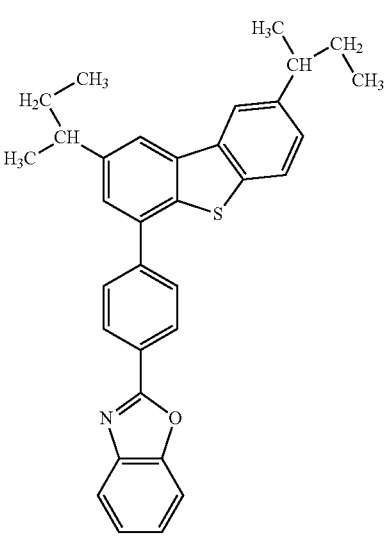
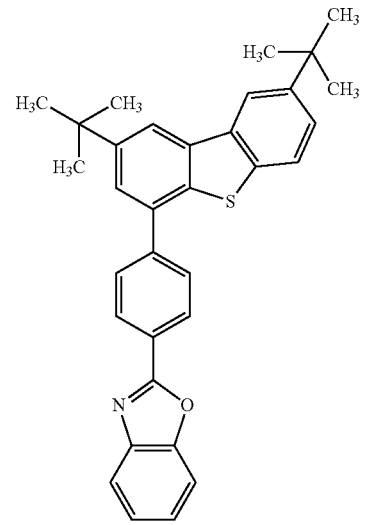
(127)

(128)
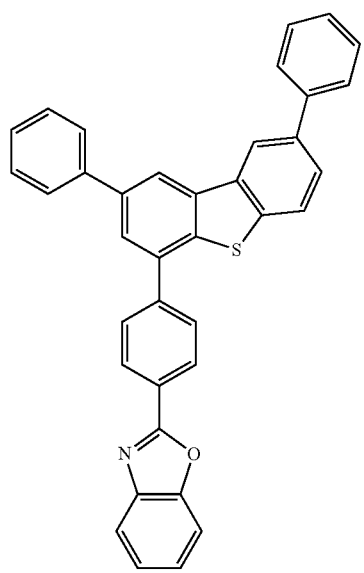
(129)
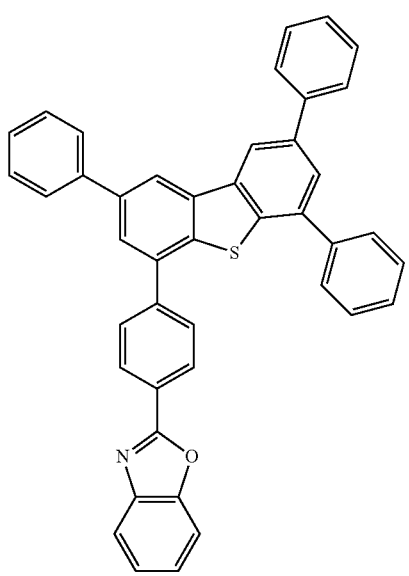
(130)
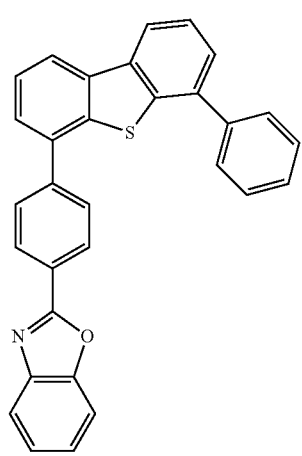
(131)
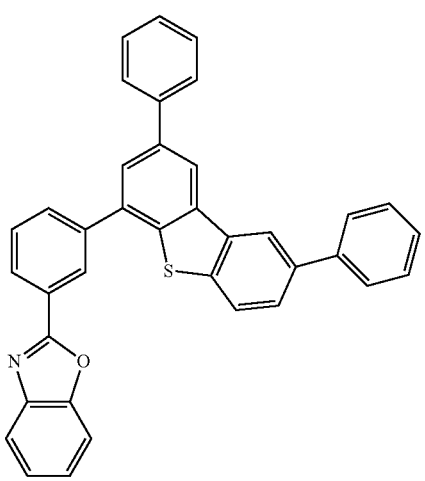
(132)
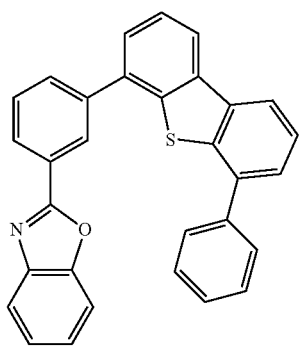
(133)
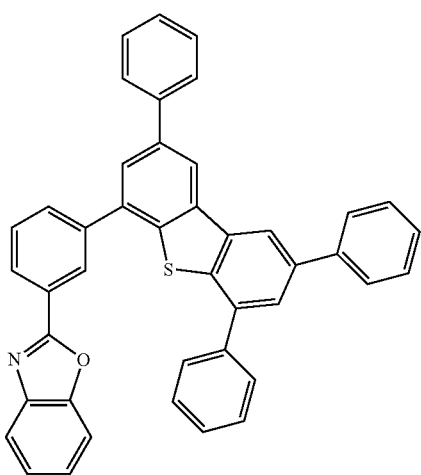

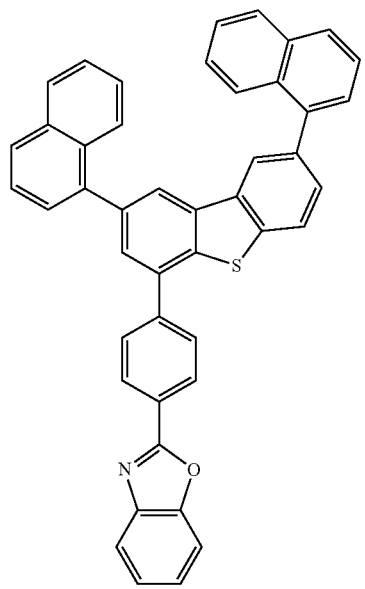
(134)
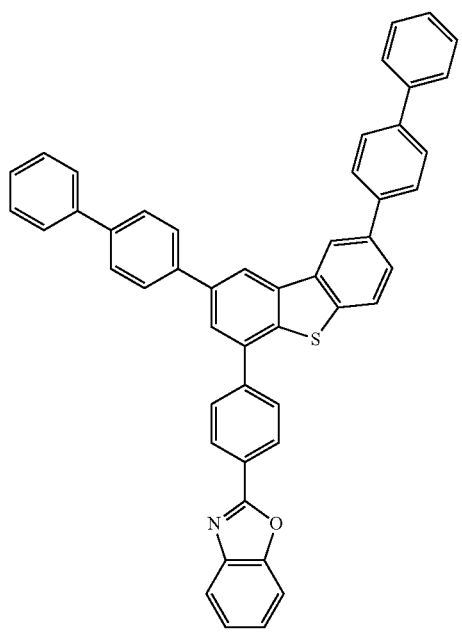
(136)
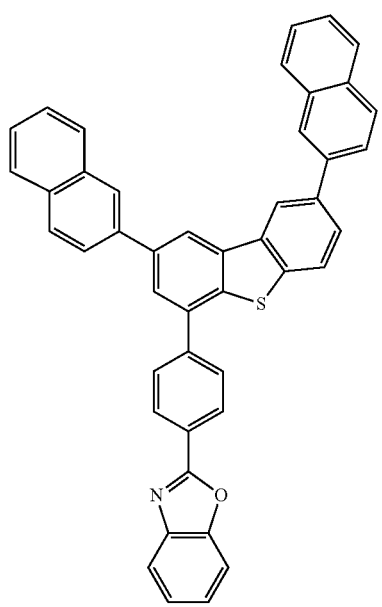
(135)
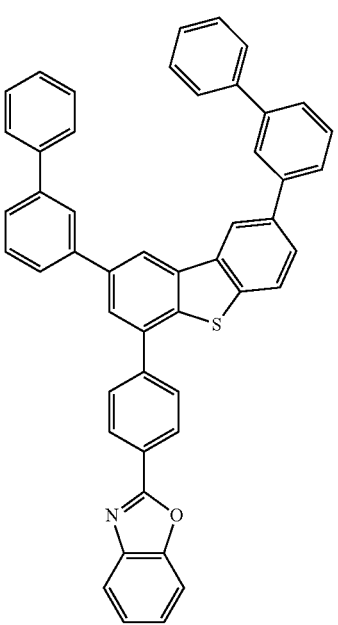
(137)

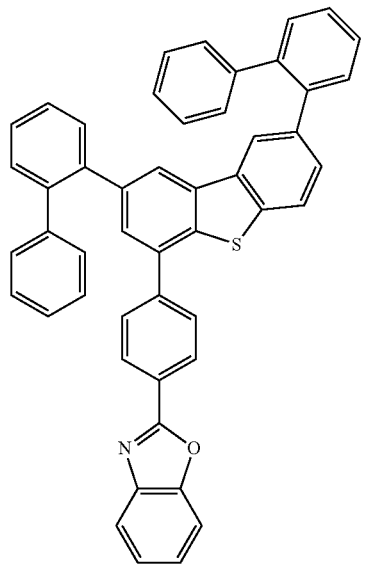
(138)
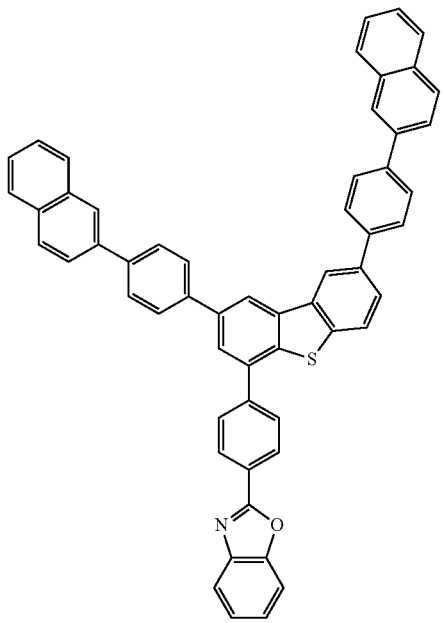
(140)
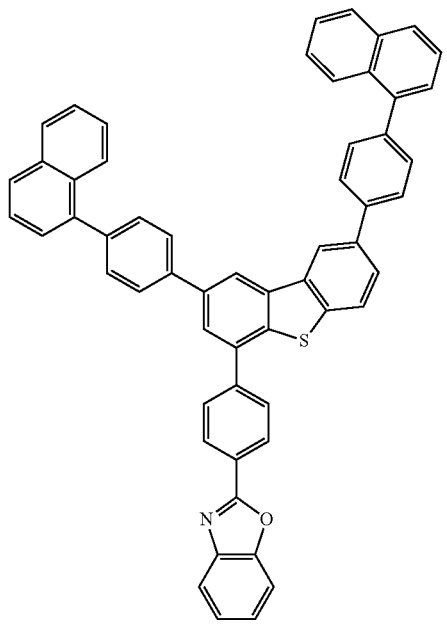
(139)
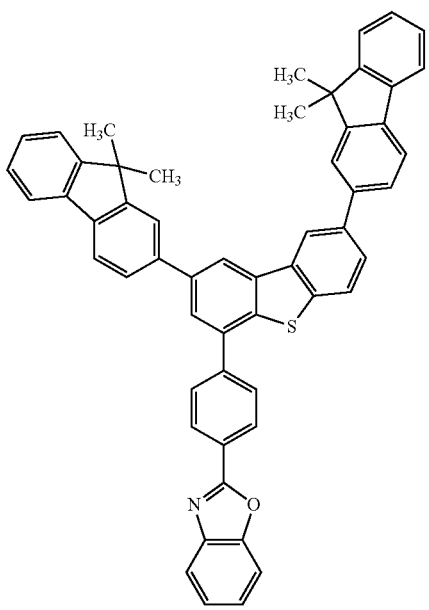
(141)

(142)
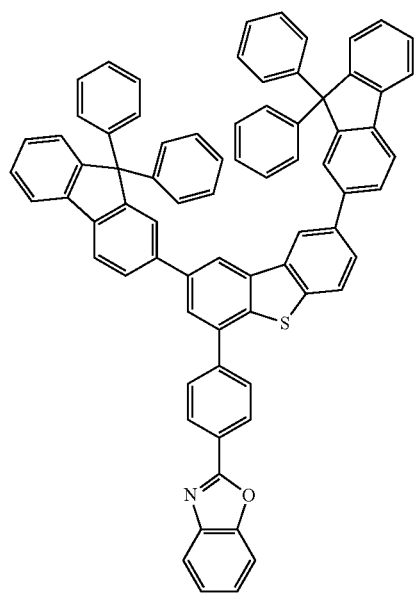
(143)
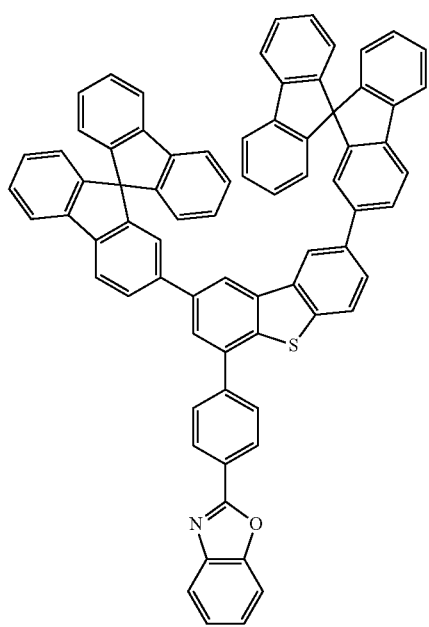
(144)
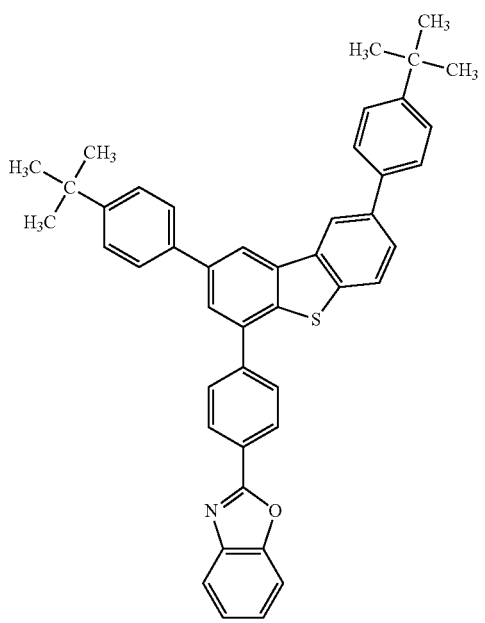
(145)
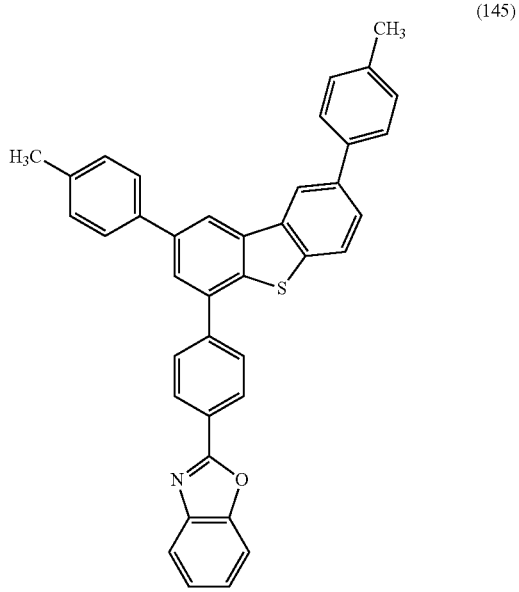

(146)
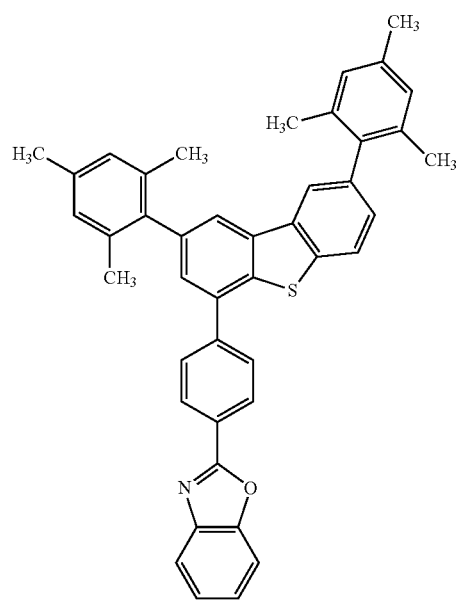
(147)
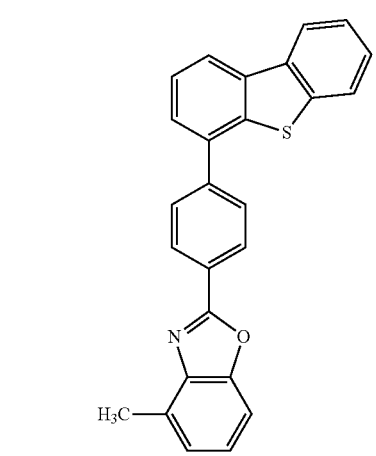
(148)
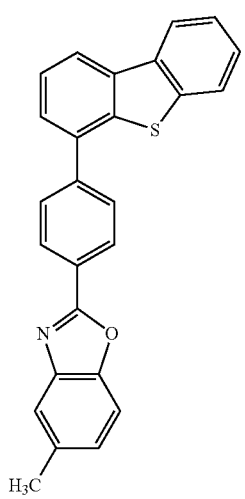
(149)
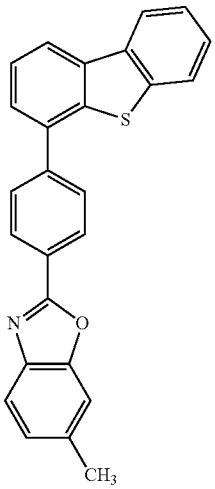
(150)
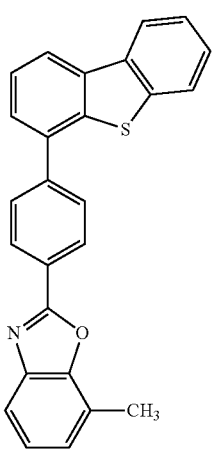
(151)
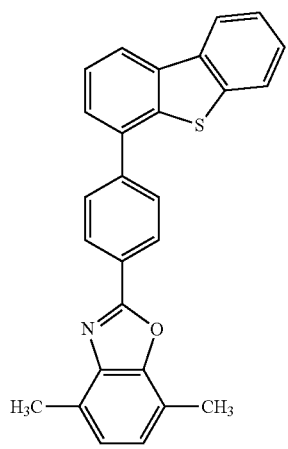

(152) 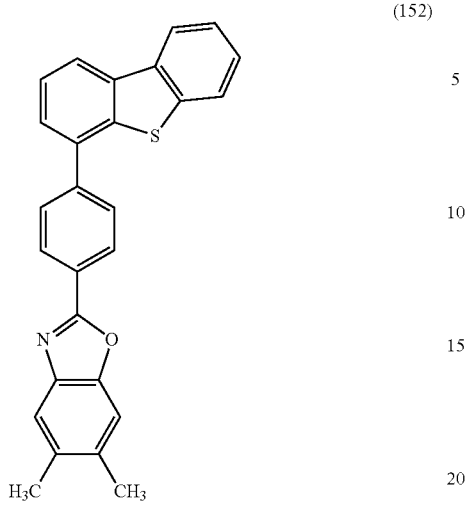
(153) 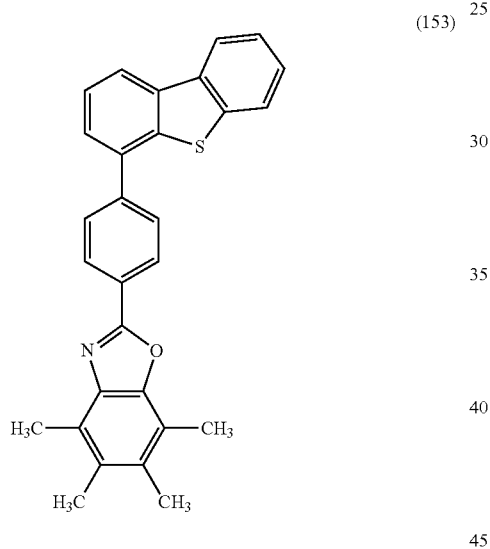
(154) 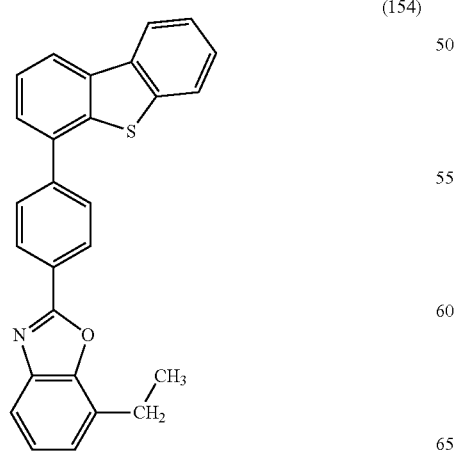
(155) 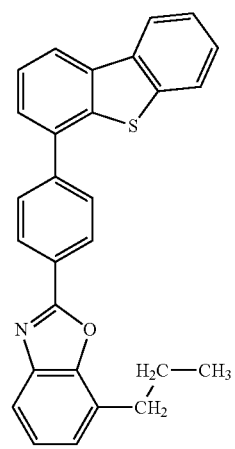
(156) 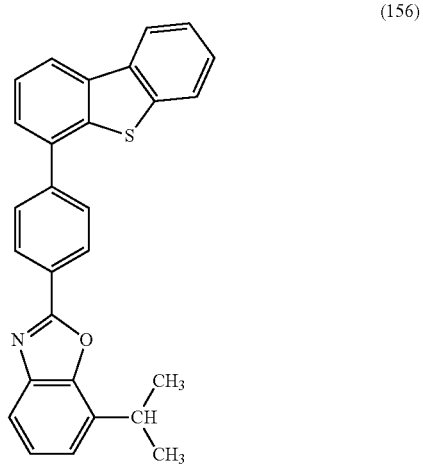
(157) 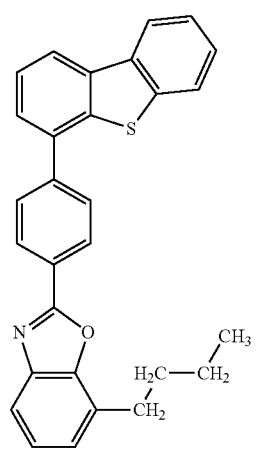

(158)
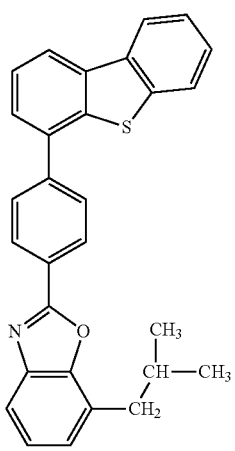
(159)
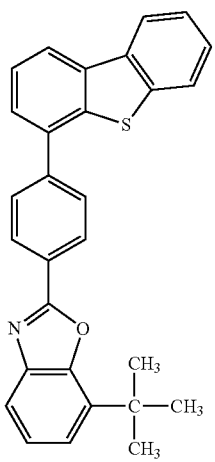
(160)
(161)
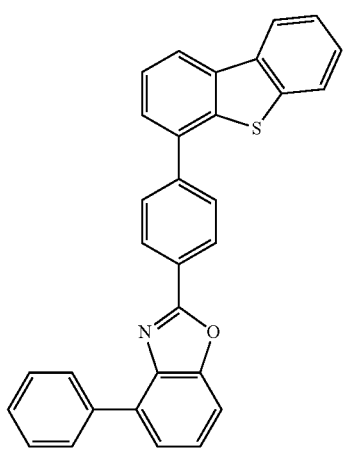
(162)
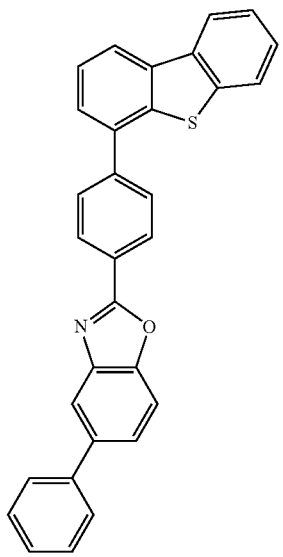
(163)
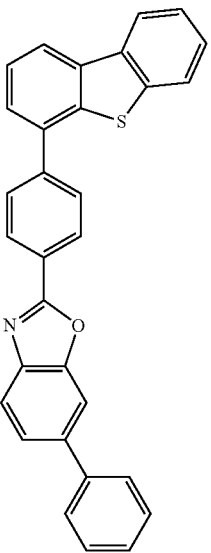

(164)
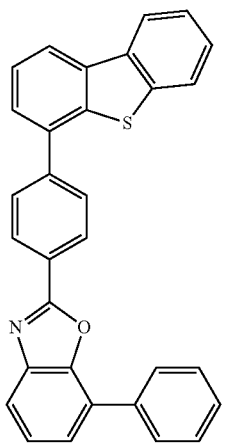
(165)
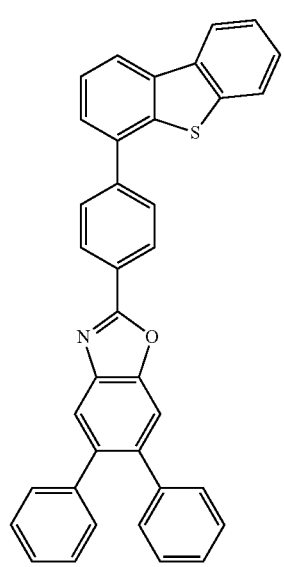
(166)
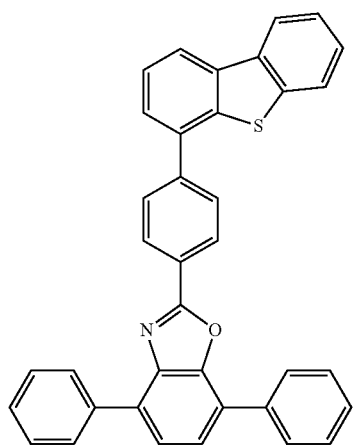
(167)
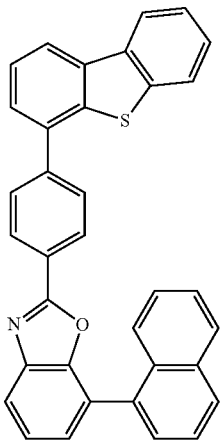
(168)
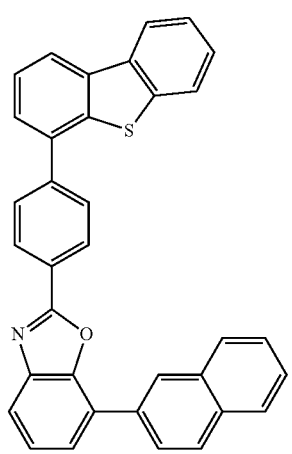
(169)
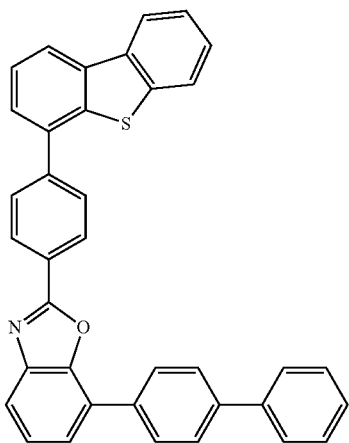

(170)
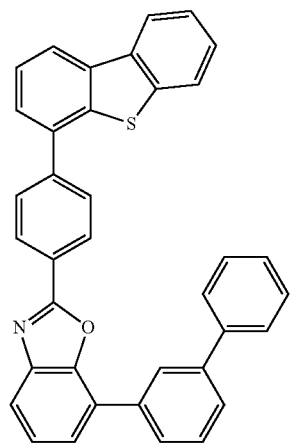
(171)
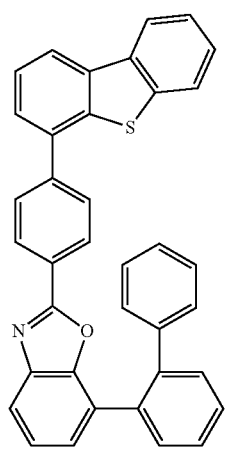
(172)
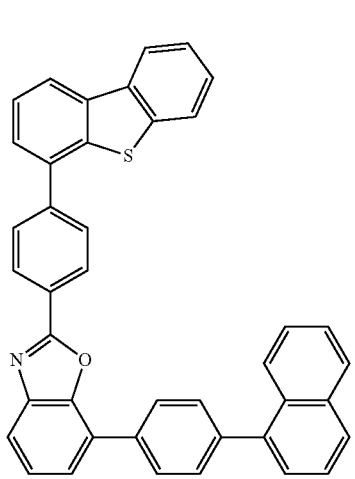
(173)
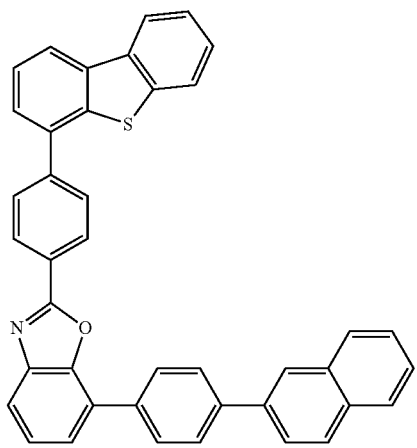
(174)
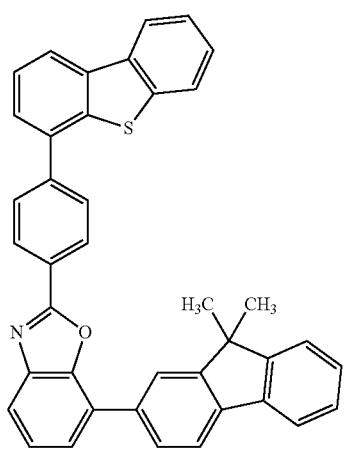
(175)
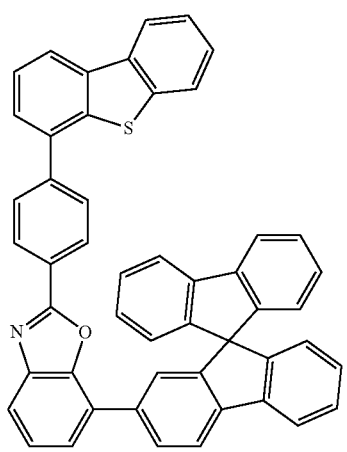

(176)
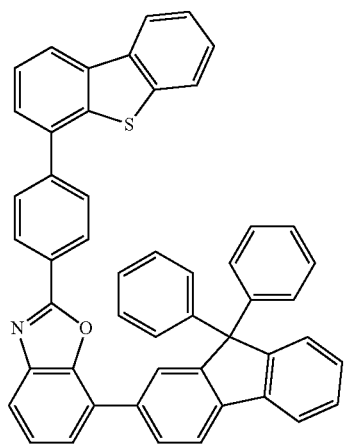
(177)
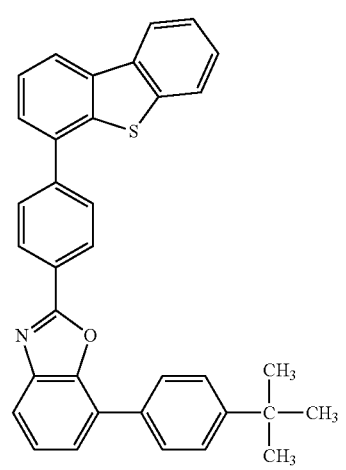
(178)
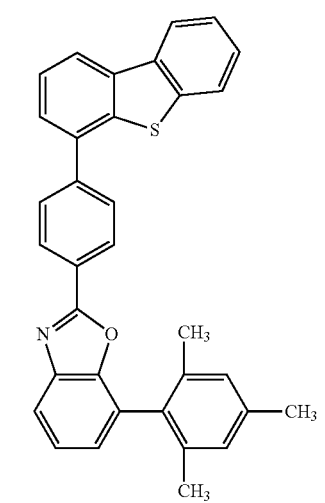
(179)
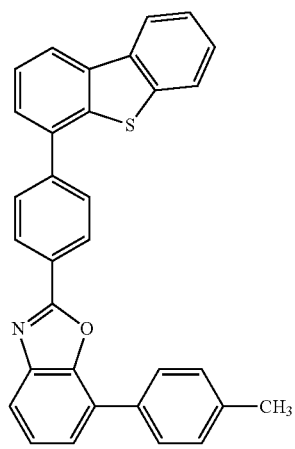
(200)
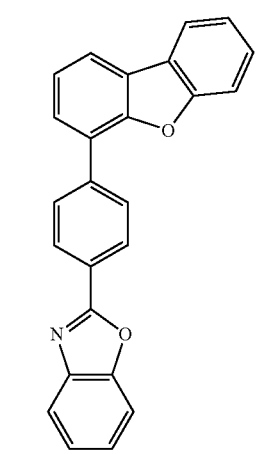
(201)
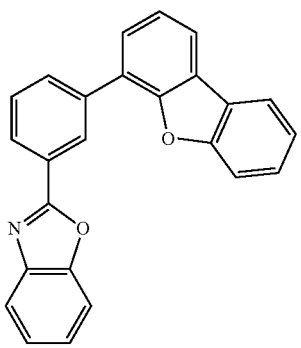
(202)
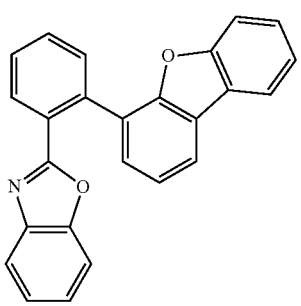

(203)
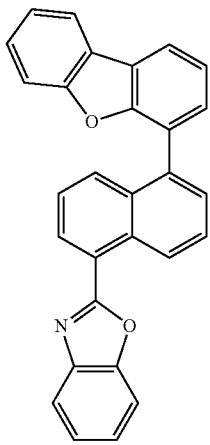
(204)
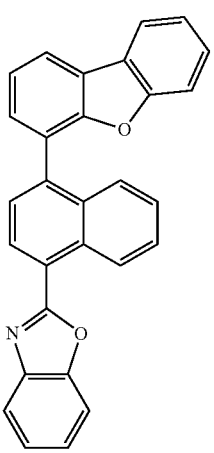
(205)
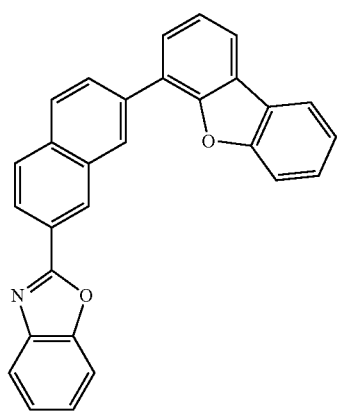
(206)
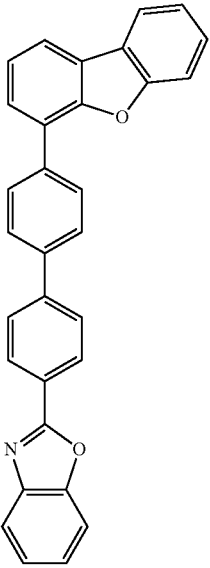
(207)
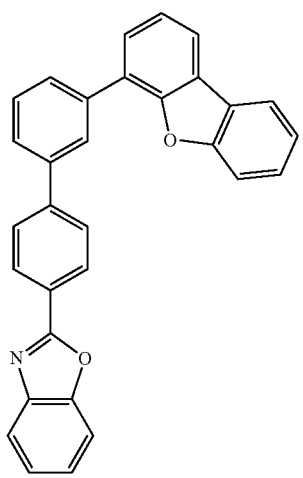
(208)
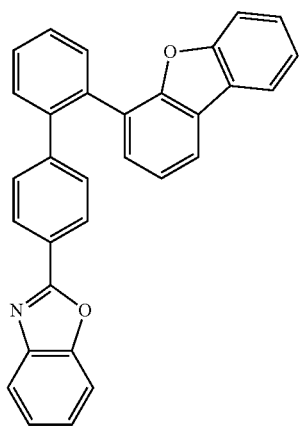

(209)
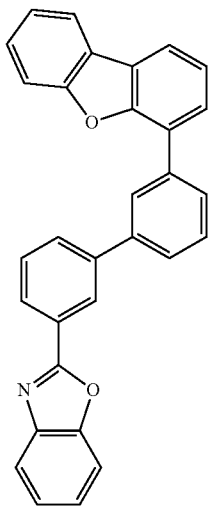
(210)
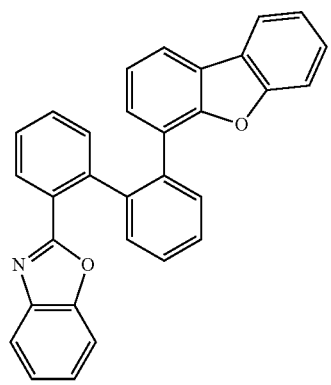
(211)
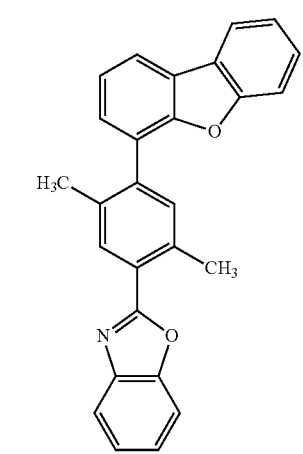
(212)
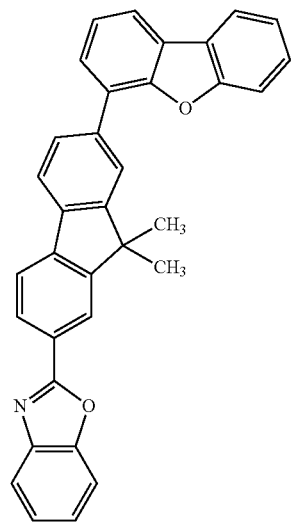
(213)
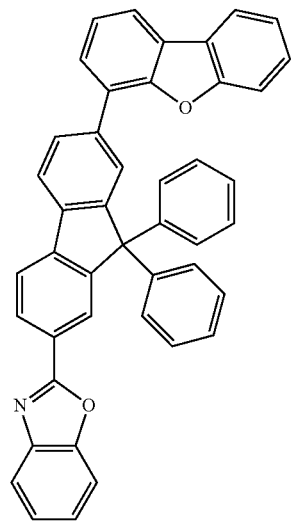
(214)
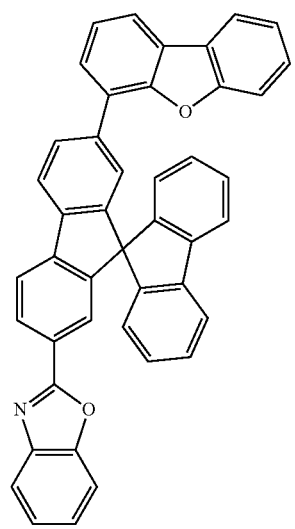

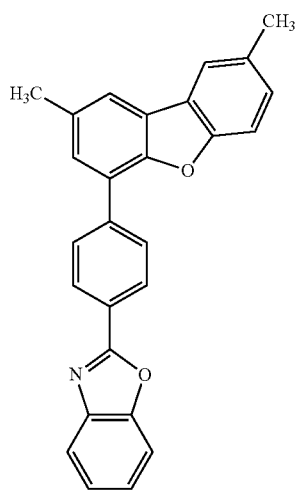
(215)
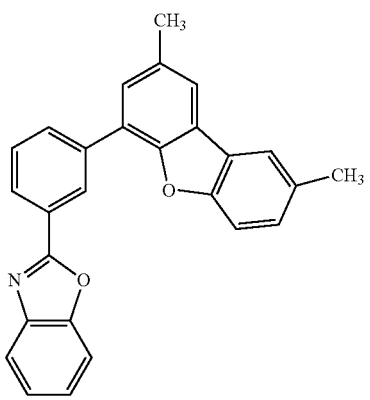
(218)
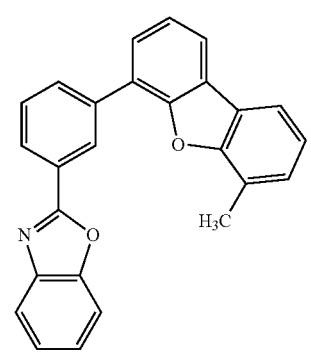
(219)
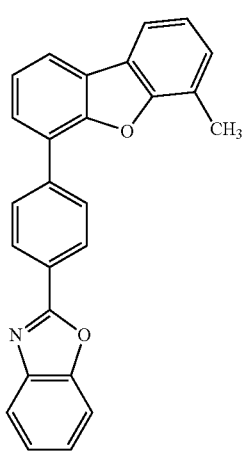
(216)
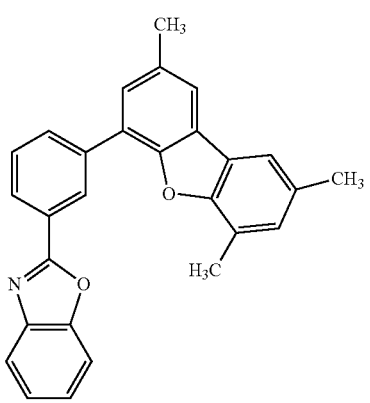
(220)
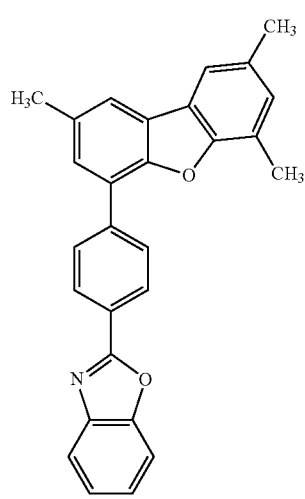
(217)
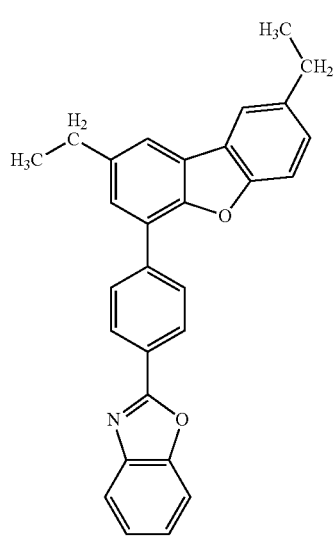
(221)

-continued
(222)
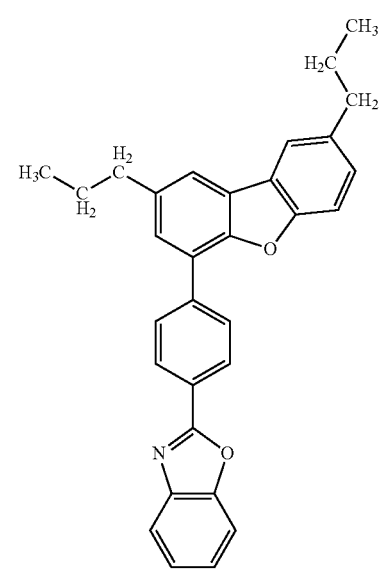
(223)
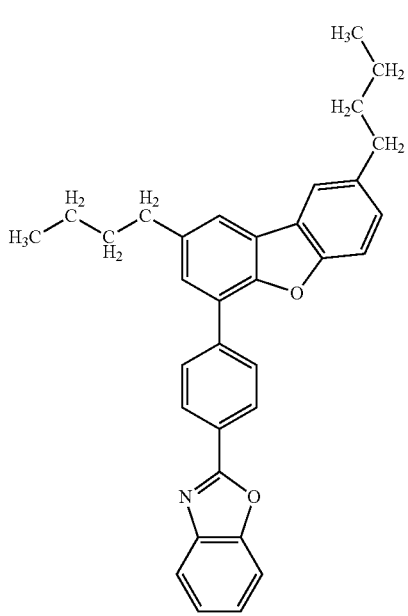
(224)
(225)
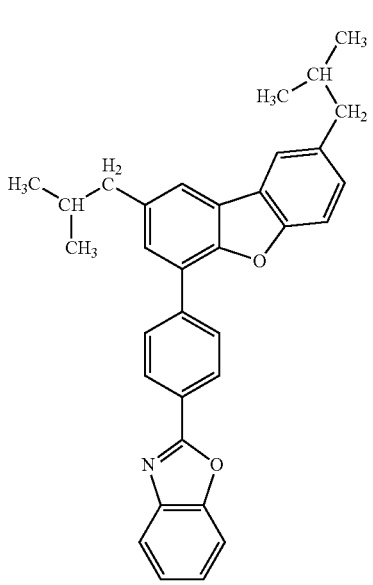
(226)
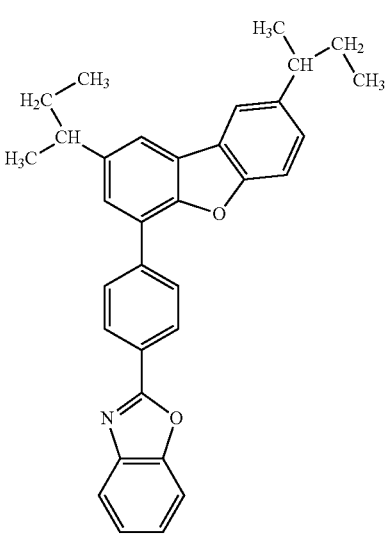
(227)
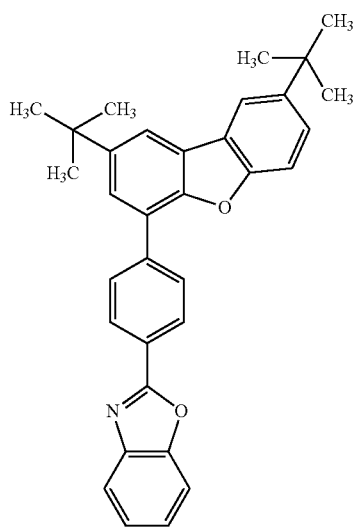

(228)
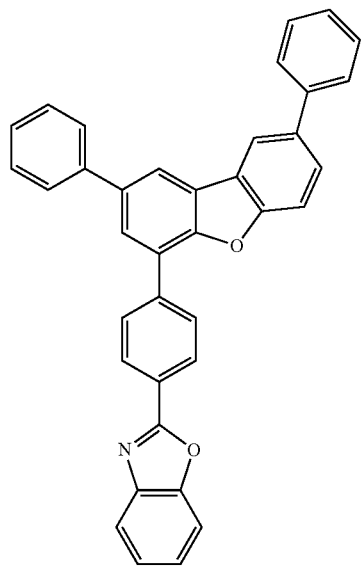
(229)
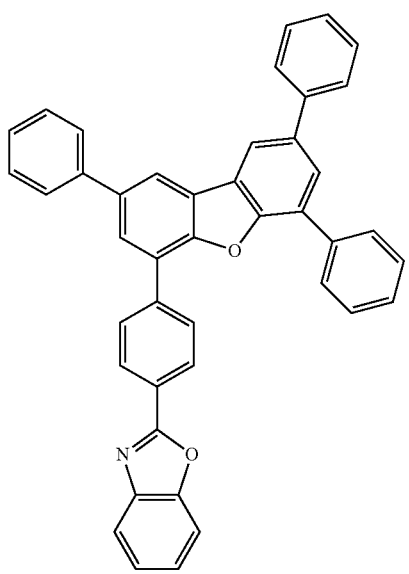
(230)
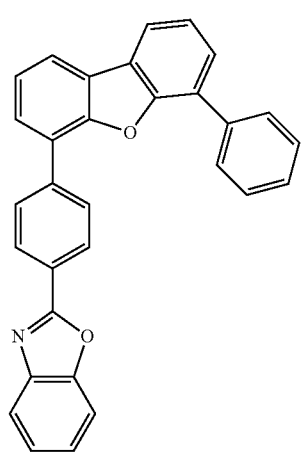
(231)
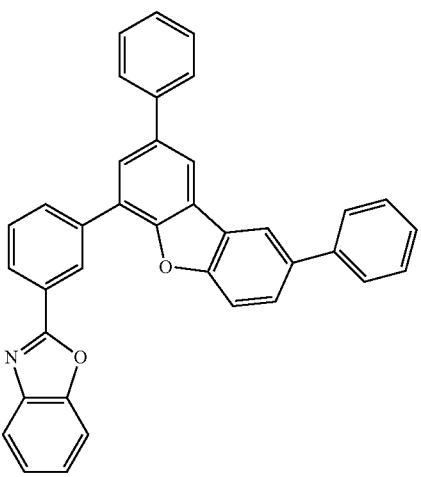
(232)
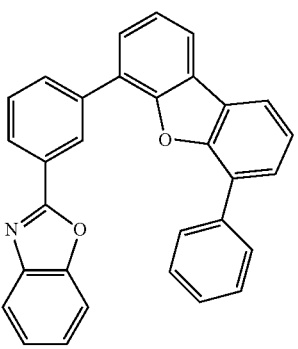
(233)
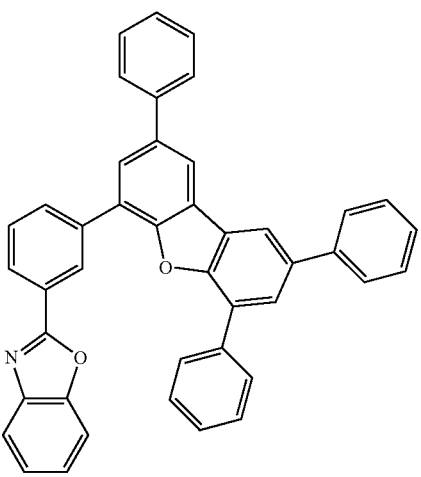

(234)
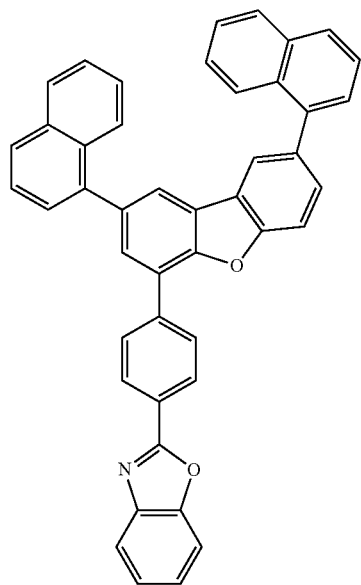
(236)
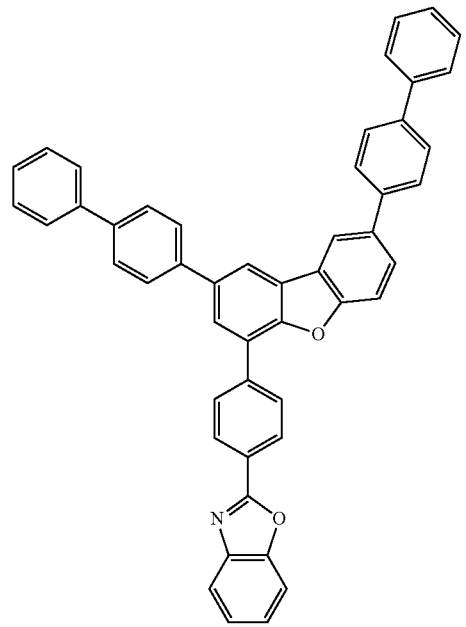
(235)
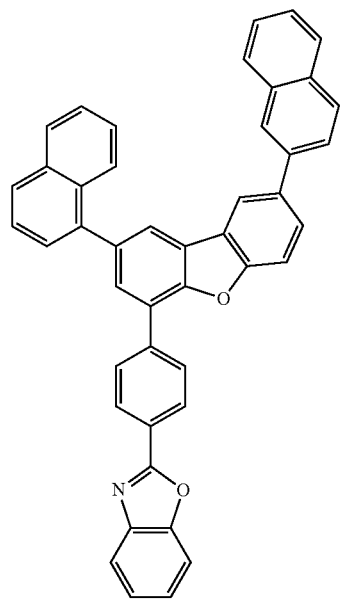
(237)
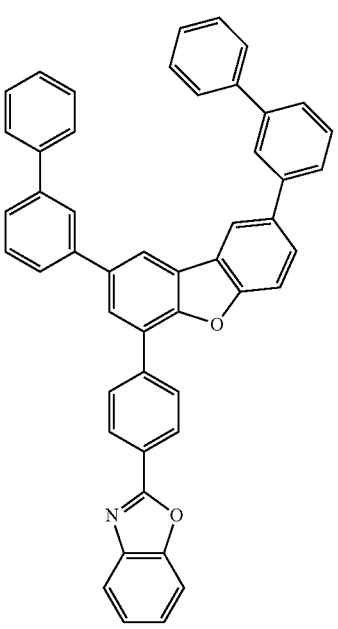

(238)
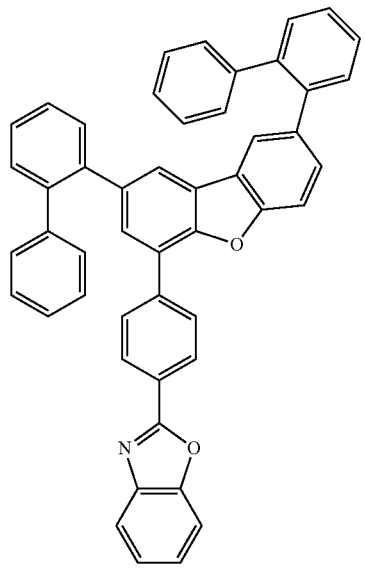
(240)
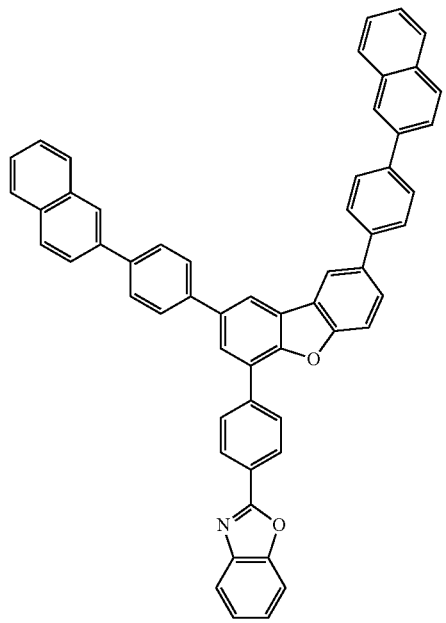
(239)
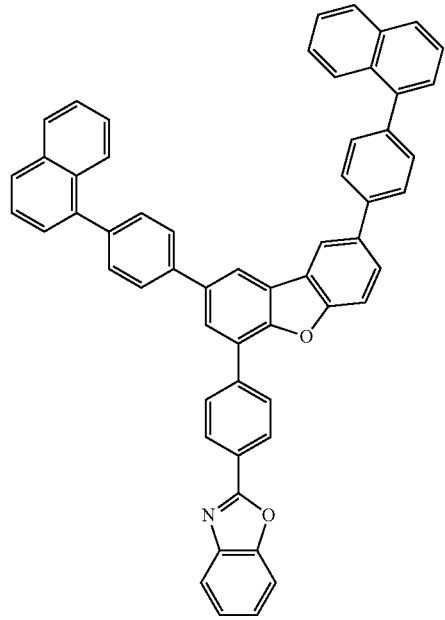
(241)
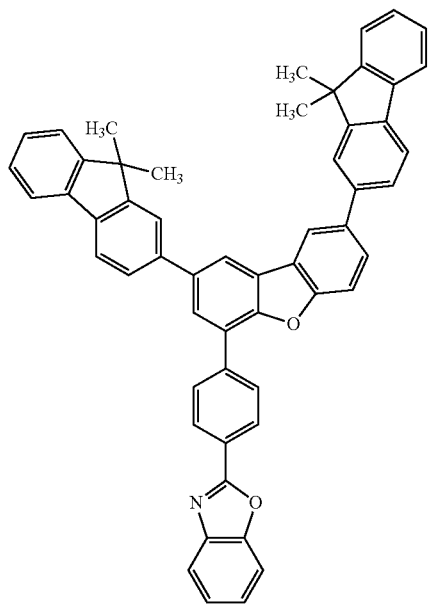

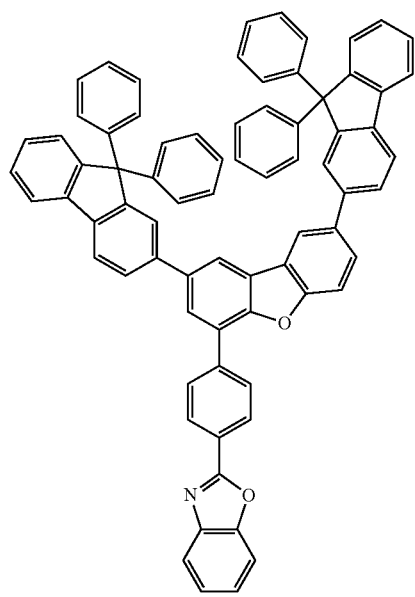
(242)
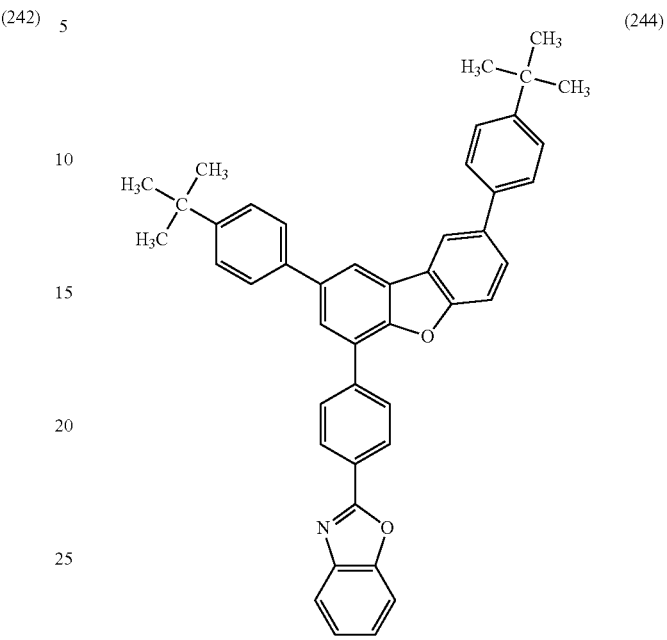
(244)
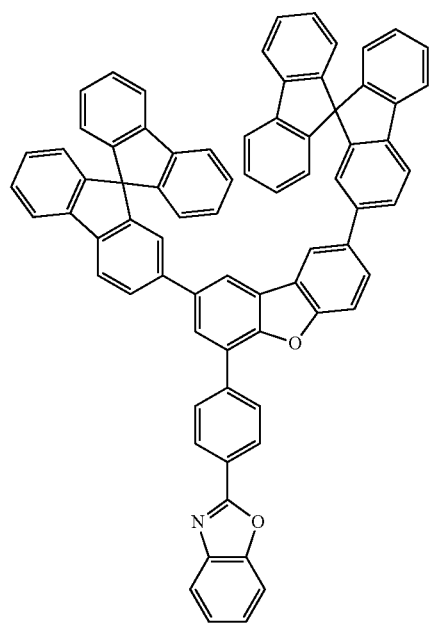
(243)
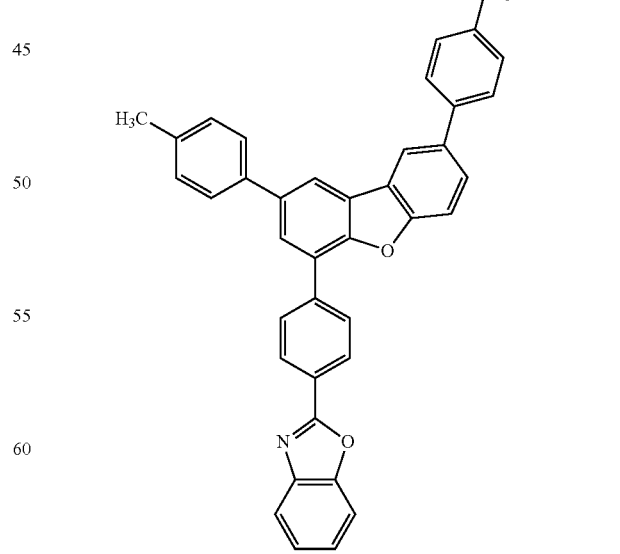
(245)

(246)
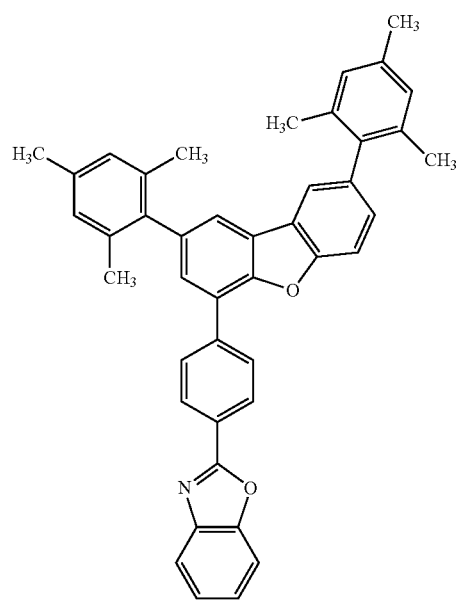
(247)
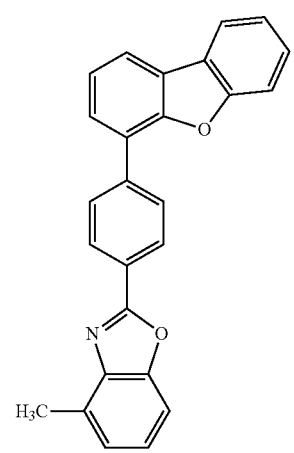
(248)
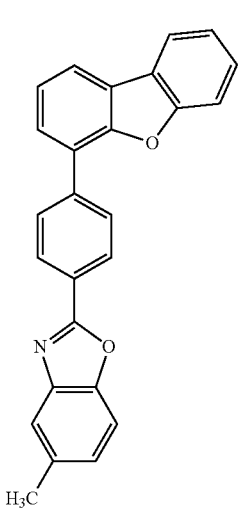
(249)
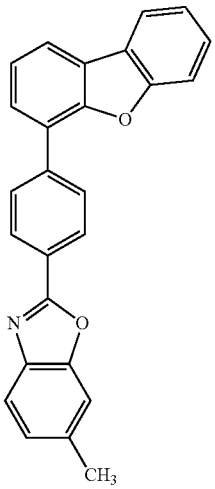
(250)
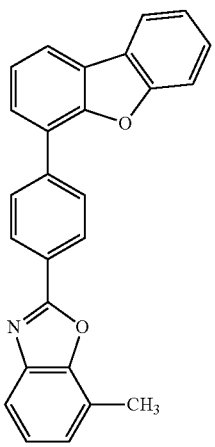
(251)
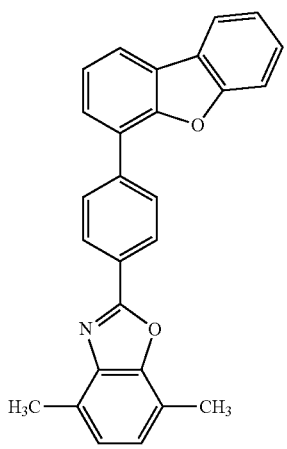

(252)
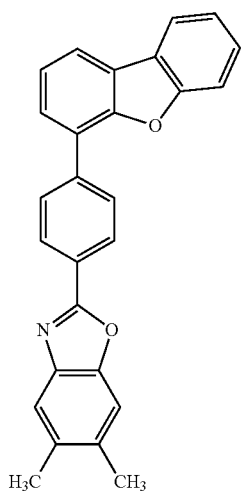
(253)
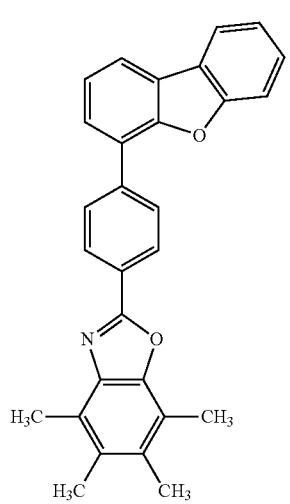
(254)
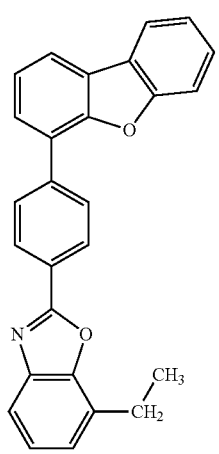
(255)
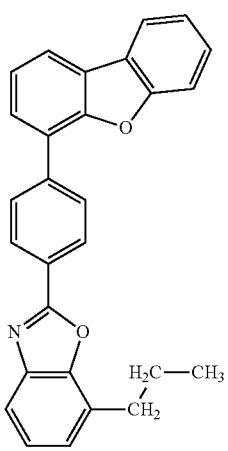
(256)
(257)
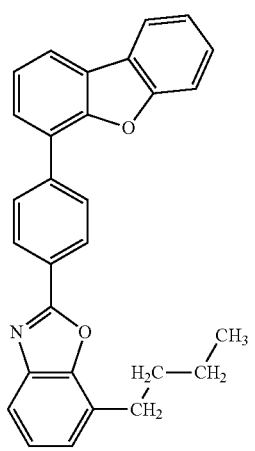

(258)
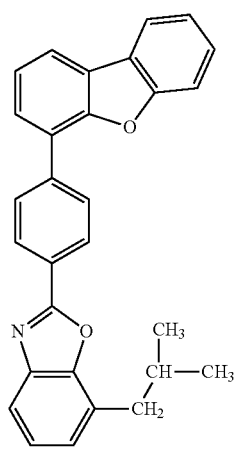
(259)
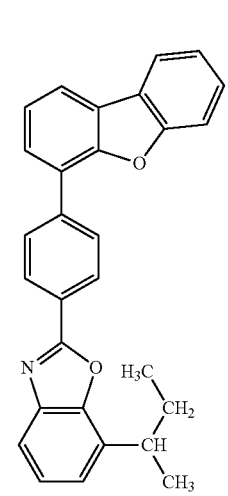
(260)
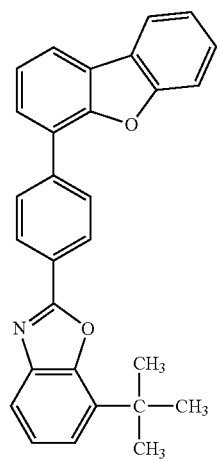
(261)
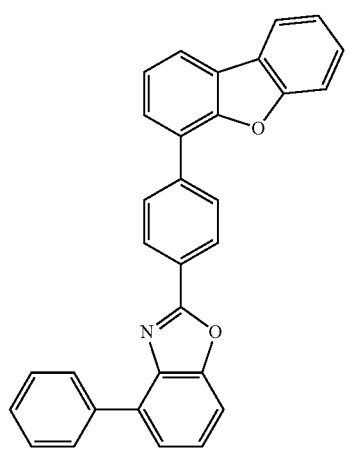
(262)
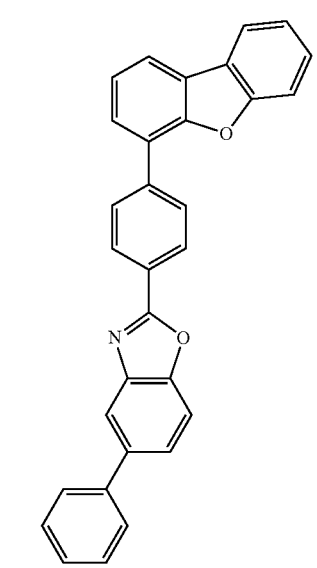
(263)
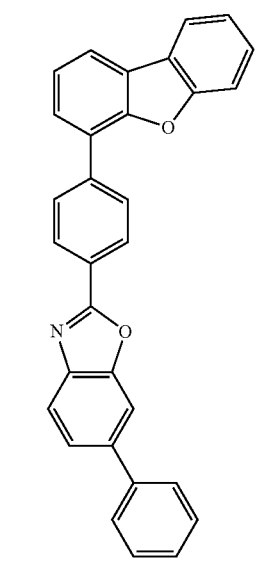

(264)
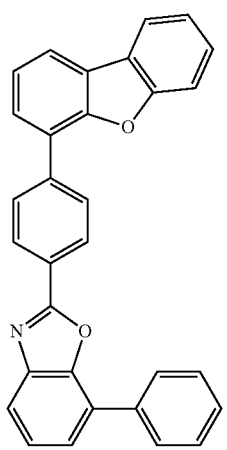
(265)
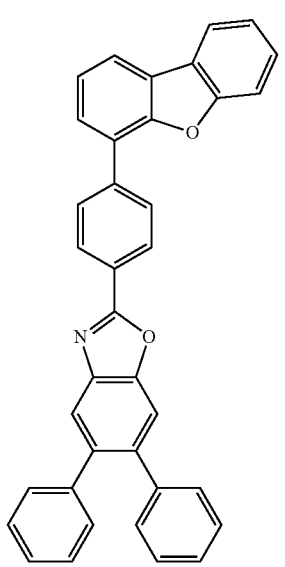
(266)
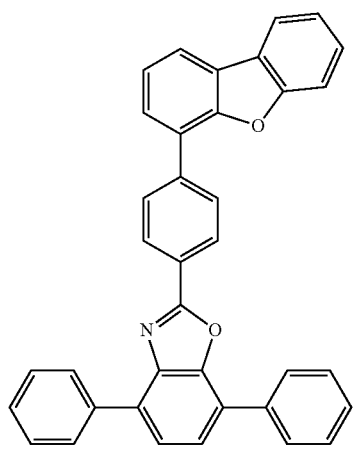
(267)
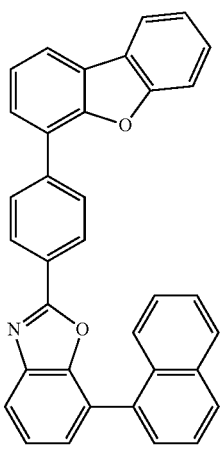
(268)
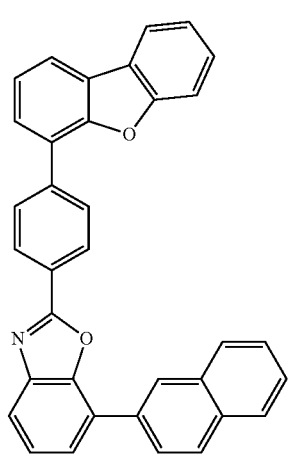
(269)
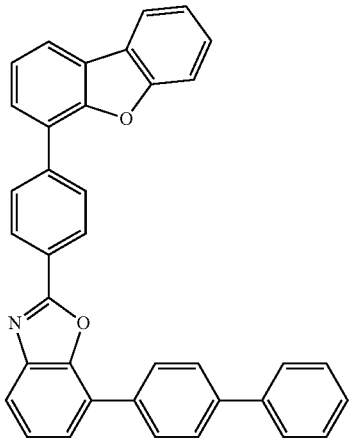

(270) 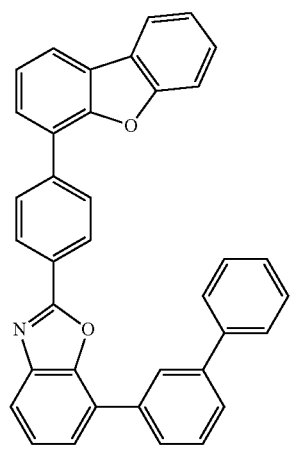
(273) 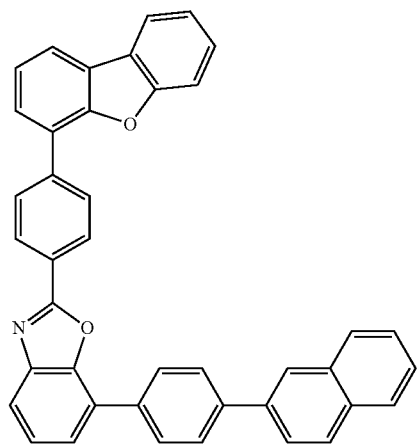
(271) 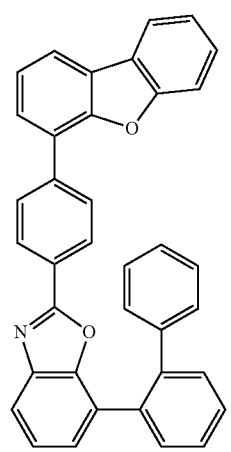
(274) 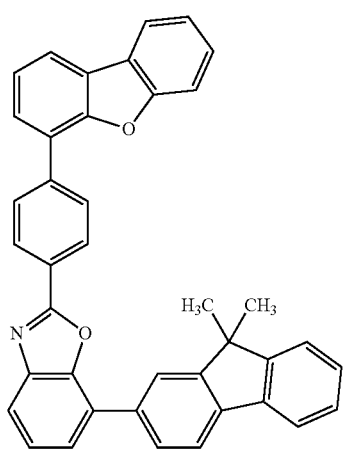
(272) 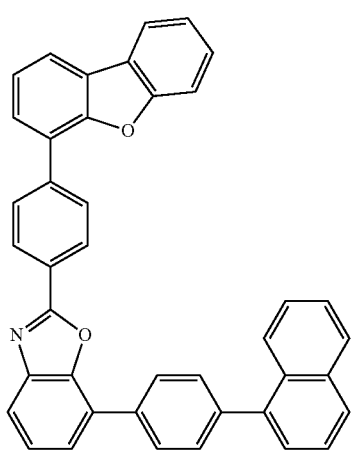
(275) 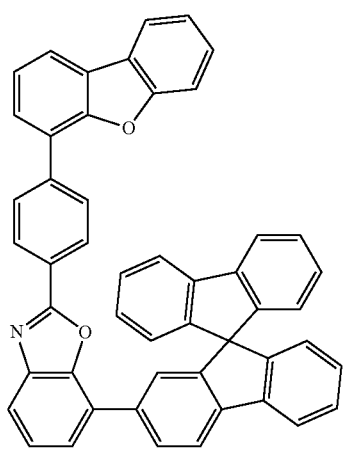

(276)

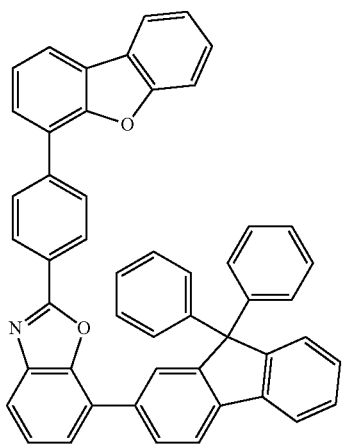

(277)

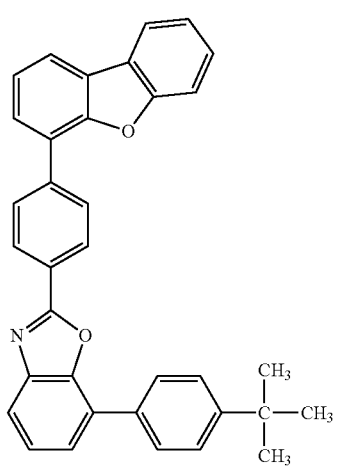

(278)

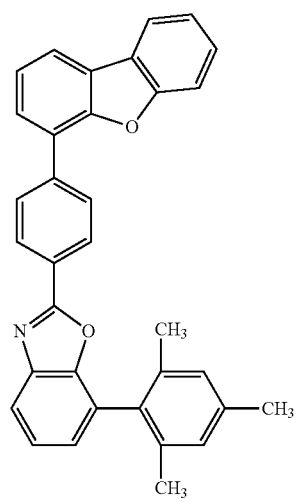

(279)

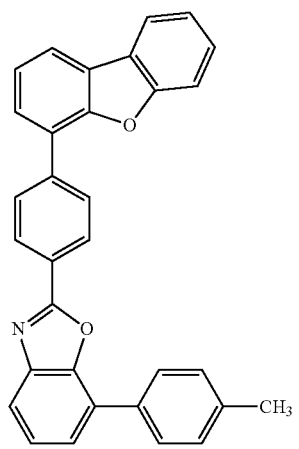

A variety of reactions can be used for a synthesis method of the benzoxazole derivative of this embodiment. For example, the benzoxazole derivative of one embodiment of the present invention which is represented by General Formula (G1) can be synthesized by a synthesis reaction in Synthesis Method 1.

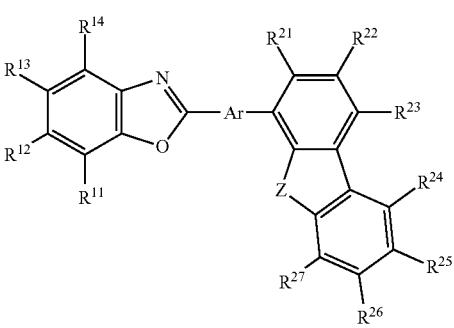

(G1)

<Synthesis Method 1>

As shown in Reaction Scheme (A-1), a halide of a benzoxazole derivative (a1) is coupled with an organoboron compound of a dibenzofuran derivative or a dibenzothiophene derivative or with a boronic acid of a dibenzofuran derivative or a dibenzothiophene derivative (a2) by the Suzuki-Miyaura Reaction, whereby the benzoxazole derivative (G1) which is the substance to be produced is synthesized. Note that in Reaction Scheme (A-1), $R^{30}$ and $R^{31}$ separately represent either hydrogen or an alkyl group having 1 to 6 carbon atoms. $R^{30}$ and $R^{31}$ may be bonded to each other to form a ring. Note that for the symbols ($R^{11}$ to $R^{14}$, $R^{21}$ to $R^{27}$, Ar, and Z), which are not explained here, the description of the general formula (G1) described above can be referred to.

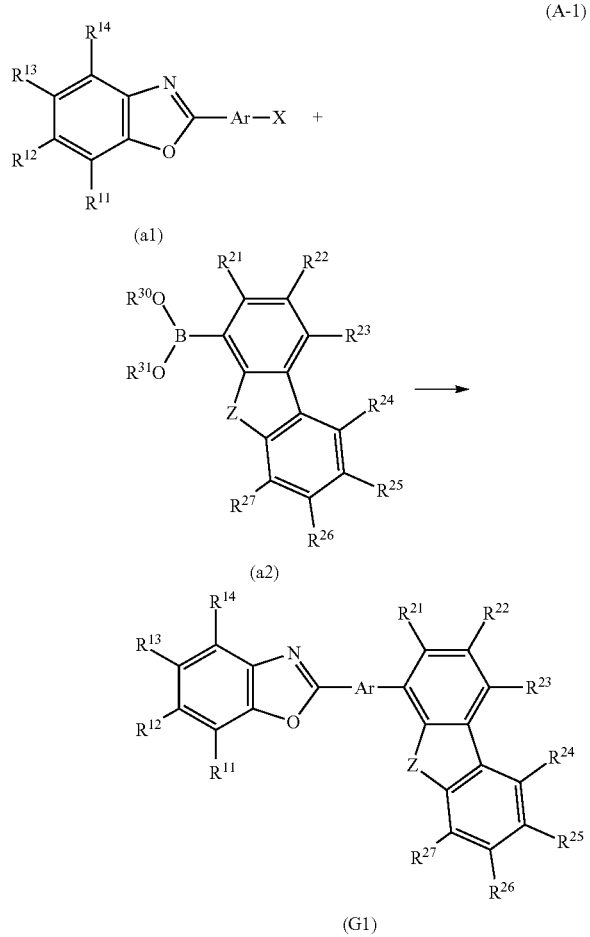

Further, X represents a halogen. The halogen is preferably bromine or iodine.

In the Suzuki-Miyaura coupling reaction in Reaction Scheme (A-1), a. palladium catalyst can be used as a metal catalyst. As the palladium catalyst, a mixture of a palladium complex and a ligand thereof can be used.

As the palladium catalyst, palladium(II) acetate, tetrakis(triphenylphosphine)palladium(0), bis(triphenylphosphine)palladium(II) dichloride, and the like can be used. Note that the palladium catalyst which can be used is not limited thereto.

As the ligand of the palladium catalyst, tri(ortho-tolyl)phosphine, triphenylphosphine, tricyclohexylphosphine, and the like can be used. Note that the ligand of the palladium catalyst which can be used is not limited thereto.

As a base, an organic base such as sodium tert-butoxide, an inorganic base such as potassium carbonate or sodium carbonate, and the like can be used. Note that the base which can be used is not limited thereto.

This reaction is preferably performed in a solution, and as a solvent, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like can be used. However, the solvent which can be used is not limited thereto. Note that a mixed solvent of toluene and water; a mixed solvent of toluene, ethanol, and water; or a mixed solvent of water and ether such as ethylene glycol dimethyl ether is more preferable.

Further, a triflate group or the like may be used other than the halogen represented in (a1) in the Suzuki-Miyaura coupling reaction which is shown in Reaction Scheme (A-1). However, the present invention is not limited thereto. Further, as a coupling reaction shown in Reaction Scheme (A-1), the Suzuki-Miyaura Reaction using the organoboron compound or the boronic acid represented by (a2) may be replaced with a cross coupling reaction using an organoaluminum compound, an organozirconium compound, an organozinc compound, an organotin compound, or the like. However, the present invention is not limited thereto.

Note that in Reaction Scheme (A-1), a case is shown in which the compound (a1) that has a halide or a triflate group as a substituent is reacted with the compound (a2) that is an organoboron compound or a boronic acid. However, the benzoxazole derivative represented by General Formula (G1) can be obtained also by performing coupling where the compound (a1) is an organoboron compound or a boronic acid and the compound (a2) has a halide or a triflate group as a substituent (i.e., where the halide or the compound having a triflate group as a substituent and the organoboron compound or boronic acid are interchanged with each other).

The benzoxazole derivative described in this embodiment is a substance having high excitation energy. Thus, the benzoxazole derivative can be favorably used as a host material in which a red- to green-emissive phosphorescent guest material and a red- to blue-emissive fluorescent guest material are dispersed.

Embodiment 2

In this embodiment, a light-emitting element including the benzoxazole derivative described in Embodiment 1 as one embodiment of the present invention will be described with reference to FIGS. 1A and 1B.

In the light-emitting element of this embodiment, an EL layer including at least a light-emitting layer is interposed between a pair of electrodes. The EL layer may have a plurality of layers in addition to the light-emitting layer. The plurality of layers have a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. The plurality of layers may include, for example, a hole-injection layer, a hole-transport layer, an electron-transport layer, an electron-injection layer, and the like.

In the light-emitting element of this embodiment illustrated in FIG. 1A, an EL layer 102 is provided between a pair of electrodes, a first electrode 101 and a second electrode 103. The EL layer 102 includes a hole-injection layer 111, a hole-transport layer 112, a light-emitting layer 113, an electron-transport layer 114, and an electron-injection layer 115. Note that in the light-emitting element described in this embodiment, the first electrode 101 provided over a substrate 100 functions as an anode and the second electrode 103 functions as a cathode.

The substrate 100 is used as a support of the light-emitting element. For example, glass, quartz, plastic, or the like can be used for the substrate 100. A flexible substrate may be used. A flexible substrate is a substrate that can be bent (is flexible); examples of the flexible substrate include a plastic substrate made of a polycarbonate, a polyarylate, or a polyethersulfone, and the like. A film (made of polypropylene, a polyester, poly(vinyl fluoride), poly(vinyl chloride), or the like), an inorganic film formed by evaporation, or the like can be used. Note that materials other than these can be used as long as they can function as a support of the light-emitting element in a manufacturing process of the light-emitting element.

For the first electrode 101, a metal, an alloy, an electrically conductive compound, a mixture thereof, or the like which has a high work function (specifically, a work function of 4.0 eV or more) is preferably used. Specifically, for example, indium tin oxide (ITO), indium tin oxide containing silicon or silicon oxide, indium zinc oxide (IZO), indium oxide containing tungsten oxide and zinc oxide (IWZO), and the like are given. Although films of these conductive metal oxides are usually formed by a sputtering method, a sol-gel method or the like may be used. For example, indium zinc oxide (IZO) can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1.5 wt %. Other examples include gold, platinum, nickel, tungsten, chromium, molybdenum, iron, cobalt, copper, palladium, nitrides of metal materials (e.g., titanium nitride), and the like.

Note that, in the EL layer 102, when a layer in contact with the first electrode 101 is formed using a composite material in which an organic compound and an electron acceptor (acceptor) which are described later are mixed, the first electrode 101 can be formed using any of a variety of metals, alloys, and electrically conductive compounds, a mixture thereof, and the like regardless of the work function. For example, aluminum, silver, an alloy containing aluminum (e.g., Al—Si), or the like can be used.

The EL layer 102 found over the first electrode 101 contains the benzoxazole derivative of one embodiment of the present invention. For part of the EL layer 102, a known substance can be used, and either a low molecular compound or a high molecular compound can be used. Note that the substance used for forming the EL layer 102 may have not only a structure formed of only an organic compound but also a structure partly including an inorganic compound.

The hole-injection layer 111 is a layer that contains a substance having a high hole-injection property. As the substance having a high hole-injection property, for example, metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

The following aromatic amine compounds which are low molecular organic compounds can be used: 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), or the like.

High molecular compounds (such as an oligomer, a dendrimer, or a polymer) can be used. As examples of the high molecular compound, the following are given: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl) methacrylamide] (abbreviation: PTPDMA), and poly[N,N'-bis(4-butylphenyl)-N,N'-bis(phenyl)benzidine] (abbreviation: Poly-TPD). A high molecular compound to which an acid is added, such as poly(3,4-ethylenedioxythiophene)/poly(styrenesulfonic acid) (abbreviation: PEDOT/PSS), or polyaniline/poly(styrenesulfonic acid) (abbreviation: PAni/PSS), can also be used.

A composite material in which an organic compound and an electron acceptor (acceptor) are mixed may be used for the hole-injection layer 111. Such a composite material is excellent in a hole-injection property and a hole-transport property because holes are generated in the organic compound by the electron acceptor. In this case, the organic compound is preferably a material excellent in transporting the generated holes (a substance having a high hole-transport property).

As the organic compound for the composite material, any of a variety of compounds such as aromatic amine compounds, carbazole derivatives, aromatic hydrocarbons, and high molecular compounds (e.g., oligomer, dendrimer, and polymer) can be used. The organic compound used for the composite material is preferably an organic compound having a high hole-transport property. Specifically, a substance having a hole mobility of $10^{-6}$ $cm^2/Vs$ or higher is preferably used. Note that any other substances may also be used as long as the hole-transport property thereof is higher than the electron-transport property thereof. The organic compounds that can be used for the composite material will be specifically given below.

Examples of the organic compound that can be used for the composite material include aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), and 4-phenyl-4'-(9-phenylfluoren-9-yl) triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl) anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, and the like.

Further alternatively, any of the following aromatic hydrocarbon compounds can be used: 2,3,6,7-tetramethyl-9,10-di (2-naphthyl)anthracene, 9,9'-bianthryl, 10,10'-diphenyl-9,9'-bianthryl, 10,10'-bis(2-phenylphenyl)-9,9'-bianthryl, 10,10'- bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As examples of the electron acceptor, organic compounds such as 7,7,8,8-tetracyano-2,3,5,6-tetrafluoroquinodimethane (abbreviation: $F_4$-TCNQ) and chloranil; and transition metal oxides can be given. Oxides of metals belonging to Groups 4 to 8 in the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is particularly preferable because it is stable in the air, has a low hygroscopic property, and is easily handled.

Note that the composite material may be fowled using the above-described electron acceptor and the above high molecular compound such as PVK, PVTPA, PTPDMA, or Poly-TPD and may be used for the hole-injection layer 111.

The hole-transport layer 112 is a layer that contains a substance having a high hole-transport property. As the substance with a high hole-transport property, low-molecular organic compounds such as aromatic amine compounds, examples of which are NPB, TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB), can be used. The substances given here are mainly ones that have a hole mobility of $10^{-6}$ cm$^2$/Vs or higher. Note that any other substances may also be used as long as the hole-transport property thereof is higher than the electron-transport property thereof. Note that the layer containing a substance having a high hole-transport property is not limited to a single layer and may be a stack of two or more layers containing any of the above substances.

Furthermore, for the hole-transport layer 112, a composite material in which an electron acceptor is contained in the above-mentioned substance having a high hole-transport property can be used.

Further, for the hole-transport layer 112, a high molecular compound such as PVK, PVTPA, PTPDMA, or Poly-TPD can be used.

The light-emitting layer 113 contains a light-emitting substance. For example, a fluorescent compound which emits fluorescence or a phosphorescent compound which emits phosphorescence can be used as the light-emitting substance. Therefore, in this embodiment, a case where the benzoxazole derivative of one embodiment of the present invention is used for the light-emitting layer is described. Note that for the light-emitting layer in which a substance (a guest material) having a high light-emitting property is dispersed in another substance (a host material), the benzoxazole derivative of one embodiment of the present invention can be used as the host material. Note that since the benzoxazole derivative of one embodiment of the present invention has high triplet excitation energy, the benzoxazole derivative can be favorably used as the host material.

In the case where the benzoxazole derivative of one embodiment of the present invention is used as the host material in the light-emitting layer and a substance emitting fluorescence is used as the guest material, it is preferable to use, as the guest material, a substance whose lowest unoccupied molecular orbital (LUMO) level is lower than that of the benzoxazole derivative and whose highest occupied molecular orbital (HOMO) level is higher than that of the benzoxazole derivative. For example, a material for blue light emission, a material for green light emission, a material for yellow light emission, and a material for red light emission are given. As examples of the material for blue light emission, the following are given: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. As examples of the material for green light emission, the following are given: N-(9,10-diphenyl-2-anthryl)-N,9-diphenyl-9H-carbazol-3-amine (abbreviation: 2P CAPA), N-[9,10-bis(1,1'-biphenyl-2-yl)-2-anthryl]-N,9-diphenyl-9H-carbazol-3-amine (abbreviation: 2PCABPIA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As examples of the material for yellow light emission, rubrene, 5,12-bis(1,1'-biphenyl-4-yl)-6,11-diphenyltetracene (abbreviation: BPT), and the like are given. As examples of the material for red light emission, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like are given.

As the phosphorescent compound that can be used for the light-emitting layer 113, a material for green light emission, a material for yellow light emission, a material for orange light emission, and a material for red light emission are given. As examples of the material for green light emission, the following are given: tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(1,2-diphenyl-1H-benzimidazolato)iridium(III) acetylacetonate (abbreviation: Ir(pbi)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), and the like. As examples of the material for yellow light emission, the following are given: bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), (acetylacetonato)bis{2-(4-methoxyphenyl)-3,5-dimethylpyrazinato}iridium(III) (abbreviation: Ir(dm moppr)$_2$ (acac)), and the like. As examples of the material for orange light emission, the following are given: tris(2-phenylquinolinato-N,C$^{2'}$)iridium(III) (abbreviation: Ir(pq)$_3$), bis(2-phenylquinolinato-N,C$^{2'}$)iridium(III) acetylacetonate (abbreviation: Ir(pq)$_2$(acac)), (acetylacetonato)bis(3,5-dimethyl-2-phenylpyrazinato)iridium(III) (abbreviation: Ir(mppr-Me)$_2$(acac)), (acetylacetonato)bis(5-isopropyl-3-methyl-2-phenylpyrazinato)iridium(III) (abbreviation: Ir(mppr-iPr)$_2$(acac)), and the like. As examples of the material for red light emission, organometallic complexes such as bis[2-(2'-benzo[4,5-α]thienyl)pyridinato-N,C$^{3'}$)iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), (dipivaloylmethanato)bis(2,3,5-triphenylpyrazinato)iridium(III) (abbreviation: Ir(tppr)$_2$(dpm)), and 2,3,7,8,12,13,17,18-octaethyl-21H,23H-porphyrin)platinum(II) (abbreviation: PtOEP). In addition, rare-earth metal complexes, such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)), exhibit light emission from rare-earth metal ions (electron transition between different multiplicities), and thus can be used as phosphorescent compounds.

A high molecular compound can be used as the light-emitting substance. Specifically, a material for blue light emission, a material for green light emission, and a material for orange to red light emission are given. As examples of the material for blue light emission, the following are given: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. As examples of the material for green light emission, the following are given: poly(p-phenylenvinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], and the like. As examples of the material for orange to red light emission, the following are given: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The benzoxazole derivative of one embodiment of the present invention can be favorably used as the host material for the light-emitting layer 113. However, the host material is not limited to the benzoxazole derivative of one embodiment of the present invention, and a plurality of host materials can be used. That is, the benzoxazole derivative of one embodiment of the present invention and another host material may be mixed to be used, or may be stacked to be used. For example, in order to suppress crystallization, a substance such as rubrene which suppresses crystallization may be further added. In addition, NPB, tris(8-quinolinolato)aluminum (III) (abbreviation: Alq), or 4-phenyl-4'-(9-phenyl-9H-carbazol-3-yl)triphenylamine (PCBA1BP), may be further added in order to efficiently transfer energy to the guest material.

With a structure in which a guest material is dispersed in a host material, crystallization of the light-emitting layer 113 can be suppressed. In addition, concentration quenching due to an increase in the concentration of the guest material can be prevented.

The electron-transport layer 114 is a layer that contains a substance having a high electron-transport property. Examples of the substance having a high electron-transport property include a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). A metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can also be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones that have an electron mobility of $10^{-6}$ cm$^2$/Vs or higher. Note that the electron-transport layer is not limited to a single layer and may be a stack of two or more layers containing any of the above substances.

Since the benzoxazole derivative of one embodiment of the present invention has an electron-transport property, the benzoxazole derivative can be used for the electron-transport layer.

The electron-injection layer 115 is a layer that contains a substance having a high electron-injection property. For the electron-injection layer 115, an element belonging to Group 1 or Group 2 of the periodic table or a compound thereof, such as lithium, cesium, calcium, lithium fluoride, cesium fluoride, calcium fluoride, or lithium oxide, can be used. A rare earth metal compound such as erbium fluoride can also be used. The substances given above for forming the electron-transport layer 114 can also be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the above-described substances for forming the electron-transport layer 114 (e.g., a metal complex or a heteroaromatic compound) can be used, for example. As the electron donor, a substance exhibiting an electron-donating property to the organic compound may be used. Specifically, it is preferable to use a rare earth metal or an element belonging to Group 1 or Group 2 of the periodic table, such as lithium, cesium, magnesium, or calcium. In addition, it is preferable to use an oxide of an element belonging to Group 1 or Group 2 of the periodic table, such as lithium oxide, calcium oxide, or barium oxide. A metal such as erbium or ytterbium, or a Lewis base such as magnesium oxide can also be used. An organic compound such as tetrathiafulvalene (abbreviation: TTF) can also be used.

Note that the hole-injection layer 111, the hole-transport layer 112, the light-emitting layer 113, the electron-transport layer 114, and the electron-injection layer 115 which are described above can each be formed by a method such as an evaporation method (e.g., a vacuum evaporation method), an ink-jet method, or a coating method.

When the second electrode 103 functions as a cathode, it can be formed using a metal, an alloy, an electrically conductive compound, a mixture thereof, or the like having a low work function (preferably, a work function of 3.8 eV or less). Specifically, any of the following can be used: aluminum or silver; an element belonging to Group 1 or Group 2 of the periodic table, that is, lithium, cesium, magnesium, calcium, or strontium; an alloy of the above metals (e.g., Mg—Ag or Al—Li); a rare earth metal such as europium or ytterbium; an alloy of the above metals; or the like.

Note that, in the case where in the EL layer 102, a layer formed in contact with the second electrode 103 is formed using a composite material in which the organic compound and the electron donor, which are described above, are mixed, a variety of conductive materials such as aluminum, silver, ITO, and indium tin oxide containing silicon or silicon oxide can be used regardless of the work function.

Note that the second electrode 103 can be formed by a vacuum evaporation method or a sputtering method. In the case of using a silver paste or the like, a coating method, an ink-jet method, or the like can be used.

In the above light-emitting element, current flows due to a potential difference applied between the first electrode 101 and the second electrode 103 and holes and electrons recombine in the EL layer 102, whereby light is emitted. Then, this emitted light is extracted through one or both of the first electrode 101 and the second electrode 103. Therefore, one or both of the first electrode 101 and the second electrode 103 is/are an electrode having a property of transmitting visible light.

Note that the structure of the layer provided between the first electrode 101 and the second electrode 103 is not limited to the above structure. A structure other than the above may also be employed as long as a light-emitting region in which holes and electrons recombine is provided in a region away from the first electrode 101 and the second electrode 103 in order to prevent quenching due to proximity of the light-emitting region to a metal.

In other words, a stacked structure of the layer is not particularly limited, and a layer formed of a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may be freely combined with a light-emitting layer.

Figure 1B:
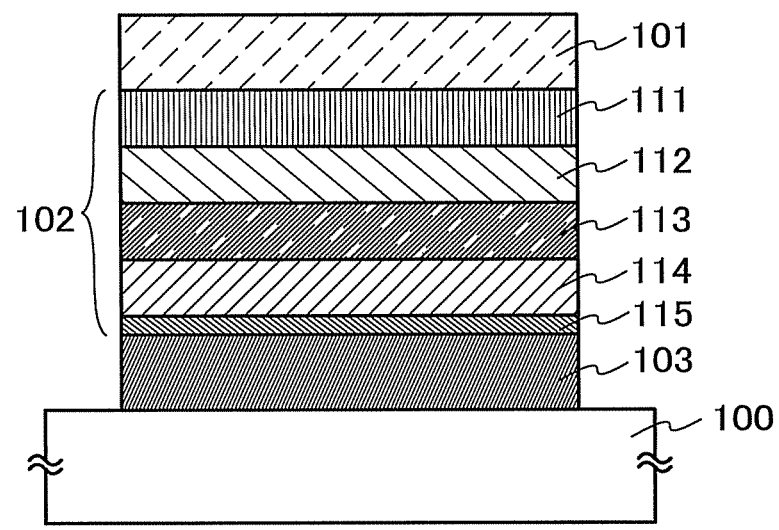

In a light-emitting element illustrated in FIG. 1B, the EL layer 102 is provided between the first electrode 101 and the second electrode 103 over the substrate 100. The EL layer 102 includes a hole-injection layer 111, a hole-transport layer 112, the light-emitting layer 113, an electron-transport layer 114, and an electron-injection layer 115. The light-emitting element in FIG. 1B includes: the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

A specific method for forming a light-emitting element will be described below.

The light-emitting element of this embodiment has a structure in which an EL layer is interposed between a pair of electrodes. The electrode (the first electrode or the second electrode) and the EL layer may be formed by a wet process such as a droplet discharging method (an ink-jet method), a spin coating method, or a printing method, or by a dry process such as a vacuum evaporation method, a CVD method, or a sputtering method. The use of a wet process enables formation at atmospheric pressure with a simple device and by a simple process, which gives effects of simplifying the process and improving productivity. In contrast, a dry process does not need dissolution of a material and enables use of a material that has low solubility in a solution, which expands the range of material choices.

All the thin films included in the light-emitting element may be formed by a wet process. In this case, the light-emitting element can be manufactured with only facilities needed for a wet process. Alternatively, formation of the stacked layers up to formation of the light-emitting layer may be performed by a wet process whereas functional layers such as the electron-transport layer, the first electrode, and the like which are stacked over the light-emitting layer may be formed by a dry process. Further alternatively, the second electrode and the functional layers may be foamed by a dry process before the formation of the light-emitting layer whereas the light-emitting layer, the functional layers stacked thereover, and the first electrode may be formed by a wet process. Needless to say, this embodiment is not limited to this, and the light-emitting element can be formed by appropriate selection from a wet process and a dry process depending on a material to be used, film thickness that is necessary, and the interface state.

In the above manner, the light-emitting element can be manufactured using the benzoxazole derivative of one embodiment of the present invention. According to one embodiment of the present invention, a light-emitting element with high current efficiency can be obtained.

Further, a light-emitting device (such as an image display device) using the light-emitting element of one embodiment of the present invention, which is manufactured as described above, can have low power consumption.

Note that with the use of the light-emitting element described in this embodiment, a planar light-emitting device, a passive matrix light-emitting device, or an active matrix light-emitting device in which driving of the light-emitting element is controlled by a thin film transistor (TFT) can be manufactured.

This embodiment can be implemented in appropriate combination with any of the other embodiments.

Embodiment 3

In this embodiment, a light-emitting element including a plurality of EL layers (such a light-emitting element is hereinafter referred to as a stacked-type element) will be described with reference to FIGS. 2A and 2B. This light-emitting element is a stacked-type light-emitting element including a plurality of EL layers between a first electrode 201 and a second electrode 203. Note that although the number of the EL layers is two or three in this embodiment, four or more EL layers may be included.

Figure 2A:
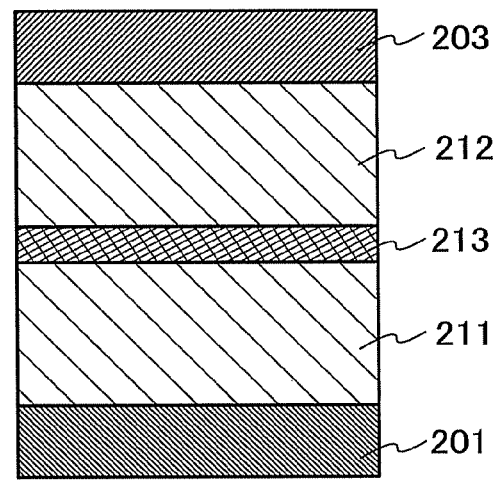
FIGS. 2A and 2B each illustrate a light-emitting element of one embodiment of the present invention.

In FIG. 2A, a first EL layer 211 and a second EL layer 212 are stacked between the first electrode 201 and the second electrode 203. In this embodiment, the first electrode 201 functions as an anode and the second electrode 203 functions as a cathode. Note that as the materials for the first electrode 201 and the second electrode 203, those described in Embodiment 2 can be used. Further, the first EL layer 211 and the second EL layer 212 may have the same or different structures. The first EL layer 211 and the second EL layer 212 may have the structure same as that in Embodiment 2, or either of the EL layers may have a structure different from that in Embodiment 2.

Further, a charge generation layer 213 is provided between the first EL layer 211 and the second EL layer 212. The charge generation layer 213 has a function of injecting electrons into one EL layer and injecting holes into the other EL layer when voltage is applied between the first electrode 201 and the second electrode 203. In this embodiment, when voltage is applied to the first electrode 201 so that the potential thereof is higher than that of the second electrode 203, the charge generation layer 213 injects electrons into the first EL layer 211 and injects holes into the second EL layer 212.

Note that the charge generation layer 213 preferably has a property of transmitting visible light in terms of light extraction efficiency. Further, the charge generation layer 213 functions even when it has lower conductivity than the first electrode 201 or the second electrode 203.

The charge generation layer 213 may have either a structure including an organic compound having a high hole-transport property and an electron acceptor or a structure including an organic compound having a high electron-transport property and an electron donor. Alternatively, both of these structures may be stacked. Note that the electron acceptor and the electron donor are at least capable of donating and accepting electrons with the assistance of an electric field.

In the case of a structure in which an electron acceptor and an organic compound having a high hole-transport property are included, as the organic compound having a high hole-transport property, aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like can be used. The substances given here are mainly ones that have a hole mobility of $10^{-6}$ cm$^2$/Vs or higher. However, substances other than the above substances may be used as long as they are organic compounds having a hole-transport property higher than an electron-transport property.

Further, as examples of the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. Oxides of metals belonging to Groups 4 to 8 in the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is particularly preferable because it is stable in the air, has a low hygroscopic property, and is easily handled.

In contrast, in the case of a structure in which an electron donor and an organic compound having a high electron-transport property are included, as the organic compound having a high electron-transport property, a metal complex having a quinoline skeleton or a benzoquinoline skeleton, such as Alq, Almq$_3$, BeBq$_2$, or BAN, or the like can be used, for example. A metal complex having an oxazole-based ligand or a thiazole-based ligand, such as Zn(BOX)$_2$ or Zn(BTZ)$_2$ can also be used. Other than the metal complexes, PBD, OXD-7, TAZ, BPhen, BCP, or the like can be used. The substances given here are mainly ones that have an electron mobility of $10^{-6}$ cm$^2$/Vs or higher. Note that substances other than the above substances may be used as long as they are organic compounds having an electron-transport property higher than a hole-transport property.

Further, as the electron donor, an element belonging to Group 1 or Group 2 of the periodic table, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that the charge generation layer 213 is formed using any of the above materials, whereby an unnecessary increase in driving voltage caused when the EL layers are stacked can be suppressed.

Figure 2B:
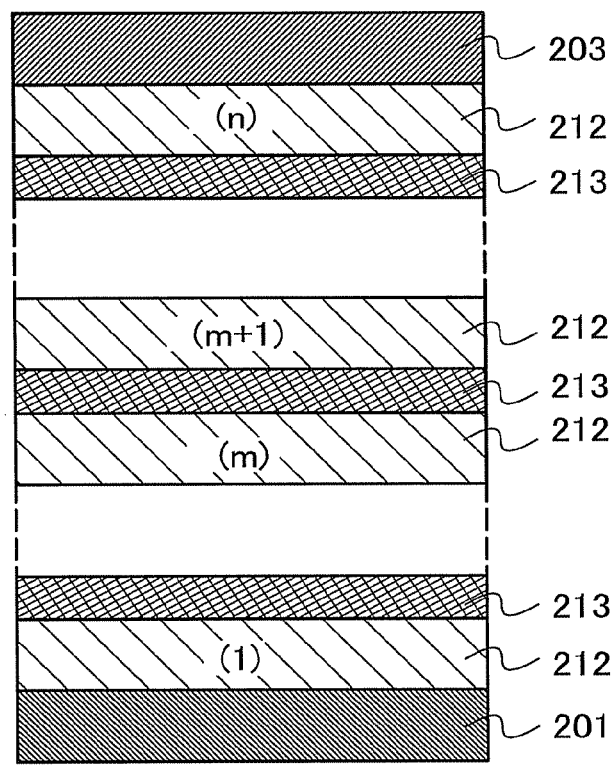

In FIG. 2A, the light-emitting element having two EL layers is described, and one embodiment of the present invention can be similarly applied to a light-emitting element having a stack of three or more EL layers as illustrated in FIG. 2B. A plurality of EL layers (the first to n$^{th}$ EL layers 212) which are partitioned by a charge generation layer 213 are arranged between a pair of electrodes as in the light-emitting element of this embodiment, whereby it is possible to obtain an element having long lifetime which can emit light with a high luminance while current density is kept low.

Further, the EL layers emit light having different colors from each other, thereby obtaining light emission of a desired color in the whole light-emitting element. For example, in the light-emitting element having two EL layers, when an emission color of the first EL layer and an emission color of the second EL layer are made to be complementary colors, it is possible to obtain a light-emitting element which emits white light as a whole light-emitting element. Note that "complementary colors" refer to colors that can produce an achromatic color when mixed. In sum, white light emission can be obtained by a mixture of lights from substances whose emission colors are complementary colors. Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that this embodiment can be combined with any of the other embodiments as appropriate.

Embodiment 4

In this embodiment, a light-emitting device which includes the light-emitting element of one embodiment of the present invention and can be used mainly for a lighting device is described with reference to FIGS. 3A to 3C. FIG. 3A is a top view illustrating a light-emitting device 300, and FIG. 3B is a cross-sectional view taken along a line A-B in FIG. 3A.

The light-emitting device 300 illustrated in FIGS. 3A and 3B includes, over a first substrate 301, a light-emitting element 308 including a first electrode 305, an EL layer 306, and a second electrode 307. The light-emitting element of one embodiment of the present invention is used as the light-emitting element 308.

As illustrated in FIG. 3B, a first terminal 303 is electrically connected to an auxiliary wiring 310 and a first electrode 305. A second terminal 304 is electrically connected to a second electrode 307. An insulating layer 309 is formed over an edge portion of the first electrode 305 and a projected portion of the first electrode 305, which is stacked over the auxiliary wiring 310. Note that although the first electrode 305 is formed over the auxiliary wiring 310 in FIG. 3B, the auxiliary wiring 310 may be formed over the first electrode 305.

The first substrate 301 and a second substrate 302 are bonded to each other with a sealant 312. A desiccant 311 is included between the first substrate 301 and the second substrate 302.

A light extraction structure 313a with minute unevenness is provided between the first electrode 305 with high refractive index and the first substrate 301 with lower refractive index, and a light extraction structure 313b with unevenness larger than that of the light extraction structure 313a is provided between the first substrate 301 and the air. Note that such a light extraction structure may be provided on both the upper and lower sides of the first substrate 301 as illustrated in FIG. 3B, or may be provided only on one side.

The light-emitting device illustrated in FIG. 3B has a so-called bottom emission structure in which light emitted from the light-emitting element 308 is extracted from the first electrode 305 side of the light-emitting element 308; however, a light-emitting device having a top emission structure in which light is extracted from the second electrode 307 side of the light-emitting element 308 as illustrated in FIG. 3C is also possible.

The light-emitting device 300 having a top emission structure includes, over the first substrate 301, a light-emitting element 308 including a first electrode 305, an EL layer 306, and a second electrode 307.

As illustrated in FIG. 3C, the first terminal 303 is electrically connected to the first electrode 305, and the second terminal 304 is electrically connected to the second electrode 307. Further, the insulating layer 309 is formed over the edge portion of the first electrode 305. The auxiliary wiring 310 is formed over the second electrode 307.

The first substrate 301 and the second substrate 302 are bonded to each other with the sealant 312. The desiccant 311 is included between the first substrate 301 and the second substrate 302. Note that it is preferable that the desiccant 311 be transparent or be provided so as not to overlap with an emission area defined as a region where the EL layer 306 simultaneously contacts with both the first electrode 305 and the second electrode 307.

The light extraction structure 313a is provided over the light-emitting element 308.

Note that although the light-emitting device 300 illustrated in FIG. 3A is octagonal, but the light-emitting device 300 may have a curve or a shape of a different polygon, preferably a triangle, a quadrangle, a hexagon, or the like. This is because the plurality of light-emitting device 300 can be provided in a limited area without a space therebetween in the case where the light-emitting device 300 is triangular, quadrangular, or hexagonal.

In the above manner, the light-emitting device including the light-emitting element of one embodiment of the present invention can be obtained. Note that the structure described in this embodiment can be combined as appropriate with any of the structures described in the other embodiments.

Embodiment 5

Figure 4A:
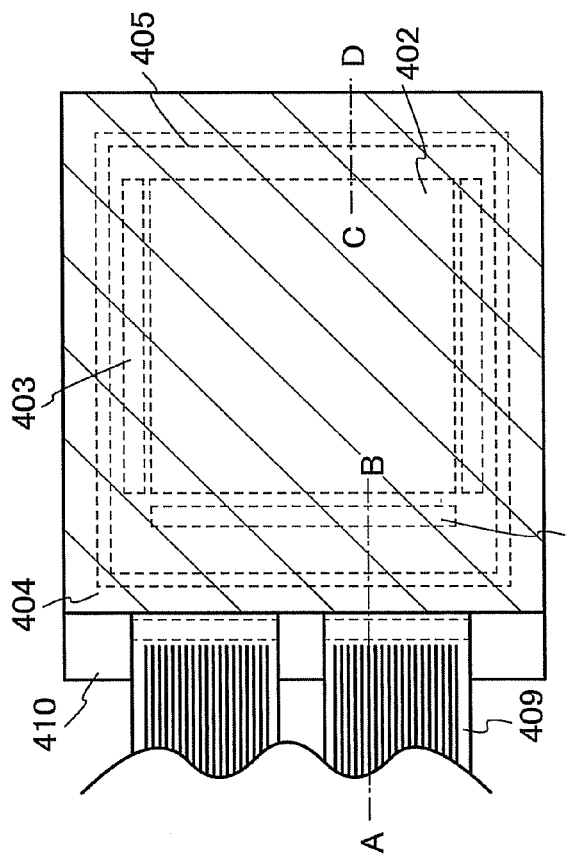
FIGS. 4A and 4B illustrate a light-emitting device of one embodiment of the present invention.
Figure 4B:
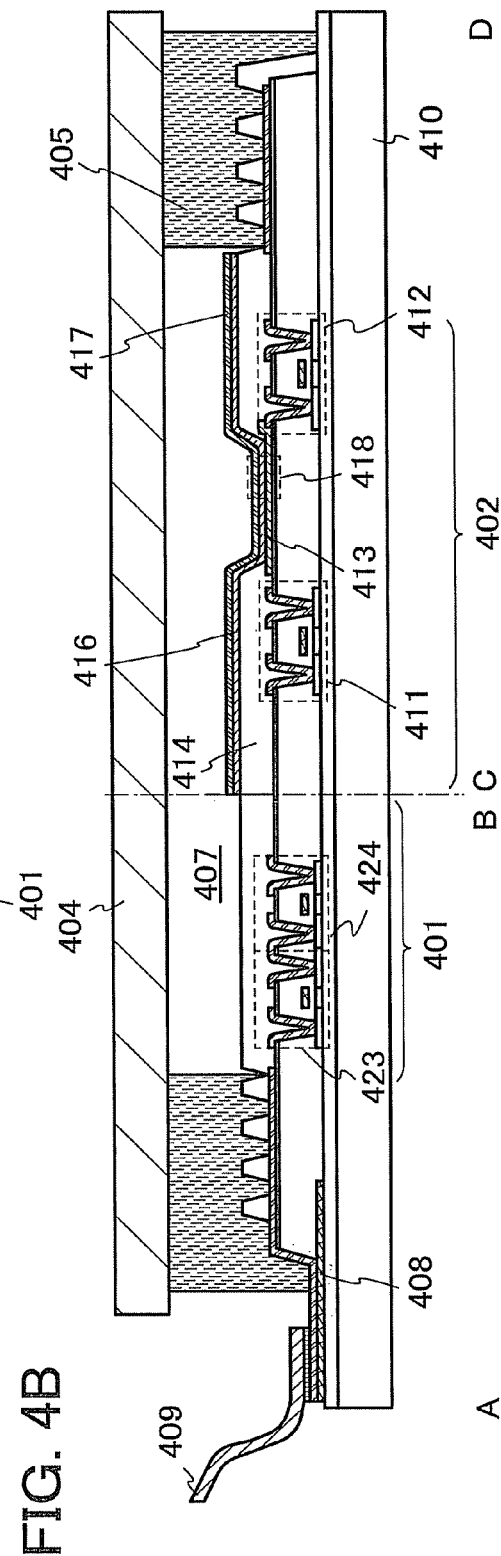

In this embodiment, a light-emitting device including the light-emitting element of one embodiment of the present invention will be described with reference to FIGS. 4A and 4B. FIG. 4A is a top view illustrating a light-emitting device. FIG. 4B is a cross-sectional view taken along lines A-B and C-D in FIG. 4A.

In FIG. 4A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space.

A lead wiring 408 in FIG. 4B is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure will be described with reference to FIG. 4B. The driver circuit portion and the pixel portion are formed over an element substrate 410. Here, the source side driver circuit 401 which is the driver circuit portion and one pixel in the pixel portion 402 are illustrated.

Note that as the source side driver circuit 401, a CMOS circuit, which is a combination of an n-channel TFT 423 and a p-channel TFT 424, is fowled. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the driver circuit can be formed outside the substrate.

The pixel portion 402 includes a plurality of pixels having a switching TFT 411, a current control TFT 412, and a first electrode 413 electrically connected to a drain of the current control TFT 412. An insulator 414 is formed to cover an end portion of the first electrode 413. Here, the insulator 414 is Ruined using a positive type photosensitive acrylic resin film.

In order to improve the coverage by the EL layer 416, the insulator 414 is provided such that either an upper end portion or a lower end portion of the insulator 414 has a curved surface with a curvature. For example, when positive type photosensitive acrylic resin is used as a material for the insulator 414, the insulator 414 preferably has a curved surface with a curvature radius of 0.2 μm to 3 μm only as the upper end. The insulator 414 can be formed using either a negative type photosensitive resin which becomes insoluble in an etchant by light irradiation or a positive type photosensitive resin which becomes soluble in an etchant by light irradiation.

An EL layer 416 and a second electrode 417 are formed over the first electrode 413 to result in a light-emitting element 418. Here, a material having a high work function is preferably used as a material for forming the first electrode 413 functioning as the anode. For example, it is possible to use a single layer of an ITO film, an indium tin oxide film that contains silicon, an indium oxide film that contains 2 wt % to 20 wt % of zinc oxide, a titanium nitride film, a chromium film, a tungsten film, a zinc film, a platinum film, or the like, a stacked layer of a titanium nitride film and a film that mainly contains aluminum, a three-layer structure of a titanium nitride film, a film that mainly contains aluminum and a titanium nitride film, or the like. Note that when a material which enables an ohmic contact with the EL layer 416 is used as the first electrode 413 and a low resistance material is used to connect the first electrode 413 with the current control TFT 412, an ohmic contact can be obtained and wiring resistance can be reduced.

The EL layer 416 is formed by any of a variety of methods such as an evaporation method using an evaporation mask, a droplet discharging method like an ink jet method, a printing method, and a spin coating method. The EL layer 416 contains the benzoxazole derivative described in Embodiment 1. Another material contained in the EL layer 416 may be a low molecular material, an oligomer, a dendrimer, a high molecular material, or the like.

As a material used for the second electrode 417 which is formed over the EL layer 416 and functions as the cathode, a material having a low work function (aluminum (Al), magnesium (Mg), lithium (Li), calcium (Ca), an alloy or a compound of those, e.g., magnesium-silver (Mg—Ag), magnesium-indium (Mg—In), aluminum-lithium (Al—Li), or the like) is preferably used. In order that light generated in the EL layer 416 be transmitted through the second electrode 417, the second electrode 417 may be formed of a stack of a metal thin film having a reduced thickness and a transparent conductive film (e.g., ITO, indium oxide containing 2 wt % to 20 wt % of zinc oxide, indium tin oxide that contains silicon or silicon oxide, or zinc oxide (ZnO)).

The sealing substrate 404 is attached to the element substrate 410 with the sealant 405, a space 407 enclosed by the element substrate 410, the sealing substrate 404, and the sealant 405 is foamed. Note that the space 407 may be filled with filler or an inert gas; the sealant 405 is used as the filler in some cases.

Note that an epoxy-based resin is preferably used as the sealant 405. As a material for the sealing substrate 404, a glass substrate, a quartz substrate, or a plastic substrate containing fiberglass-reinforced plastics (FRP), poly(vinyl fluoride) (PVF), a polyester, an acrylic resin, or the like can be used. It is desirable that materials transmit as little moisture or oxygen as possible.

In the above manner, the active matrix light-emitting device including the light-emitting element of one embodiment of the present invention can be obtained.

Figure 5A:
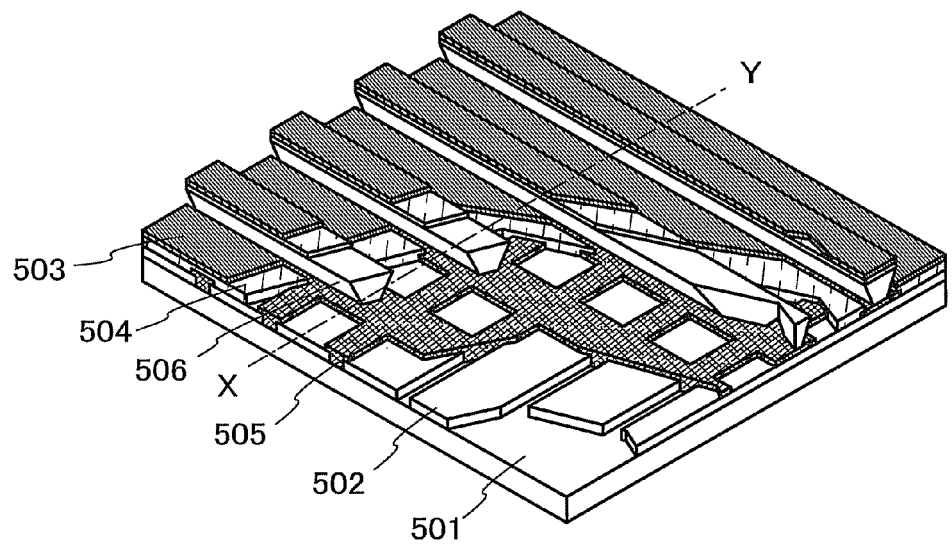
FIGS. 5A and 5B illustrate a light-emitting device of one embodiment of the present invention.
Figure 5B:
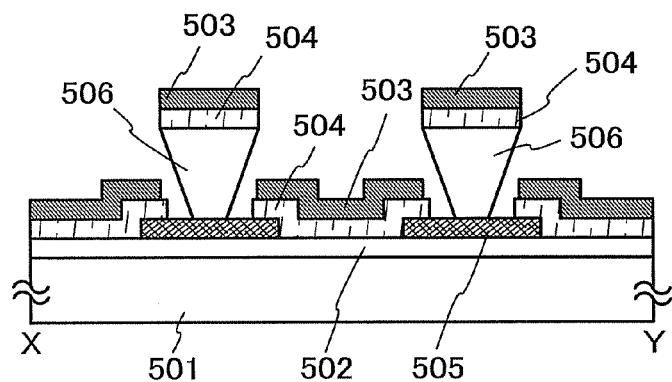

The light-emitting element of the present invention can be used for a passive matrix light-emitting device instead of the above active matrix light-emitting device. FIGS. 5A and 5B illustrate a perspective view and a cross-sectional view of a passive matrix light-emitting device including the light-emitting element of one embodiment of the present invention. FIG. 5A is a perspective view of the light-emitting device. FIG. 5B is a cross-sectional view taken along a line X-Y in FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the base (a side parallel to the plane of the insulating layer 505 and in contact with the insulating layer 505) is shorter than the upper side (a side parallel to the plane of the insulating layer 505 and not being in contact with the insulating layer 505. The partition layer 506 is provided in such a manner, whereby a defect of a light-emitting element due to crosstalk or the like can be prevented.

In the above manner, the passive matrix light-emitting device including the light-emitting element of one embodiment of the present invention can be obtained.

All the light-emitting devices described in this embodiment are formed using the light-emitting element of one embodiment of the present invention and thus can be light-emitting devices with lower power consumption.

Note that this embodiment can be combined with any of the other embodiments as appropriate.

Embodiment 6

In this embodiment, examples of a variety of electronic devices and lighting devices which are completed with the use of a light-emitting device that is one embodiment of the present invention will be described with reference to FIGS. 6A to 6D, FIG. 7, and FIG. 8.

Examples of the electronic device to which the light-emitting device is applied include television devices (also referred to as TV or television receivers), monitors for computers and the like, cameras such as digital cameras and digital video cameras, digital photo frames, mobile phones (also referred to as portable telephone devices), portable game machines, portable information terminals, audio reproducing devices, large game machines such as pin-ball machines, and the like. FIGS. 6A to 6D illustrate specific examples of these electronic devices and a lighting device.

Figure 6A:
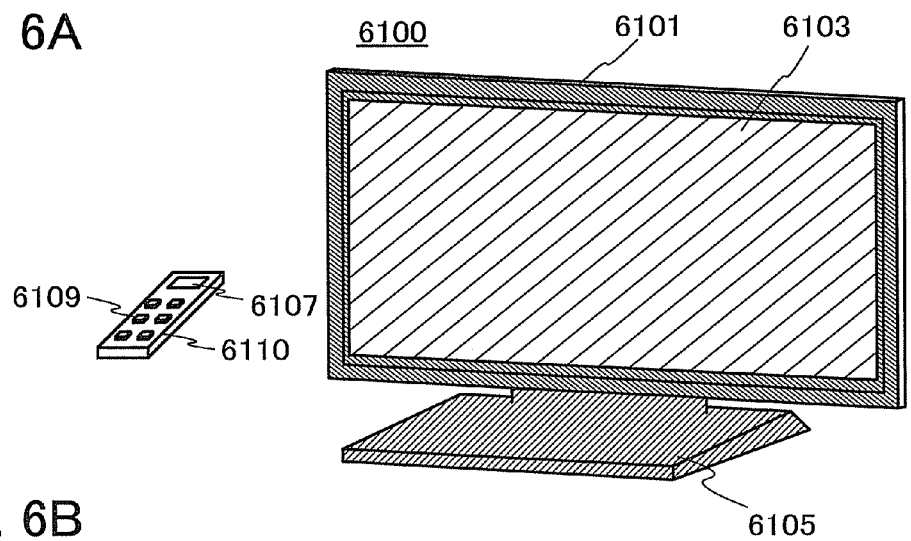
FIGS. 6A to 6D illustrate electronic devices of one embodiment of the present invention.

FIG. 6A illustrates an example of a television device. In a television device 6100, a display portion 6103 is incorporated in a housing 6101. The display portion 6103 is capable of displaying images, and the light-emitting device of one embodiment of the present invention can be used for the display portion 6103. Here, the housing 6101 is supported by a stand 6105.

The television device 6100 can be operated by an operation switch of the housing 6101 or a separate remote controller 6110. With operation keys 6109 of the remote controller 6110, channels and volume can be controlled and images displayed on the display portion 6103 can be controlled. Furthermore, the remote controller 6110 may be provided with a display portion 6107 for displaying data output from the remote controller 6110.

Note that the television device 6100 is provided with a receiver, a modem, and the like. With the receiver, a general television broadcast can be received. Furthermore, when the television device 6100 is connected to a communication network by wired or wireless connection via the modem, one-way (from a sender to a receiver) or two-way (between a sender and a receiver, between receivers, or the like) data communication can be performed.

Figure 6B:
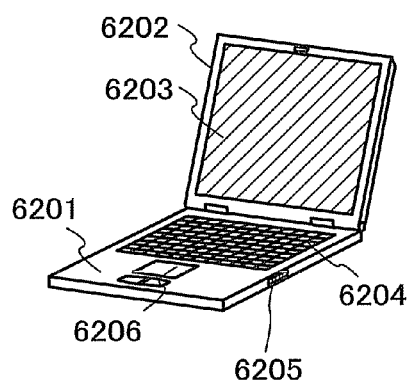

FIG. 6B illustrates a computer, which includes a main body 6201, a housing 6202, a display portion 6203, a keyboard 6204, an external connecting port 6205, a pointing device 6206, and the like. Note that this computer is manufactured by using the light-emitting device of one embodiment of the present invention for the display portion 6203.

Figure 6C:
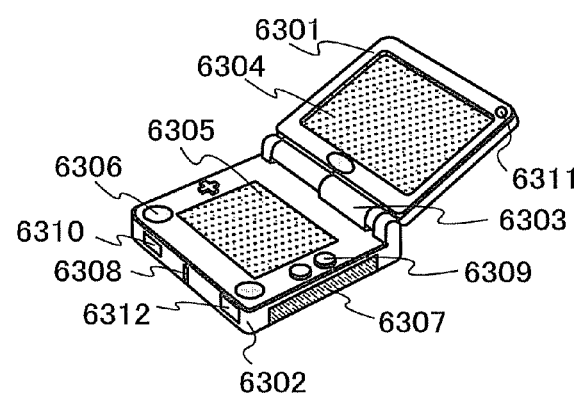

FIG. 6C illustrates a portable game machine having two housings, a housing 6301 and a housing 6302, which are connected with a joint portion 6303 so that the portable game machine can be opened or folded. A display portion 6304 is incorporated in the housing 6301 and a display portion 6305 is incorporated in the housing 6302. In addition, the portable game machine illustrated in FIG. 6C includes a speaker portion 6306, a recording medium insertion portion 6307, an LED lamp 6308, an input means (an operation key 6309, a connection terminal 6310, a sensor 6311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, smell, or infrared rays), or a microphone 6312), and the like. Needless to say, the structure of the portable game machine is not limited to the above as long as the light-emitting device of one embodiment of the present invention is used for at least either the display portion 6304 or the display portion 6305, or both, and can include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

Figure 6D:
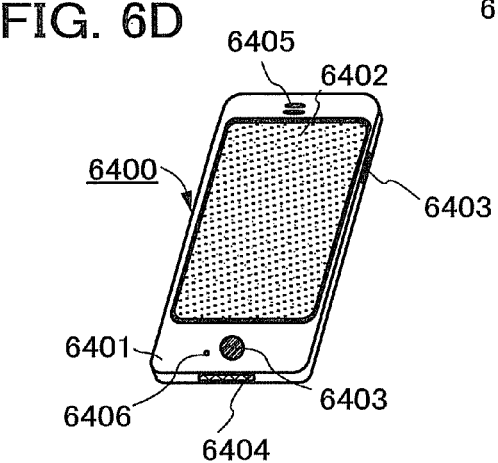

FIG. 6D illustrates an example of a mobile phone. A mobile phone 6400 is provided with a display portion 6402 incorporated in a housing 6401, operation buttons 6403, an external connection port 6404, a speaker 6405, a microphone 6406, and the like. Note that the mobile phone 6400 is manufactured with the use of the light-emitting device of one embodiment of the present invention for the display portion 6402.

When the display portion 6402 of the mobile phone 6400 illustrated in FIG. 6D is touched with a finger or the like, data can be input into the mobile phone 6400. Further, operations such as making a call and composing an e-mail can be performed by touch on the display portion 6402 with a finger or the like.

There are mainly three screen modes of the display portion 6402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 6402 so that text displayed on a screen can be inputted. In this case, it is preferable to display a keyboard or number buttons on almost the entire screen of the display portion 6402.

When a detection device including a sensor for detecting inclination, such as a gyroscope or an acceleration sensor, is provided inside the mobile phone 6400, display on the screen of the display portion 6402 can be automatically changed by determining the orientation of the mobile phone 6400 (whether the mobile phone is placed horizontally or vertically for a landscape mode or a portrait mode).

The screen modes are switched by touch on the display portion 6402 or operation with the operation buttons 6403 of the housing 6401. Alternatively, the screen modes can be switched depending on the kind of an image displayed on the display portion 6402. For example, when a signal of an image displayed on the display portion is a signal of moving image data, the screen mode is switched to the display mode; when the signal is a signal of text data, the screen mode is switched to the input mode.

Moreover, in the input mode, if a signal detected by an optical sensor in the display portion 6402 is detected and the input by touch on the display portion 6402 is not performed for a certain period, the screen mode may be controlled so as to be switched from the input mode to the display mode.

The display portion 6402 can also function as an image sensor. For example, an image of a palm print, a fingerprint, or the like is taken by touch on the display portion 6402 with the palm or the finger, whereby personal authentication can be performed. Moreover, when a backlight or a sensing light source which emits near-infrared light is provided in the display portion, an image of finger veins, palm veins, or the like can be taken.

The light-emitting device of one embodiment of the present invention includes a light-emitting element in a thin film form. Thus, when the light-emitting device is attached to a base with a curved surface, the light-emitting device with a curved surface can be obtained. In addition, when the light-emitting device is located in a housing with a curved surface, an electronic device or a lighting device with a curved surface can be obtained.

Figure 7:
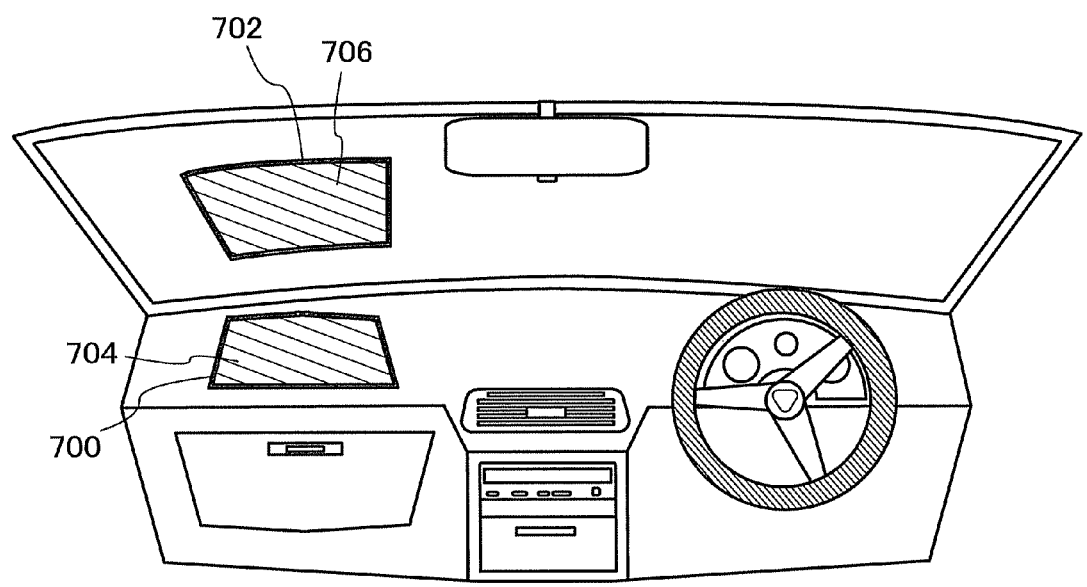
FIG. 7 illustrates an electronic device of one embodiment of the present invention.

FIG. 7 illustrates a driver's seat and the periphery thereof inside a vehicle. FIG. 7 illustrates an example in which a display device 700 is set on a dashboard and a display device 702 is set on a windshield. In the display device 700 illustrated in FIG. 7, a display portion 704 is incorporated in a housing with a curved surface and can display images. In the display device 700, the light-emitting device of one embodiment of the present invention can be used in the display portion 704.

In the display device 702 illustrated in FIG. 7, a display portion 706 is incorporated in a housing with a curved surface and the light-emitting device of one embodiment of the present invention can be used in the display portion 706. A pair of electrodes and a support of a light-emitting element which are included in the light-emitting device of one embodiment of the present invention are formed using a light-transmitting material, whereby light can be extracted through both a top surface and a bottom surface of the light-emitting device. Thus, the light-emitting device is used in the display portion 706, whereby a user can see the outside from the display portion 706 through the windshield. Similarly, a user can also see an image displayed on the display portion 706 from the outside through the windshield.

Note that instead of the display device 700 or 702 illustrated in FIG. 7, a lighting device including the light-emitting device of one embodiment of the present invention can be applied. Such a lighting device is thin and lightweight and thus brings advantages such as a reduction in the weight of the vehicle, efficient use of a space, and improvement in fuel efficiency.

Figure 8:
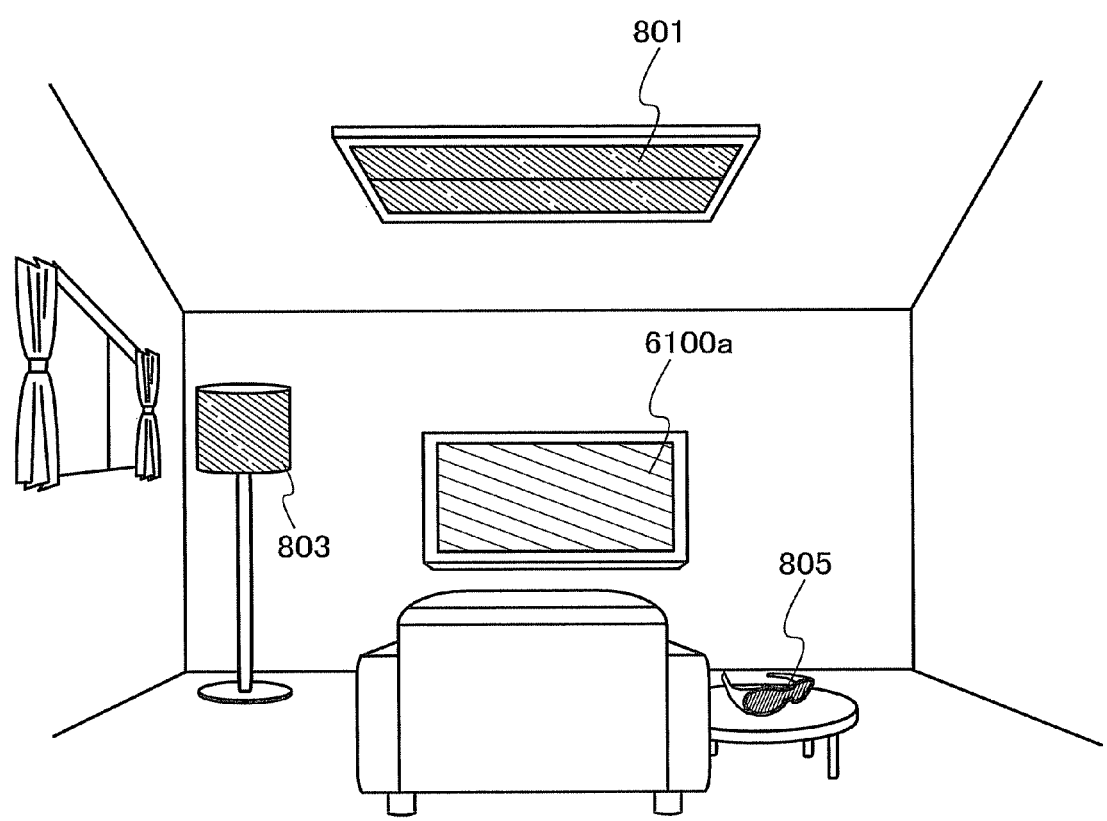
FIG. 8 illustrates electronic devices and lighting devices of one embodiment of the present invention.

FIG. 8 illustrates an example in which the lighting device including the light-emitting device of one embodiment of the present invention is used as an indoor lighting device 801. Since the area of the light-emitting device can be increased, the light-emitting device can be used as a lighting device with a large area. In addition, a lighting device 803 in which a light-emitting region has a curved surface can also be obtained with the use of a housing with a curved surface. A light-emitting element included in the lighting device described in this embodiment is in a thin film fowl, which allows the housing to be designed more freely. Therefore, the lighting device can be elaborately designed in a variety of ways.

A television device 6100a that is a television device one example of which is illustrated in FIG. 6A can be set in a room provided with the lighting device to which one embodiment of the present invention is applied. The television device 6100a may have a three-dimensional display function as well as a normal two-dimensional display function. In FIG. 8, a three-dimensional image can be watched with glasses 805 for watching three-dimensional images.

As described above, the electronic devices and the lighting devices can be obtained by application of the light-emitting element and the light-emitting device. The light-emitting element and the light-emitting device have a remarkably wide application range, and thus can be applied to electronic devices and lighting devices in a variety of fields.

Note that the structure described in this embodiment can be combined with any of the structures described in Embodiments 1 to 4 as appropriate.

Example 1

In this example, Synthesis Example 1 is described in which 2-[4-(dibenzothiophen-4-yl)phenyl]benzoxazole (abbreviation: DBTBOx-II) which is represented by Structural Formula (100) in Embodiment 1 is synthesized.

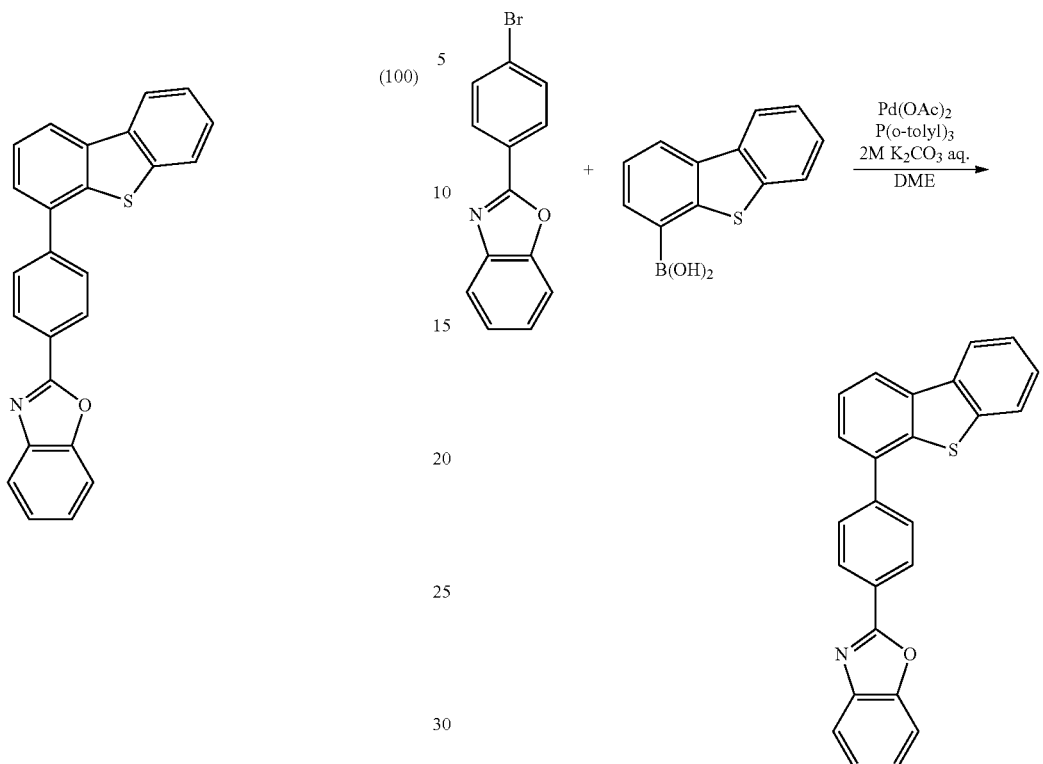

(F1-1)

Synthesis Example 1

In a 300-mL three-neck flask, a mixture of 1.1 g (4.0 mmol) of 2-(4-bromophenyl)benzoxazole, 1.0 g (4.2 mmol) of dibenzothiophene-4-boronic acid, 0.14 g (0.46 mmol) of tri(o-tolyl)phosphine, 40 mL of ethylene glycol dimethyl ether, and 4.0 mL of a 2M aqueous potassium carbonate solution was deaerated while being stirred under reduced pressure, and then, the air in the flask was replaced with nitrogen. Then, 28 mg (0.13 mmol) of palladium(II) acetate was added to this mixture, and the mixture was stirred at 80° C. for six hours in a nitrogen atmosphere.

After the stirring, water was added to the mixture, and an aqueous layer was extracted with toluene. The obtained extract and the organic layer were combined, washed with brine, and dried with magnesium sulfate. This mixture was subjected to gravity filtration, and the filtrate was condensed to obtain a solid. The obtained solid was purified by silica gel column chromatography. At this time, a mixed solvent of toluene and hexane (toluene:hexane=2:1) was used as a developing solvent for the chromatography. The obtained fractions were concentrated and a mixed solvent of toluene and hexane was added thereto to allow precipitation of a crystal, giving 1.4 g of a white powder in a yield of 90%, which was the substance to be produced.

By a train sublimation method, 1.4 g of the obtained white powder was purified. The sublimation purification was conducted by heating of the white powder at 200° C. under a pressure of 2.6 Pa with a flow rate of argon gas of 5 mL/min for 20 hours. After the sublimation purification, 0.79 g of a white powder of the substance to be produced was obtained in a yield of 58%. The reaction scheme of Synthesis Example 1 above is shown in (F1-1).

The compound obtained in Synthesis Example 1 was identified by a nuclear magnetic resonance (NMR) method. The measurement data are shown below.

$^1$H NMR (CDCl$_3$, 300 MHz): δ (ppm)=7.36-7.42 (m, 2H), 7.46-7.51 (m, 2H), 7.54-7.65 (m, 3H), 7.81-7.88 (m, 2H), 7.93 (d, J=9.0 Hz, 2H), 8.19-8.23 (m, 2H), 8.42 (d, J=8.7 Hz, 2H).

Figure 9A:
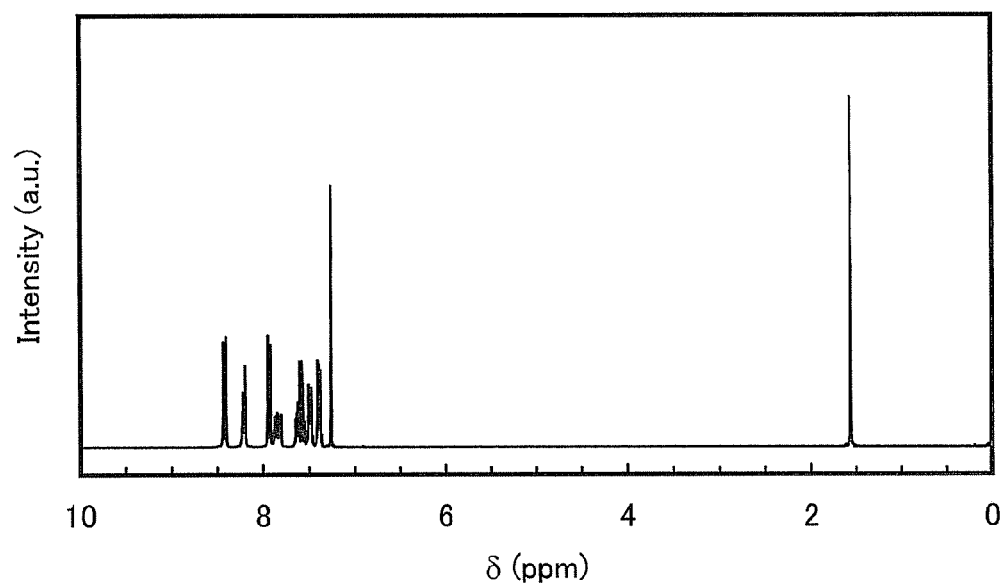
FIGS. 9A and 9B are NMR charts of DBTBOx-II.
Figure 9B:
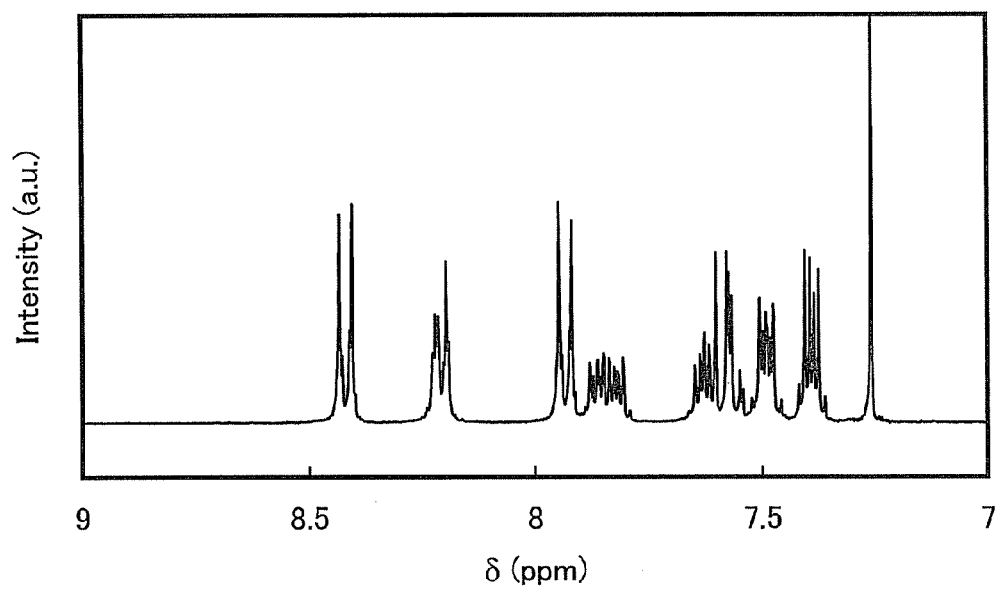

FIGS. 9A and 9B are $^1$H NMR charts. Note that FIG. 9B is a chart showing an enlarged part of FIG. 9A in the range of 7.0 ppm to 9.0 ppm. From the measurement data, the compound obtained in Synthesis Example 1 was identified as DBTBOx-II.

Figure 10:
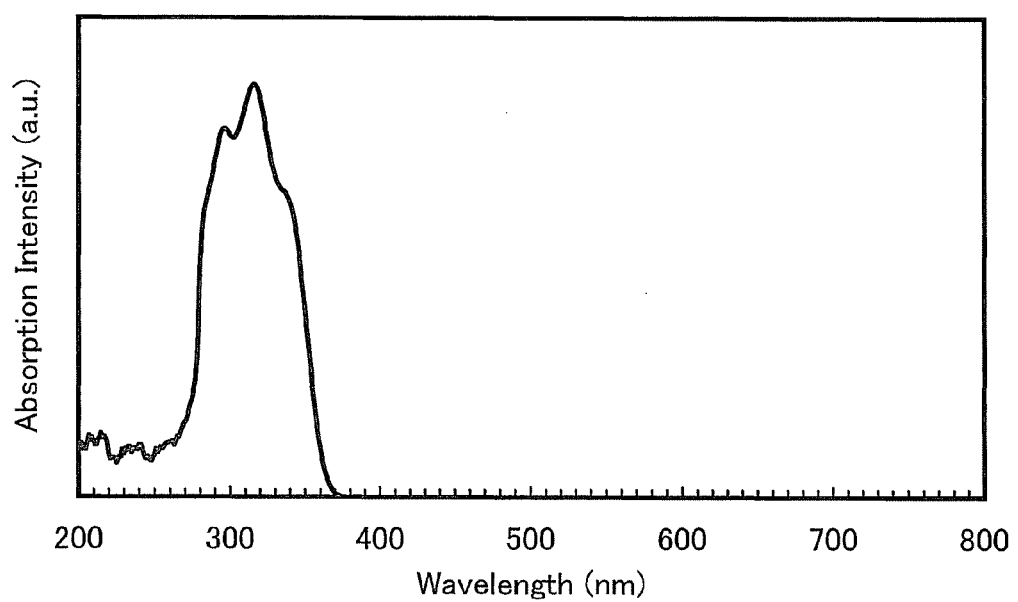
FIG. 10 shows an absorption spectrum of DBTBOx-II in toluene.
Figure 11:
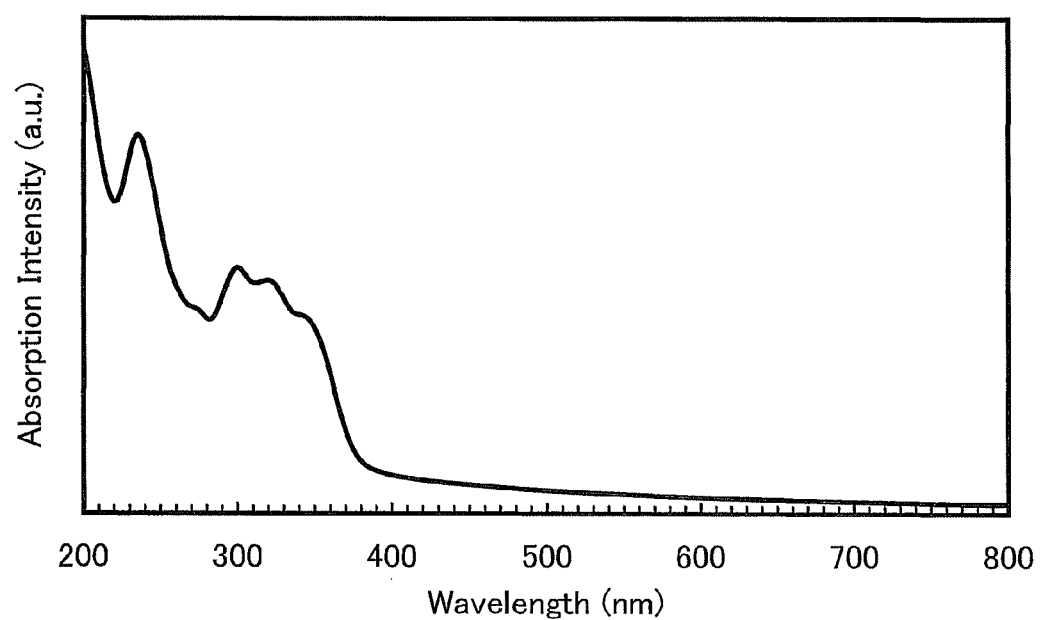
FIG. 11 shows an absorption spectrum of a thin film of DBTBOx-II.
Figure 12:
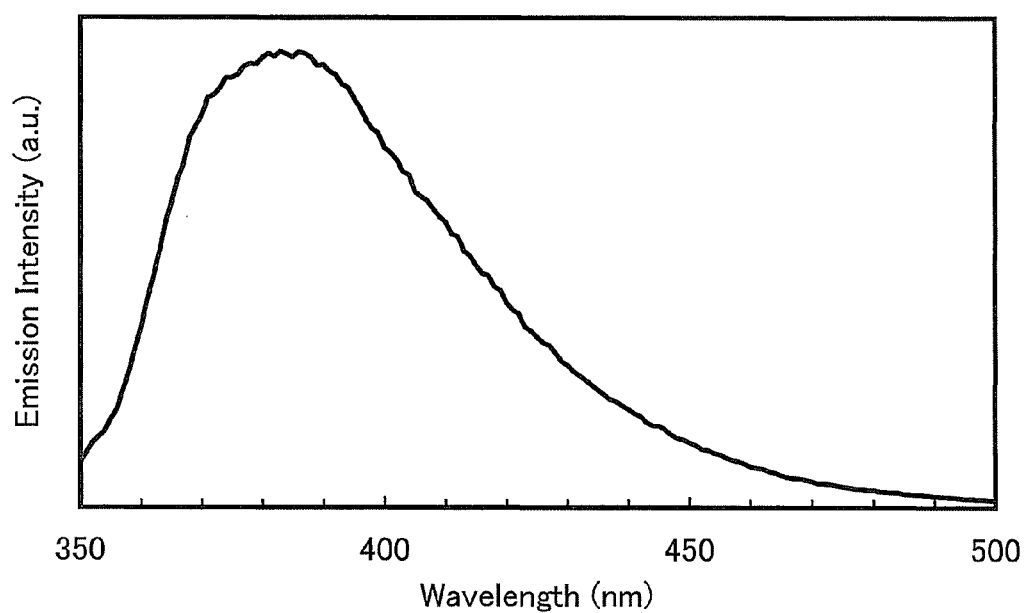
FIG. 12 shows an emission spectrum of DBTBOx-II in toluene.
Figure 13:
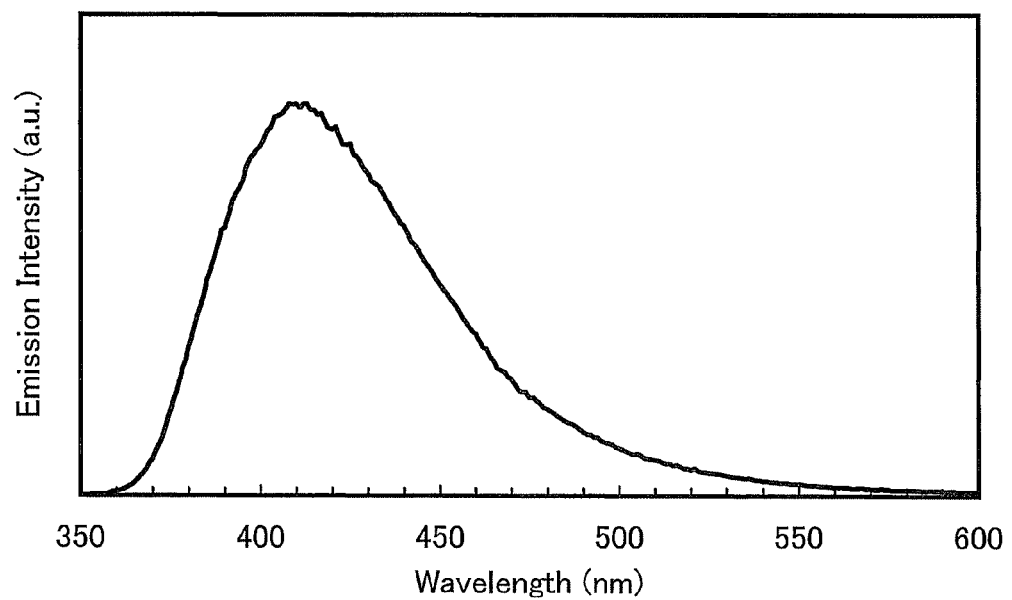
FIG. 13 shows an emission spectrum of a thin film of DBTBOx-II.

An absorption spectrum of a toluene solution of DBTBOx-II is shown in FIG. 10. An absorption spectrum of a thin film of DBTBOx-II is shown in FIG. 11. An ultraviolet-visible spectrophotometer (V-550, manufactured by JASCO Corporation) was used for the measurements. The solution was put into a quartz cell. The thin film was formed by evaporation over a quartz substrate to form a sample. The absorption spectrum of DBTBOx-II in toluene in FIG. 10 was obtained by subtracting the absorption spectra of the quartz cell and toluene from a raw data, and the absorption spectrum of the thin film of DBTBOx-II in FIG. 11 was obtained by subtracting the absorption spectrum of the quartz substrate from a raw data. In FIG. 10 and FIG. 11, the horizontal axis represents the wavelength (nm) and the vertical axis represents the absorption intensity (arbitrary unit). In the case of the toluene solution, absorption peaks were observed at 316 nm, and 338 nm, and in the case of the thin film, the absorption peaks were observed at 236 nm, 300 nm, 320 nm, and 342 nm. An emission spectrum of DBTBOx-II in toluene is shown in FIG. 12. An emission spectrum of the thin film of DBTBOx-II is shown in FIG. 13. In FIG. 12 and FIG. 13, the horizontal axis represents the wavelength (nm) and the vertical axis represents the light emission intensity (arbitrary unit). In the case of the toluene solution, a maximum emission wavelength was 386 nm (excitation wavelength: 318 nm), and in the case of the thin film, a maximum emission wavelength was 409 nm (excitation wavelength: 321 nm).

The thin film of DBTBOx-II was evaluated by photoelectron spectrometry in the air. Note that AC-2, which is a product of Riken Keiki Co., Ltd., was used for the evaluation. As a result, the HOMO level was −5.66 eV. The absorption edge was obtained from Tauc plot assuming direct transition with the absorption spectrum data of the thin film of DBTBOx-II in FIG. 11. The absorption edge was estimated as an optical energy gap, and the energy gap was 3.33 eV. The LUMO level, which was estimated from the HOMO level and the energy gap, was −2.33 eV.

From the HOMO level and the LUMO level, it was proven that DBTBOx-II is a substance having high excitation energy.

Thermogravimetry-differential thermal analysis (TG-DTA) of the obtained DBTBOx-II was performed. A high vacuum differential type differential thermal balance (type TG-DTA 2410SA, manufactured by Bruker AXS K.K.) was used for the measurement. The measurement was carried out under a nitrogen stream (a flow rate of 200 mL/min) and a normal pressure at a temperature rising rate of 10° C./min. The relationship between weight and temperature (thermogravimetry) showed that the 5% weight loss temperature was 332° C.

Example 2

In this example, Synthesis Example 2 is described in which 2-[4-(2,8-diphenyldibenzothiophen-4-yl)phenyl]benzoxazole (abbreviation: DBTBOx-III) which is represented by Structural Formula (128) in Embodiment 1 is synthesized.

Synthesis Example 2

In a 100-mL three-neck flask, a mixture of 0.82 g (3.0 mmol) of 2-(4-bromophenyl)benzoxazole, 1.1 g (3.0 mmol) of 2,8-diphenyldibenzothiophene-4-boronic acid, 0.13 g (0.43 mmol) of tri(o-tolyl)phosphine, 30 mL of ethylene glycol dimethyl ether, and 3.0 mL of a 2M aqueous potassium carbonate solution was deaerated while being stirred under reduced pressure, and then, the air in the flask was replaced with nitrogen. Then, 26 mg (0.12 mmol) of palladium(II) acetate was added to this mixture, and the mixture was stirred at 80° C. for four hours in a nitrogen atmosphere.

After the stirring, water was added to the mixture, and an aqueous layer was extracted with toluene. The obtained extract and the organic layer were combined, washed with brine, and dried with magnesium sulfate. The obtained mixture was subjected to gravity filtration, and the filtrate was condensed to obtain an oily substance. The obtained oily substance was purified by silica gel column chromatography. At this time, toluene was used as a developing solvent for the chromatography. The obtained fractions were concentrated, and toluene was added to the residue to allow precipitation of a crystal, giving 1.2 g of a white powder in a yield of 73%, which was the substance to be produced.

By a train sublimation method, 1.1 g of the obtained white powder was subjected to sublimation purification. The sublimation purification was conducted by heating of the white powder at 270° C. under a pressure of 2.9 Pa with a flow rate of argon gas of 5 mL/min for 16 hours. After the sublimation purification, 1.0 g of a white powder of the substance to be produced was obtained in a yield of 90%. The reaction scheme of Synthesis Example 2 above is shown in (F1-2).

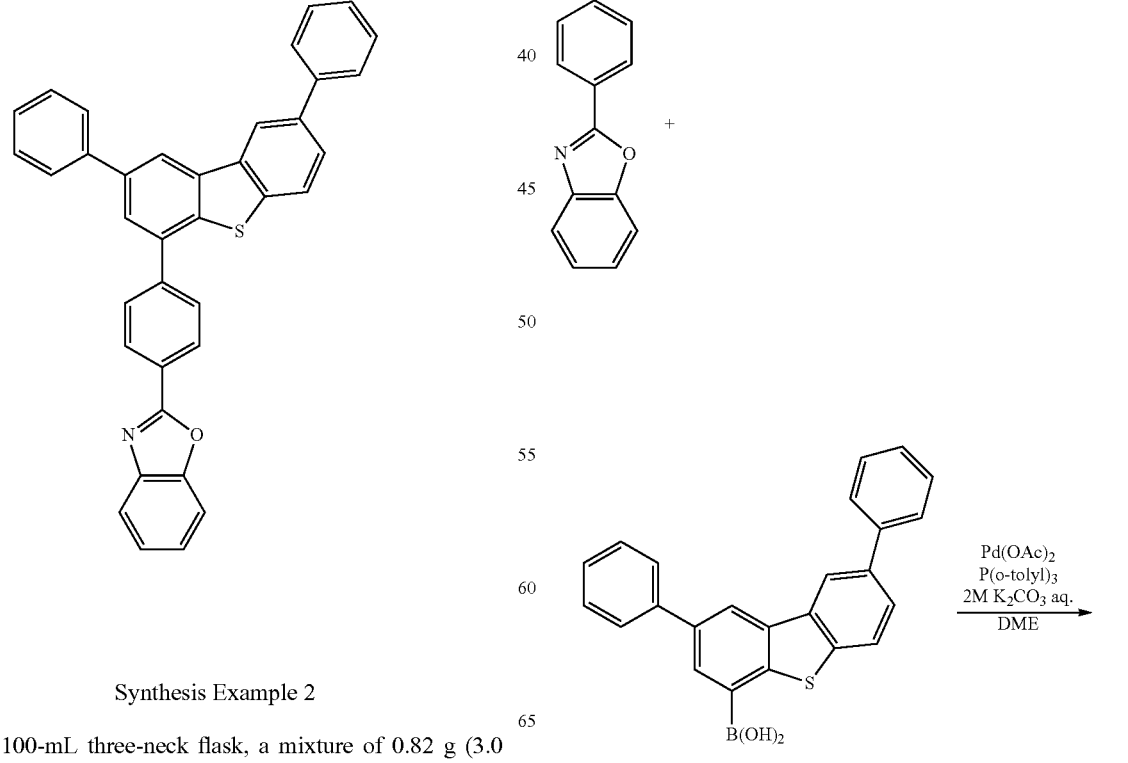

-continued

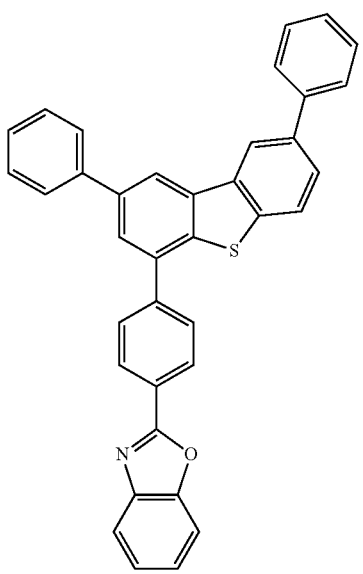

The compound obtained in Synthesis Example 2 was identified by a nuclear magnetic resonance (NMR) method. The measurement data are shown below.

$^1$H NMR (CDCl$_3$, 300 MHz): δ (ppm)=7.37-7.45 (m, 4H), 7.49-7.56 (m, 4H), 7.63-7.66 (m, 1H), 7.74-7.84 (m, 7H), 7.93 (d, J=8.1 Hz, 1H), 8.00 (d, J=8.4 Hz, 2H), 8.44-8.47 (m, 4H).

Figure 14A:
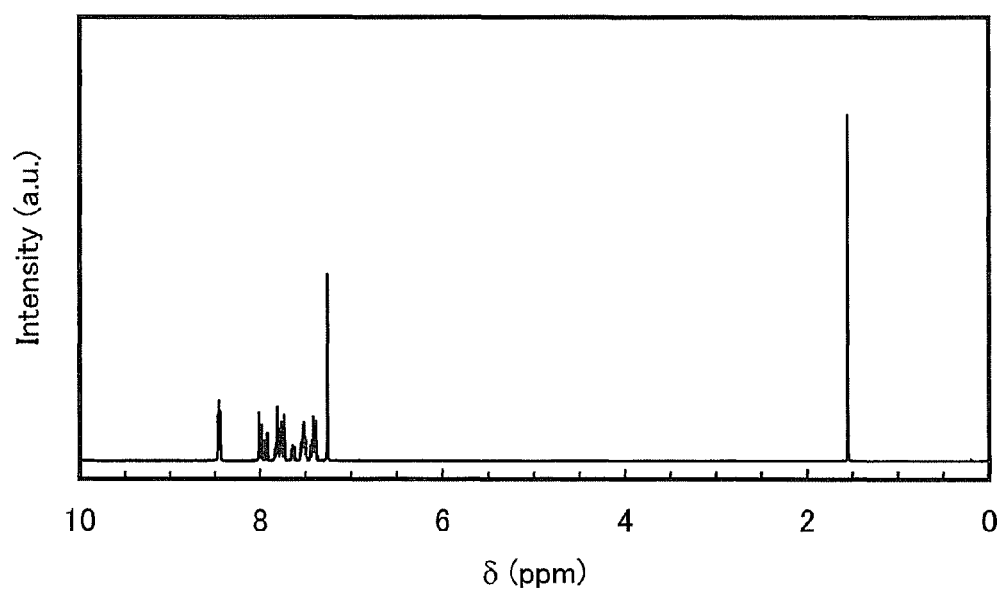
FIGS. 14A and 14B are NMR charts of DBTBOx-III.
Figure 14B:
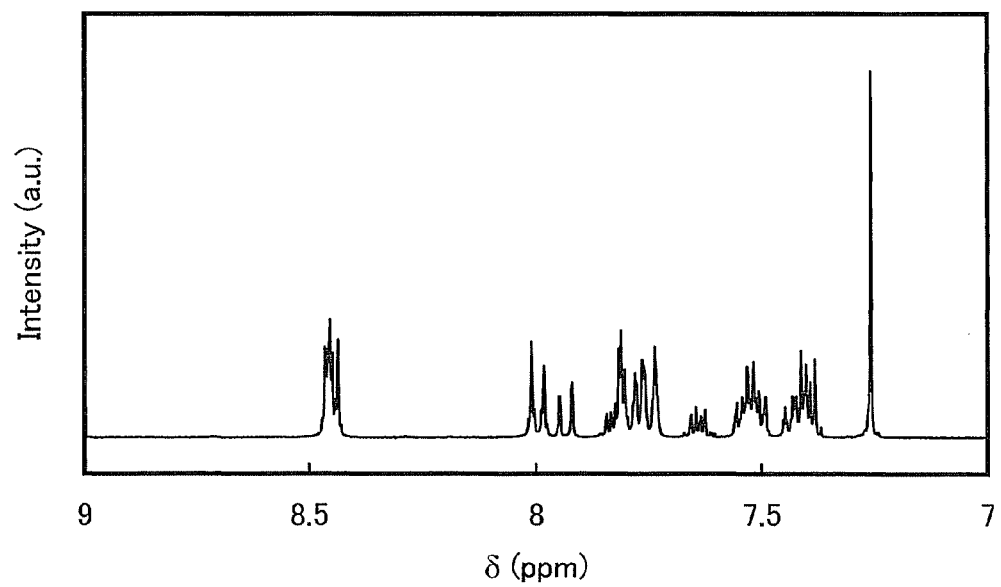

FIGS. 14A and 14B are $^1$H NMR charts. Note that FIG. 14B is a chart showing an enlarged part of FIG. 14A in the range of 7.0 ppm to 9.0 ppm. From the measurement data, the compound obtained in Synthesis Example 2 was identified as DBTBOx-III.

Figure 15:
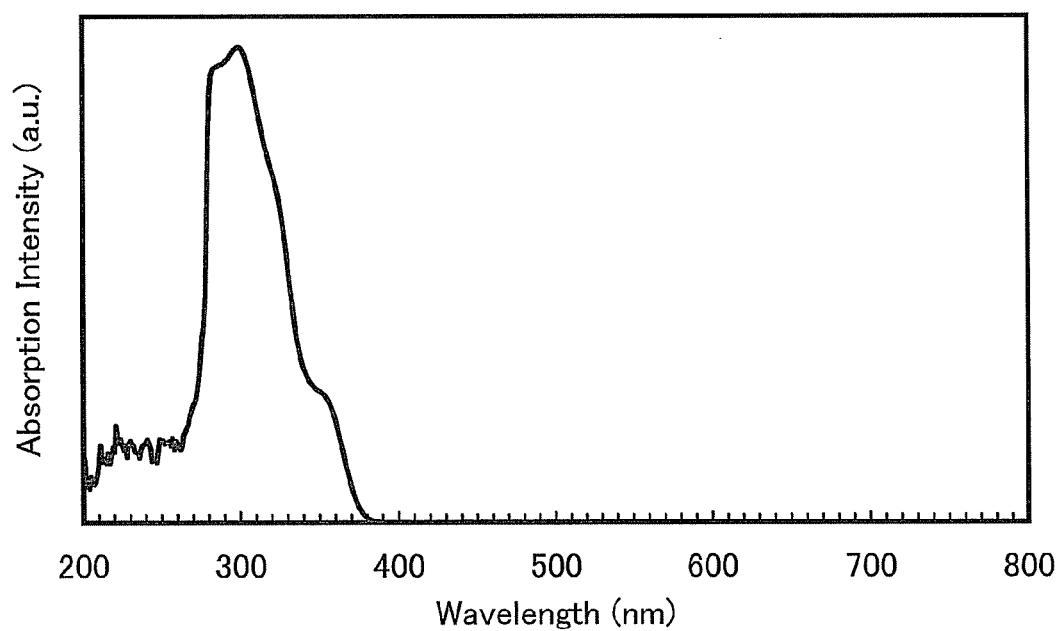
FIG. 15 shows an absorption spectrum of DBTBOx-III in toluene.
Figure 16:
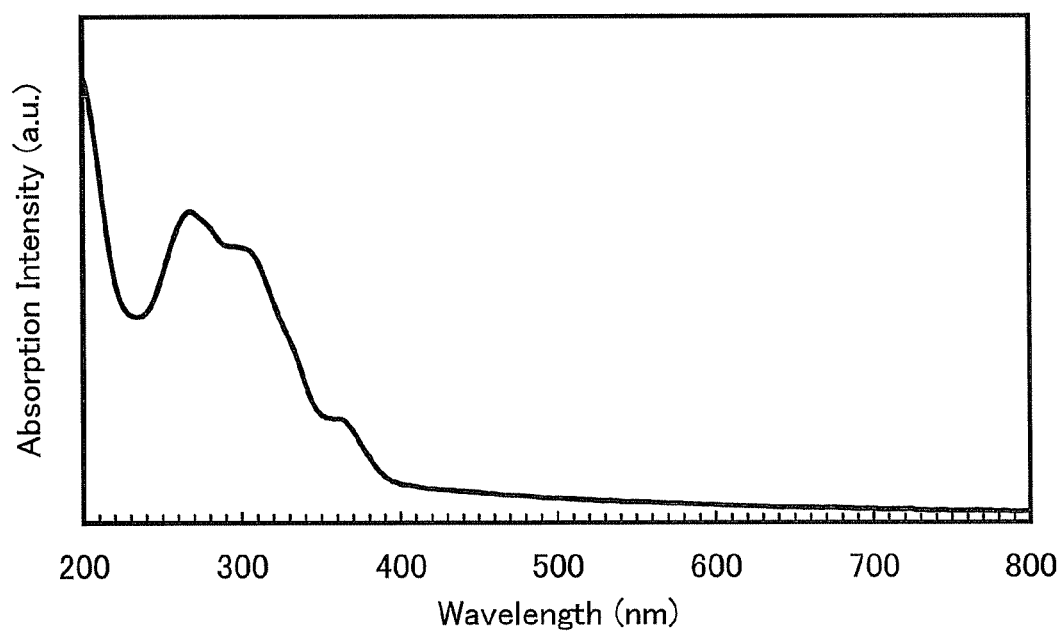
FIG. 16 shows an absorption spectrum of a thin film of DBTBOx-III.
Figure 17:
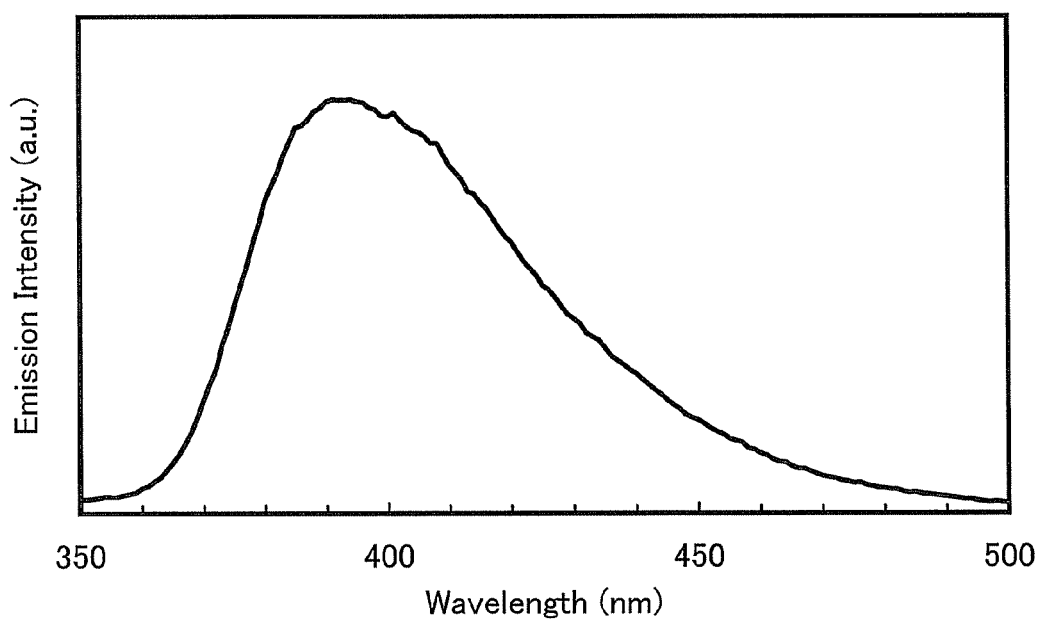
FIG. 17 shows an emission spectrum of DBTBOx-III in toluene.
Figure 18:
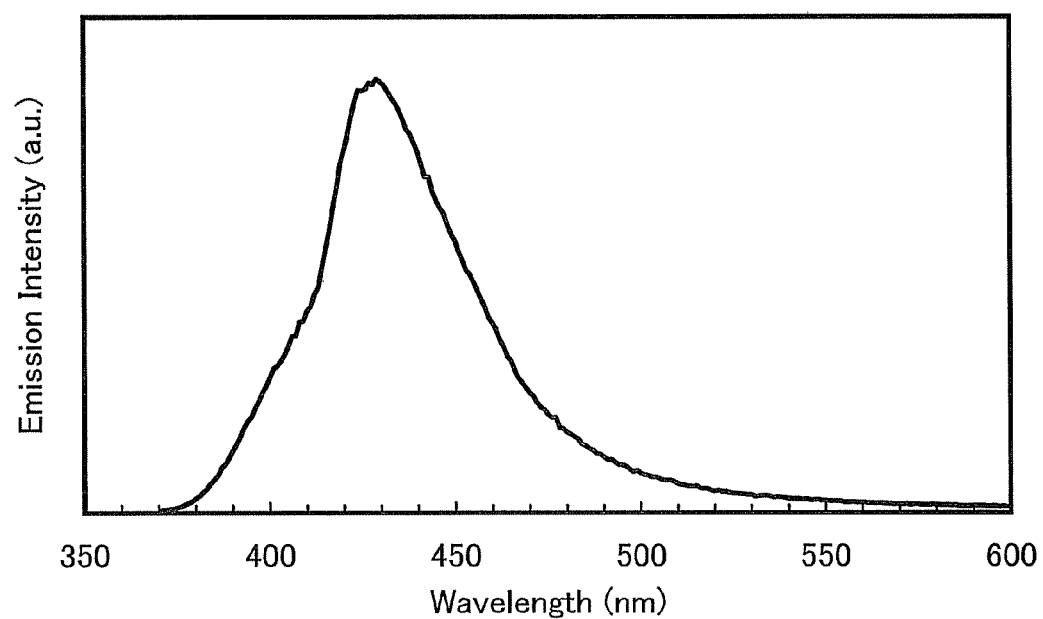
FIG. 18 shows an emission spectrum of a thin film of DBTBOx-III.

An absorption spectrum of DBTBOx-III in toluene is shown in FIG. 15. An absorption spectrum of a thin film of DBTBOx-III is shown in FIG. 16. An ultraviolet-visible spectrophotometer (V-550, manufactured by JASCO Corporation) was used for the measurements. The solution was put into a quartz cell. The thin film was formed by evaporation over a quartz substrate to form a sample. The absorption spectrum of DBTBOx-II in toluene in FIG. 15 was obtained by subtracting the absorption spectra of the quartz cell and toluene from a raw data, and the absorption spectrum of the thin film of DBTBOx-II in FIG. 16 was obtained by subtracting the absorption spectrum of the quartz substrate from a raw data. In FIG. 15 and FIG. 16, the horizontal axis represents the wavelength (nm) and the vertical axis represents the absorption intensity (arbitrary unit). In the case of the toluene solution, absorption peaks were observed at 299 nm, 320 nm, and 351 nm, and in the case of the thin film, absorption peaks were observed at 268 nm, 301 nm, and 362 nm. An emission spectrum of DBTBOx-III in toluene is shown in FIG. 17. An emission spectrum of the thin film of DBTBOx-III is shown in FIG. 18. In FIG. 17 and FIG. 18, the horizontal axis represents the wavelength (nm) and the vertical axis represents the light emission intensity (arbitrary unit). In the case of the toluene solution, a maximum emission wavelength was 393 nm (excitation wavelength: 300 nm), and in the case of the thin film, a maximum emission wavelength was 429 nm (excitation wavelength: 364 nm).

The thin film of DBTBOx-III was evaluated by photoelectron spectrometry in the air. Note that AC-2, which is a product of Riken Keiki Co., Ltd., was used for the evaluation. As a result, the HOMO level was −5.88 eV. The absorption edge was obtained from Tauc plot assuming direct transition with the absorption spectrum data of the thin film of DBTBOx-III in FIG. 16. The absorption edge was estimated as an optical energy gap, and the energy gap was 3.19 eV. The LUMO level, which was estimated from the HOMO level and the energy gap, was −2.69 eV.

From the HOMO level and the LUMO level, it was proven that DBTBOx-III is a substance having high excitation energy.

Example 3

In this example, a method for manufacturing a light-emitting element of one embodiment of the present invention and measurement results of element characteristics thereof will be described. Specifically, a light-emitting element 1 formed using 2-[4-(2,8-diphenyldibenzothiophen-4-yl)phenyl]benzoxazole (abbreviation: DBTBOx-III) which is described in Example 2 will be described.

Figure 19:
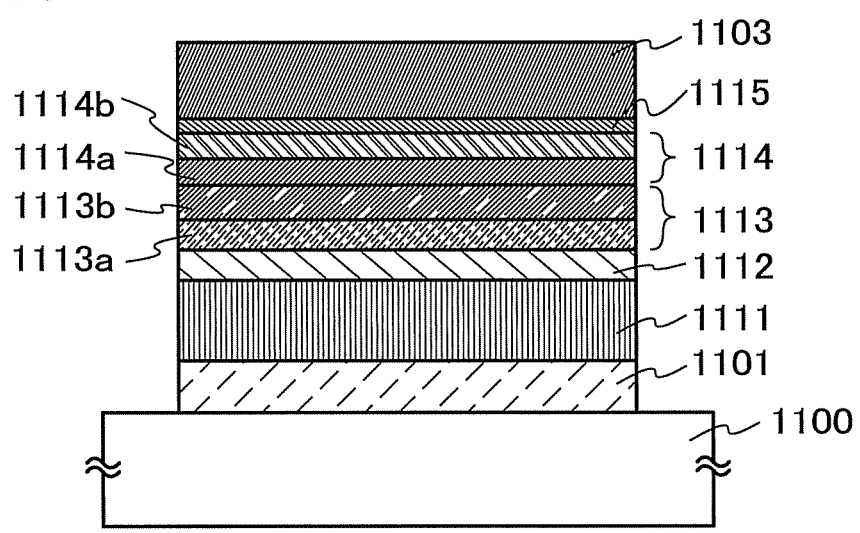
FIG. 19 illustrates a light-emitting element in Example 3.

A method for manufacturing a light-emitting element 1 of this example will be described below with reference, to FIG. 19. A structural formula of an organic compound used in this example is shown below.

(128)

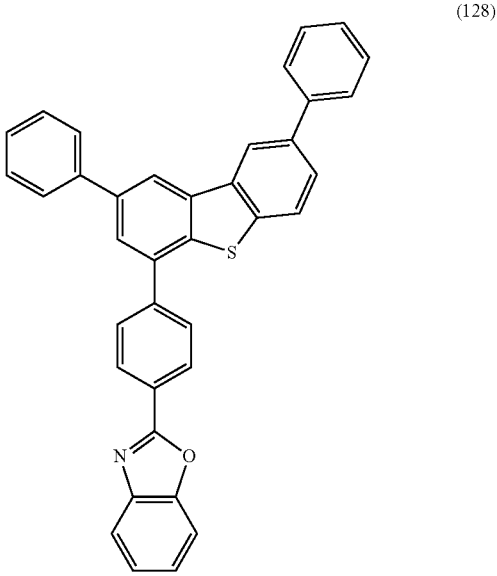 [SMILES: c1ccc(-c2ccc3sc4c(-c5ccc(-c6nc7ccccc7o6)cc5)cc(-c5ccccc5)cc4c3c2)cc1]

(Light-Emitting Element 1)

First, indium tin oxide containing silicon oxide (ITSO) was deposited on a substrate 1100 by a sputtering method, whereby a first electrode 1101 was formed. Note that the thickness was 110 nm and the electrode area was 2 mm×2 mm. In this example, the first electrode 1101 was used as an anode.

Next, the substrate 1100 provided with the first electrode 1101 was fixed to a substrate holder in a vacuum evaporation apparatus so that a surface on which the first electrode 1101 was provided faced downward. The pressure in the vacuum evaporation apparatus was reduced to about $10^{-4}$ Pa. After that, 4-phenyl-4'-(9-phenylfluoren-9-yl)triphenylamine (abbreviation: BPAFLP) and molybdenum(VI) oxide were co-evaporated, whereby a hole-injection layer 1111 was formed on the first electrode 1101. The thickness of the hole-injection layer 1111 was 50 nm. The weight ratio of BPAFLP to molybdenum oxide was adjusted to be 4:2 (=BPAFLP:molybdenum oxide). Note that the co-evaporation method refers to an evaporation method in which evaporation is carried out from a plurality of evaporation sources at the same time in one treatment chamber.

Next, BPAFLP was deposited to a thickness of 10 nm on the hole-injection layer 1111, whereby a hole-transport layer 1112 was formed.

Further, a light-emitting layer 1113 was formed on the hole-transport layer 1112. The light-emitting layer 1113 was formed by stacking a first film 1113a and a second film 1113b in this order.

The first film 1113a of the light-emitting layer 1113 was formed by co-evaporating DBTBOx-III as a first host material, 4-phenyl-4'-(9-phenyl-9H-carbazol-3-yl)triphenylamine (abbreviation: PCBA1BP) as a second host material which is different from the first host material, and tris(2-phenylpyridinato-N,C$^{2'}$)iridium(III) (abbreviation: Ir(ppy)$_3$) as a guest material. The weight ratio of DBTBOx-III, PCBA1BP, and Ir(ppy)$_3$ was adjusted to be 1:0.2:0.08 (=DBTBOx-III:PCBA1BP:Ir(ppy)$_3$). The thickness of the first film 1113a was set to 20 nm.

The second film 1113b of the light-emitting layer 1113 was formed by co-evaporating DBTBOx-III as a host material and Ir(ppy)$_3$ as a guest material. The weight ratio of DBTBOx-III to Ir(ppy)$_3$ was adjusted to be 1:0.08 (=DBTBOx-III:Ir(ppy)$_3$). The thickness of the second film 1113b was set to 20 nm.

Then, an electron-transport layer 1114 was &timed over the light-emitting layer 1113. The electron-transport layer 1114 was formed by stacking a first film 1114a and a second film 1114b in this order.

The first film 1114a of the electron-transport layer 1114 was formed by evaporation of DBTBOx-III. The thickness of the first film 1114a was 15 nm.

The second film 1114b of the electron-transport layer 1114 was formed by evaporation of bathophenanthroline (abbreviation: BPhen) which is a material different from the benzoxazole derivative. The thickness of the second film 1114b was 15 nm.

Furthermore, a lithium fluoride (LiF) film was formed to a thickness of 1 nm on the electron-transport layer 1114 by evaporation, whereby an electron-injection layer 1115 was formed.

Lastly, a 200-nm-thick film of aluminum was formed by evaporation, whereby a second electrode 1103 functioning as a cathode was formed. Thus, the light-emitting element 1 of this example was manufactured.

Note that a resistance heating method was used in all of the above evaporation steps.

Table 1 shows an element structure of the light-emitting element 1 obtained as described above.

TABLE 1

| | First electrode | Hole-injection | Hole-transport | Light-emitting layer 1113 | | Electron-transport layer 1114 | | Electron-injection | Second electrode |
|---|---|---|---|---|---|---|---|---|---|
| | 1101 | layer 1111 | layer 1112 | 1113a | 1113b | 1114a | 1114b | layer 1115 | 1103 |
| Light-emitting element 1 | ITSO 110 nm | BPAFLP:MoOx (= 4:2) 50 nm | BPAFLP 10 nm | DBTBOx-III:PCBA1BP:Ir(ppy)$_3$ (= 1:0.2:0.08) 20 nm | DBTBOx-III:Ir(ppy)$_3$ (= 1:0.08) 20 nm | DBTBOx-III 15 nm | BPhen 15 nm | LiF 1 nm | Al 200 nm |

In a glove box containing a nitrogen atmosphere, the light-emitting element 1 was sealed so as not to be exposed to the air. Then, operation characteristics of the light-emitting element were measured. Note that the measurement was carried out at room temperature (in an atmosphere kept at 25° C.).

Table 2 shows the voltage (V), current density (mA/cm$^2$), CIE chromaticity coordinates (x, y), luminance (cd/m$^2$), current efficiency (cd/A), and power efficiency (lm/W) of the light-emitting element 1 at a luminance of about 800 cd/m$^2$.

TABLE 2

| | Voltage (V) | Current density (mA/cm$^2$) | Chromaticity (x, y) | Luminance (cd/m$^2$) | Current efficiency (cd/A) | Power efficiency (lm/W) |
|---|---|---|---|---|---|---|
| Light-emitting element 1 | 3.0 | 1.34 | (0.34, 0.61) | 774 | 57.9 | 60.6 |

Figure 20:
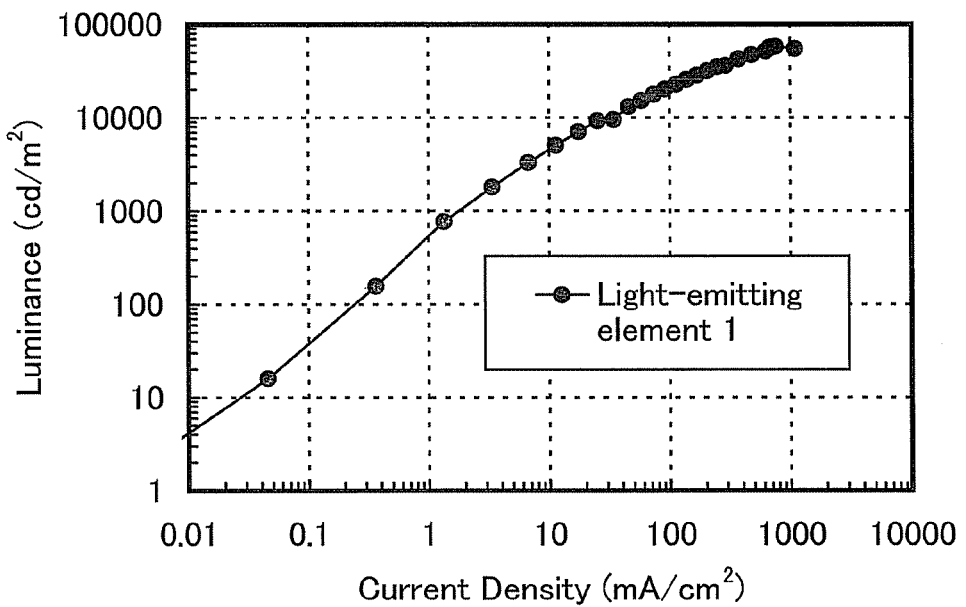
FIG. 20 shows current density-luminance characteristics of a light-emitting element in Example 3.
Figure 21:
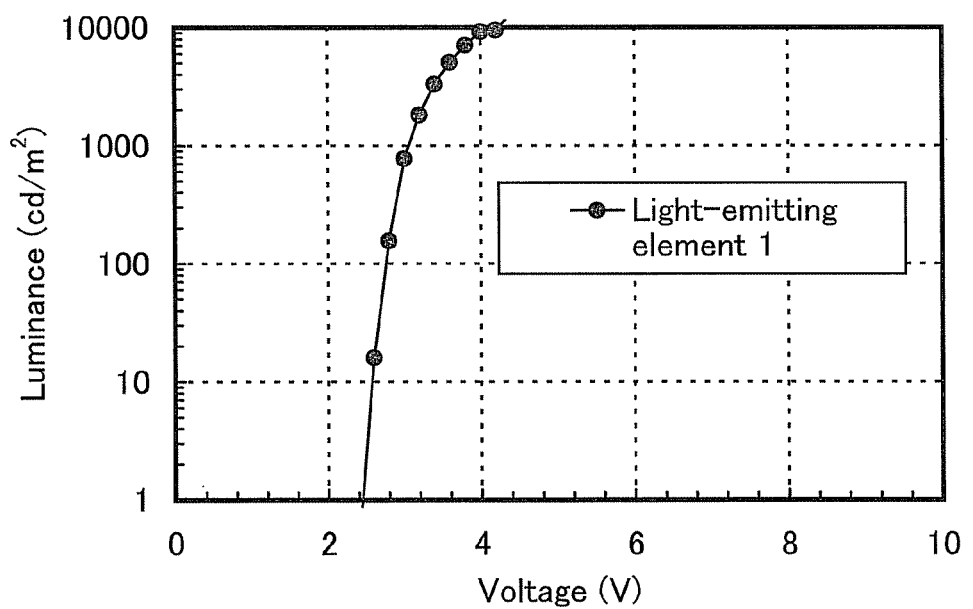
FIG. 21 shows voltage-luminance characteristics of the light-emitting element in Example 3.
Figure 22:
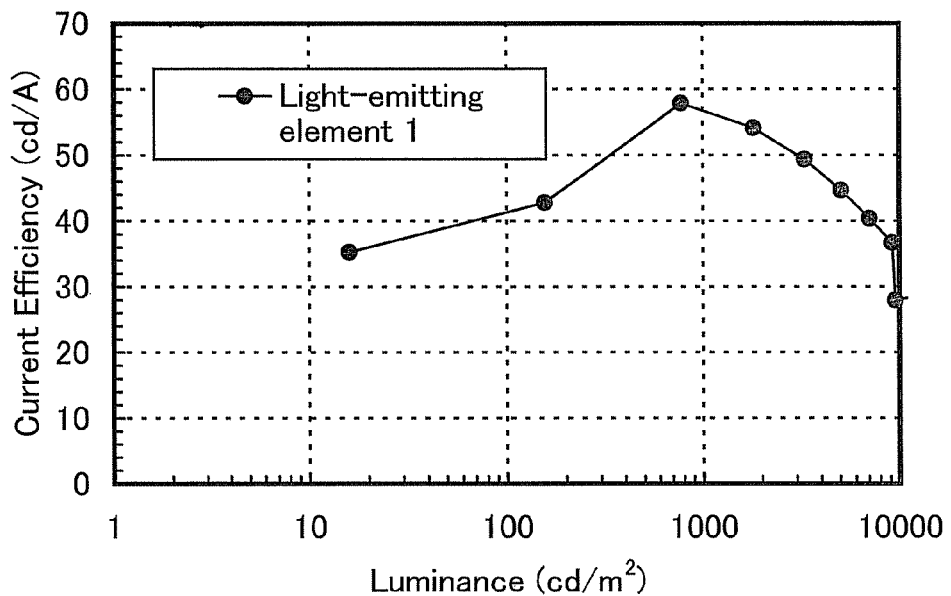
FIG. 22 shows luminance-current efficiency characteristics of the light-emitting element in Example 3.
Figure 23:
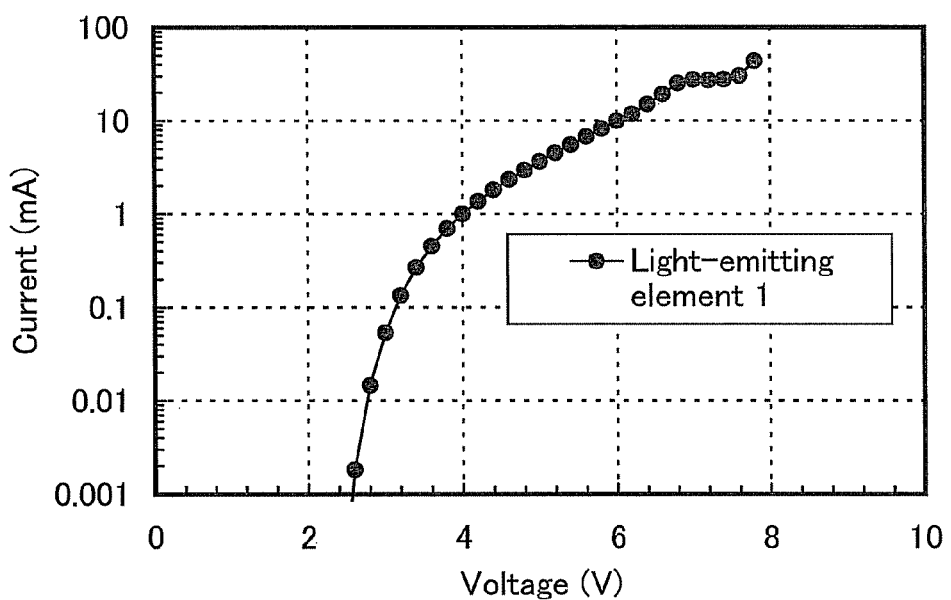
FIG. 23 shows voltage-current characteristics of the light-emitting element in Example 3.

FIG. 20 shows current density-luminance characteristics of the light-emitting element 1. FIG. 21 shows voltage-luminance characteristics thereof. FIG. 22 shows luminance-current efficiency characteristics thereof. FIG. 23 shows voltage-current characteristics thereof. In FIG. 20, the vertical axis represents luminance (cd/m$^2$) and the horizontal axis represents current density (mA/cm$^2$). In FIG. 21, the vertical axis represents luminance (cd/m$^2$) and the horizontal axis represents voltage (V). In FIG. 22, the vertical axis represents current efficiency (cd/A) and the horizontal axis represents luminance (cd/m$^2$). In FIG. 23, the vertical axis represents current (mA) and the horizontal axis represents voltage (V).

From FIG. 22, the maximum current efficiency of the light-emitting element 1 is 57.9 cd/A. This demonstrates that the light-emitting element including the benzoxazole derivative of one embodiment of the present invention has extremely high current efficiency.

Further, FIG. 20, FIG. 21, FIG. 22, FIG. 23, and Table 2 show that the light-emitting element 1 can be driven at low voltage and that the light-emitting element 1 has high current efficiency.

Figure 24:
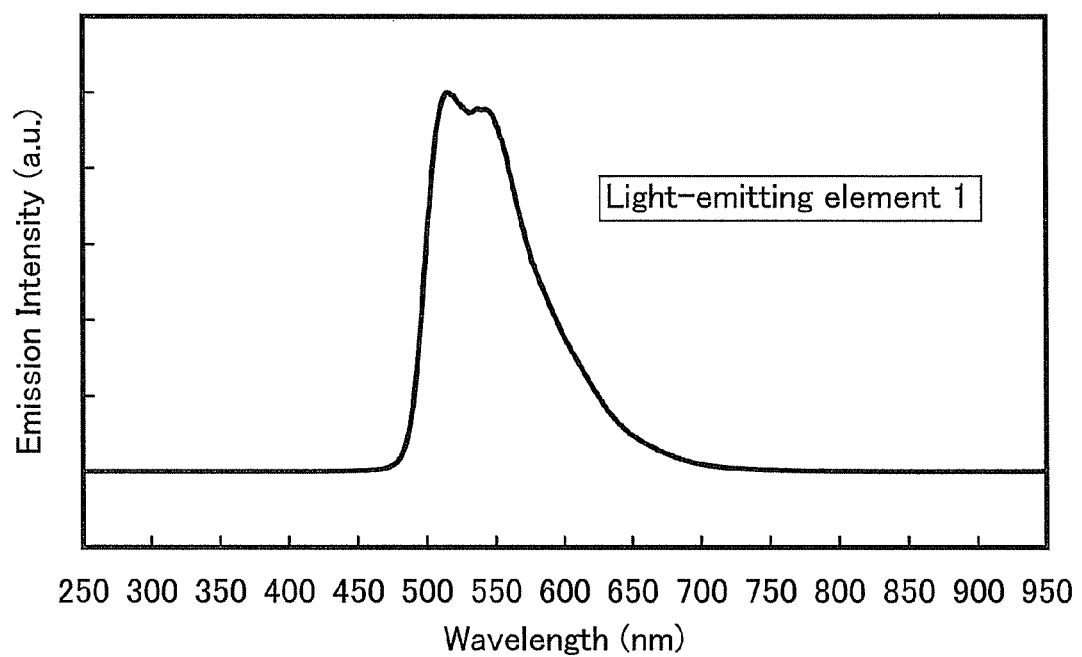
FIG. 24 shows an emission spectrum of the light-emitting element in Example 3.

FIG. 24 shows an emission spectrum of the light-emitting element 1. In FIG. 24, the vertical axis represents emission intensity (arbitrary unit) and the horizontal axis represents wavelength (nm). As shown in FIG. 24, in the light-emitting element 1, an emission wavelength provided by Ir(ppy)₃ which was used as a guest material was observed, whereas an emission wavelength provided by the benzoxazole derivative (DBTBOx-III) of one embodiment of the present invention which was used as the first host material and that provided by PCBA1BP which was used as the second host material were not observed. Therefore, it was confirmed that the benzoxazole derivative of one embodiment of the present invention serves as the host material for the light-emitting layer of the light-emitting element. Further, it was understood that DBTBOx-III is a substance having high triplet excitation energy.

Reference Example

In this reference example, an example of synthesizing 4-phenyl-4'-(9-phenylfluoren-9-yl)triphenylamine (abbreviation: BPAFLP) that was used as a material of the light-emitting element 1 will be described.

Step 1: Synthesis Method of
9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that bubble release and heat generation were confirmed. After 12 g (50 mmol) of 2-bromobiphenyl dissolved in 10 mL of dehydrated diethyl ether was slowly dripped into this mixture, the mixture was stirred and heated under reflux for 2.5 hours, whereby a Grignard reagent was prepared.

In a 500-mL three-neck flask were put 10 g (40 mmol) of 4-bromobenzophenone and 100 mL of dehydrated diethyl ether. After the Grignard reagent synthesized in advance was slowly dripped into this mixture, the mixture was heated and stirred under reflux for nine hours.

After reaction, this mixture was filtered to give a residue. The obtained residue was dissolved in 150 mL of ethyl acetate, a 1N-hydrochloric acid was added thereto until the aqueous layer became acid, and the mixture was stirred for two hours. The organic layer was washed with water. Then, magnesium sulfate was added to remove moisture. This suspension was filtered, and the resulting filtrate was concentrated to give highly viscous liquid. In a 500-mL recovery flask were put this highly viscous liquid, 50 mL of glacial acetic acid, and 1.0 mL of hydrochloric acid. The mixture was reacted by heating at 130° C. for 1.5 hours under a nitrogen atmosphere with stirring.

After reaction, this reaction mixture was filtered to give a residue. The obtained residue was washed with water, an aqueous sodium hydroxide solution, water, and methanol in this order, and then dried to give 11 g of white powder that was the substance to be produced, in a yield of 69%. The reaction scheme of Step 1 is shown (J-1) below.

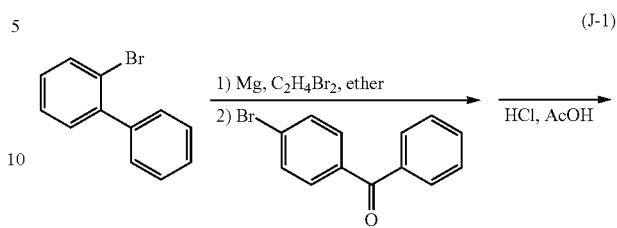

(J-1)

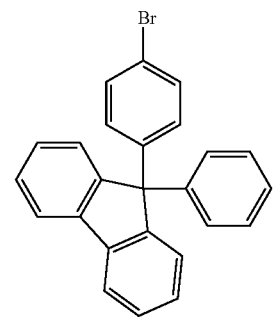

Step 2: Synthesis Method of 4-phenyl-4'-(9-phenylfluoren-9-yl)triphenylamine (abbreviation: BPAFLP)

In a 100-mL three-neck flask were put 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0:04 mmol) of bis(dibenzylideneacetone)palladium(0). The atmosphere in the flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was reacted by heating at 110° C. for two hours under a nitrogen atmosphere with stirring.

After reaction, 200 mL of toluene was added to the reaction mixture, and the resulting suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography. At this time, a mixed solvent of toluene and hexane (toluene:hexane=1:4) was used as a developing solvent for the chromatography. The obtained fractions were concentrated, and acetone and methanol were added thereto. The mixture was irradiated with ultrasonic waves and allowed a crystal to precipitate, giving 4.1 g of white powder that was the substance to be produced, in a yield of 92%. The reaction scheme of Step 2 is shown in (J-2).

(J-2)

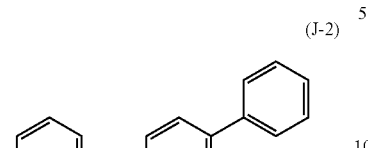

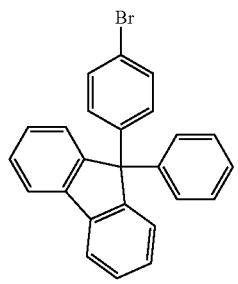

→ Pd(dba)₂, P(t-Bu)₃, t-BuONa, Xylene

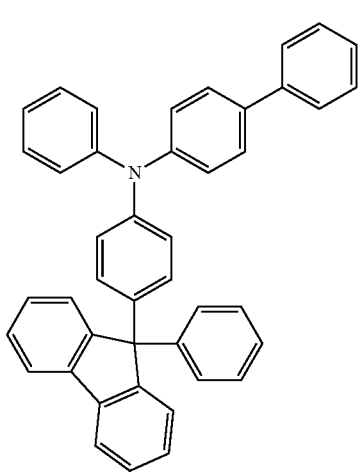

BPAFLP

The Rf values of the substance to be produced, 9-(4-bromophenyl)-9-phenylfluorene, and 4-phenyl-diphenylamine were respectively 0.41, 0.51, and 0.27, which were obtained by silica gel thin layer chromatography (TLC) (with a developing solvent containing ethyl acetate and hexane in a 1:10 ratio).

A nuclear magnetic resonance (NMR) method identified this compound as 4-phenyl-4'-(9-phenylfluoren-9-yl)triphenylamine (abbreviation: BPAFLP) that was the substance to be produced.

$^1$H NMR data of the obtained compound is as follows: $^1$H NMR (CDCl₃, 300 MHz): δ (ppm)=6.63-7.02 (m, 3H), 7.06-7.11 (H), 7.19-7.45 (m, 18H), 7.53-7.55 (m, 2H), 7.75 (d, J=6.9, 2H).

This application is based on Japanese Patent Application serial no. 2010-267158 filed with Japan Patent Office on Nov. 30, 2010, the entire contents of which are hereby incorporated by reference.

What is claimed is:

1. A benzoxazole derivative represented by Formula (G1):

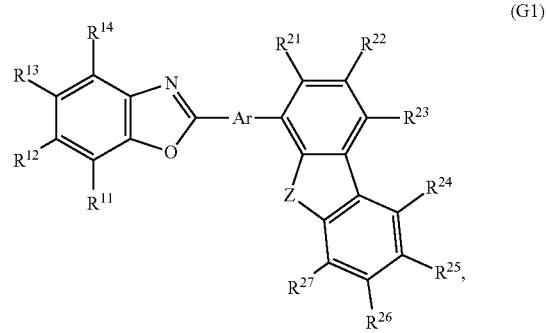

(G1)

wherein $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, wherein Ar represents a substituted or unsubstituted arylene group having 6 to 13 carbon atoms, and wherein Z represents either a sulfur atom or an oxygen atom.

2. The benzoxazole derivative according to claim 1, wherein Ar represents either a substituted or unsubstituted phenylene group or a substituted or unsubstituted biphenyldiyl group.

3. The benzoxazole derivative according to claim 1, wherein the benzoxazole derivative is represented by Formula (G2):

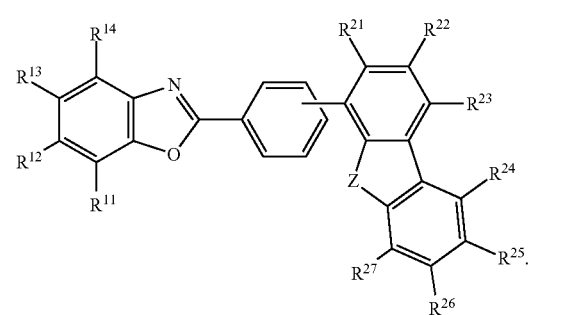

(G2)

4. A light-emitting element comprising:
a first electrode;
an electroluminescent layer over the first electrode; and
a second electrode over the electroluminescent layer,
wherein the electroluminescent layer comprises a benzoxazole derivative represented by Formula (G1):

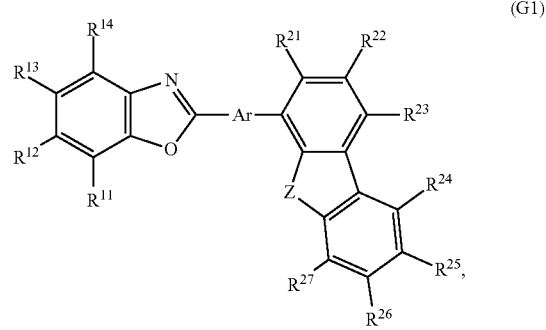

(G1)

wherein $R^{11}$ to $R^{14}$ and $R^{21}$ to $R^{27}$ separately represent any one of hydrogen, an alkyl group having 1 to 4 carbon atoms, and a substituted or unsubstituted aryl group having 6 to 13 carbon atoms, wherein Ar represents a substituted or unsubstituted arylene group having 6 to 13 carbon atoms, and wherein Z represents either a sulfur atom or an oxygen atom.

5. The light-emitting element according to claim 4, wherein Ar represents either a substituted or unsubstituted phenylene group or a substituted or unsubstituted biphenyldiyl group.

6. The light-emitting element according to claim 4, wherein the benzoxazole derivative is represented by Formula (G2):

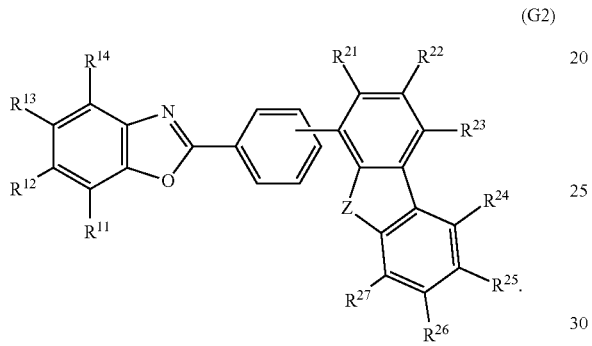

(G2)

7. The light-emitting element according to claim 4, wherein the electroluminescent layer further comprises a phosphorescent compound.

8. A lighting device including the light-emitting element according to claim 4.

9. An electronic device including the light-emitting element according to claim 4.

10. The light-emitting element according to claim 4, wherein the electroluminescent layer comprises a light-emitting layer in which the benzoxazole derivative is included.

11. The light-emitting element according to claim 10, wherein the light-emitting layer comprises a first film and a second film which is provided over and in contact with the first film, and wherein each of the first film and the second film comprises the benzoxazole derivative as a first host material and a phosphorescent compound.

12. The light-emitting element according to claim 11, wherein the first film further comprises a second host material which is different from the first host material.

13. The light-emitting element according to claim 10, wherein the electroluminescent layer further comprises an electron-transport layer over and in contact with the light-emitting layer, and wherein the electron-transport layer comprises the benzoxazole derivative.

14. The light-emitting element according to claim 13, wherein the electron-transport layer comprises a first film and a second film which is provided over and in contact with the first film, and wherein the first film comprises the benzoxazole derivative.

15. The light-emitting element according to claim 14, wherein the first film consists of the benzoxazole derivative.

16. The light-emitting element according to claim 14, wherein the second film comprises a material which is different from the benzoxazole derivative.

17. A lighting device including the light-emitting element according to claim 10.

18. An electronic device including the light-emitting element according to claim 10.

19. The benzoxazole derivative according to claim 1, wherein the benzoxazole derivative is represented by any of the following formulae:

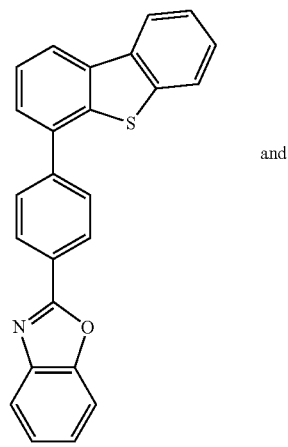

and

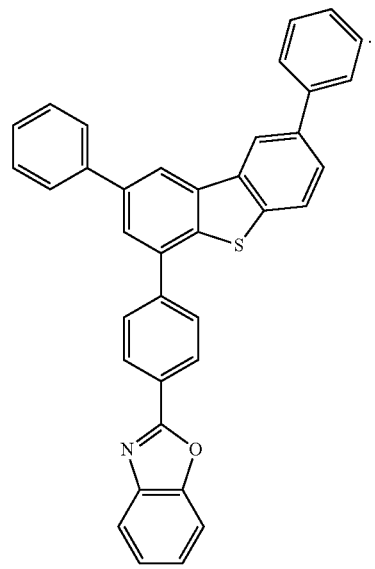

20. The light-emitting element according to claim 4, wherein the benzoxazole derivative is represented by any of the following formulae:

105
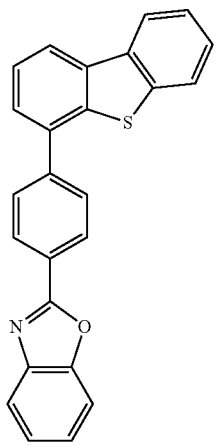
and
106
-continued
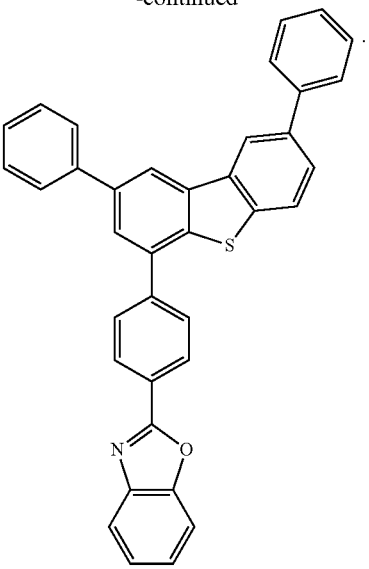
* * * * *